(12) United States Patent
Chen et al.

(10) Patent No.: US 8,569,295 B2
(45) Date of Patent: Oct. 29, 2013

(54) BICYCLIC UREA COMPOUNDS

(75) Inventors: Xiaoling Chen, Chestnut Hill, MA (US); Srinivasa R. Karra, Pembroke, MA (US); Bayard R. Huck, Sudbury, MA (US); Ruoxi Lan, Waltham, MA (US); Amanda E. Sutton, Hingham, MA (US); Andreas Goutopoulos, Boston, MA (US); Brian L. Hodous, Cambridge, MA (US); Reinaldo Jones, Lowell, MA (US)

(73) Assignee: Merck Patent GmbH, Frankfurter (DE)

( * ) Notice: Subject to any disclaimer, the term of this patent is extended or adjusted under 35 U.S.C. 154(b) by 0 days.

(21) Appl. No.: 13/388,952

(22) PCT Filed: Jul. 28, 2010

(86) PCT No.: PCT/US2010/043467
§ 371 (c)(1),
(2), (4) Date: Mar. 22, 2012

(87) PCT Pub. No.: WO2011/017142
PCT Pub. Date: Feb. 10, 2011

(65) Prior Publication Data
US 2012/0190654 A1 Jul. 26, 2012

Related U.S. Application Data

(60) Provisional application No. 61/231,873, filed on Aug. 6, 2009.

(51) Int. Cl.
C07D 471/04 (2006.01)
C07D 498/14 (2006.01)
A61K 31/519 (2006.01)

(52) U.S. Cl.
USPC .................. 514/230.5; 514/261.1; 514/264.1; 544/95; 544/250; 544/251; 544/279

(58) Field of Classification Search
USPC ......... 544/95, 250, 251, 279; 514/230.5, 261, 514/264.1
See application file for complete search history.

(56) References Cited

FOREIGN PATENT DOCUMENTS

WO    WO 2006094347    *  9/2006
WO    2006/127587 A1    11/2006

OTHER PUBLICATIONS

Sausville, Edward, A., "Aurora Kinases dawn as cancer drug targets", Nature Medicine, Mar. 2004, pp. 234-235, vol. 10, No. 3.
Zhang, Yihong, et al., "Identification of a Novel Recepteur d"Origine Nanais/c-Met Small-Molecule Kinase Inhibitor with Antitumor Activity in vivo", Cancer Research, 2008, pp. 6680-6687, vol. 68, No. 16.
Fancelli, D., et al., "Inhibitors of Aurora kinases for the treatment of cancer", Expert Opinion on Therapeutic Patents, Sep. 1, 2005, vol. 15, pp. 1169-1182, vol. 15, No. 9.
Bishop, J.D., et al., "Phosphorylation of the Carboxyl Terminus of Inner Centromere Protein (INCENP) by the Aurora B Kinase Stimulates Aurora B Kinase Activity", The Journal of Biological Chemistry, Aug. 2, 2002, pp. 27577-27580, vol. 277, No. 31.
Ditchfield, Claire, et al., "Aurora B couples chromosome alignment with anaphase by targeting BubR1, Mad2, and Cenp-E to kinetochores", Journal of Cell Biology, Apr. 28, 2003, pp. 267-280, vol. 161, No. 2.
Emanuel, S., et al., "The In vitro and In vivo Effects of JNJ-7706621: A Dual Inhibitor of Cyclin-Dependent Kinases and Aurora Kinases", Cancer Research, Oct. 1, 2005, pp. 9038-9046, vol. 65, No. 19.
Hauf, Silke et al., "The small molecule Hesperadin reveals a role for Aurora B in correcting kinetochore—microtubule attachment and in maintaining the spindle assembly checkpoint", Journal of Cell Biology, Apr. 28, 2003, pp. 281-294, vol. 161, No. 2.
Harrington, Elizabeth, et al., "VX-680, a potent and selective small-molecule inhibitor of the Aurora kinases, suppresses tumor growth in vivo", Nature Medicine, Mar. 2004, pp. 262-267. vol. 10, No. 3.
Marumoto, Tomotoshi, et al., "Aurora-A—A Guardian of Poles", Nature Reviews: Cancer, Jan. 2005, pp. 42-50, vol. 5.
Minoshima, Yukinori, et al., "Phosphorylation by Aurora B Converts MgcRacGap to a RhoGAP during Cytokinesis", Developmental Cell, Apr. 2003, pp. 549-560, vol. 4.
Warner, Steven et al., "Molecular Cancer Therapeutics", Mol. Cancer Ther, 2003, pp. 589-595, vol. 2.

* cited by examiner

*Primary Examiner* — Bruck Kifle

(57) ABSTRACT

The invention provides novel substituted azaheterocyclic compounds according to Formula (I), their manufacture and use for the treatment of hyperproliferative diseases, such as cancer.

60 Claims, No Drawings

BICYCLIC UREA COMPOUNDS

FIELD OF THE INVENTION

The invention relates to a series of substituted bicyclic urea compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases represent a large family of proteins, which play a central role in the regulation of a wide variety of cellular processes, thus maintaining control over cellular function. A partial list of such kinases includes Akt, Axl, Aurora A, Aurora B, dyrk2, epha2, fgfr3, flt-3, vegfr3, igf1r, IKK2, JNK3, Vegfr2, MEK1, MET, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt3, Flt1, PDK1, Erk and RON. Inhibition of such kinases has become a strategy in treating many dreadful diseases.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds of the invention are novel, selective, and highly potent adenosine triphosphate (ATP) competitive inhibitors of Aurora kinases—hereinafter also referred to as AK—(A, B and C). The Aurora family of conserved serine/threonine kinases perform essential functions during cell division. The three mammalian paralogues are very similar in sequence, but differ significantly in their localization, function, substrates and regulatory partners. Aurora A is mainly associated with the spindle poles during mitosis, where it is required for centrosome separation and maturation (Sausville EA. AK dawn as cancer drug targets, *Nat. Med., (*2004) 10: 234-235 (2004). Spindle assembly requires that targeting protein for XKLP 2 (TPX2) targets Aurora A to spindle pole microtubules through a mechanism that requires Ran-GTP (Marumoto T, Zhang D, Saya H. Aurora A—A guardian of poles, Nature, (2005) 5 42-50 (2005). Aurora A also functions in meiosis promoting oocyte maturation, polar-body extrusion, spindle positioning and exit from metaphase I. Regulation of Aurora A occurs through phosphorylation/dephosphorylation and degradation. Protein phosphatase 1 negatively regulates Aurora and this interaction is modulated by TPX2. Aurora B is a chromosomal-passenger protein with multiple functions in mitosis. Inner centromere protein (INCENP) and survivin, two other components of the passenger complex, function as targeting and regulatory factors for the kinase (Bishop J D and Shumacher J M. Phosphorylation of the Carboxyl Terminus of Inner Centromere Protein (INCENP) by the aurora B Kinase Stimulates aurora B Kinase Activity, *J. Biol. Chem. (*2002) 277:27577-27580. Aurora B is required for phosphorylation of histone H3, targeting of condensin and normal chromosome compaction. It has also been recently shown to be essential for chromosome biorientation, kinetochore-microtubule interactions and the spindle-assembly checkpoint. Aurora B is essential for completion of cytokinesis. Myosin II regulatory chain, vimentin, desmin and glial fibrillary acidic protein are among its cleavage furrow substrates. Aurora B phosphorylates MgcRacGAP, transforming it into an activator of RhoA in the contractile ring (Minoshima Y, Kawashima T, Hirose K, Tonozuka Y, Kawajiri A, Bao Y, Deng X, Tatsuka M, Narumiya S, May W Phosphorylation by aurora B converts MgcRacGAP to a RhoGAP during cytokinesis. *Dev. Cell, (*2003) 4:549-560. Much less is known about Aurora C kinase, other than that it seems to be preferentially expressed in meiotic cells. During the cell cycle, Aurora kinases travel to their subcellular targets aided by their binding partner-substrates, INCENP, survivin and TPX2. This provides an additional level of regulation that might be essential for the choreography of mitotic events.

Aurora A and B kinases are frequently elevated in human cancers making them attractive targets for therapeutic intervention. Small molecule inhibitors of AK have recently been reported, but their effect on cytokinesis has yet to be investigated in detail. For example a high selective and potent small-molecule inhibitor of AK, VX-680, blocks cell-cycle progression and induces apoptosis in a diverse range of human tumor types. This compound causes profound inhibition of tumor growth in a variety of in vivo xenograft models, leading to regression of leukemia, colon and pancreatic tumors at well-tolerated doses (Harrington E A, Bebbington D, Moore J, Rasmussen R K, Ajose-Adeogun A O, Nakayama T. Graham J A, Demur C, Hercend T, Diu-Hercend A, Su M, Golec J M, Miller K M VX-680, a potent and selective small-molecule inhibitor of the aurora kinases, suppresses tumor growth in vivo, *Nat. Med., (*2004) 10:262-267. Another novel cell cycle inhibitor, JNJ-7706621, showed potent inhibition of several cyclin-dependent kinases (CDK) and Aurora kinases and selectively blocked proliferation of tumor cells of various origins, but was about 10-fold less effective at inhibiting normal human cell growth in vitro. In human cancer cells, treatment with JNJ-7706621 inhibited cell growth independent of p53, retinoblastoma, or P-glycoprotein status; activated apoptosis; and reduced colony formation. At low concentrations, JNJ-7706621 slowed the growth of cells and at higher concentrations induced cytotoxicity. Inhibition of CDK1 kinase activity, altered CDK1 phosphorylation status, and interference with downstream substrates such as retinoblastoma were also shown in human tumor cells following drug treatment. JNJ-7706621 delayed progression through G1 and arrested the cell cycle at the G2-M phase (Emanuel S, Rugg C A, Gruninger R H, Lin R, Fuentes-Pesquera A, Connolly P J, Wetter S K, Hollister B, Kruger W W, Napier C, Jolliffe L, Middleton S A, The in vitro and in vivo effects of JNJ-7706621: A dual inhibitor of cyclin-dependent kinases and AK, *Cancer Res., (*2005) 65:9038-9046). Additional cellular effects due to inhibition of AK included endoreduplication and inhibition of histone H3 phosphorylation. In a human tumor xenograft model, several intermittent dosing schedules were identified that produced significant antitumor activity.

As noted above, AK are overexpressed in certain types of cancers, including colon, breast, and other solid-tumor cancers. The genes encoding the Aurora B and A kinases tend to be amplified in certain types of cancers, while the gene encoding the Aurora C kinase resides in a region of the chromosome that is subject to rearrangement and deletion. Aurora A has been associated with a variety of malignancies, including primary colon, colorectal, breast, stomach, ovarian, prostate, and cervical cancer, neuroblastoma, and other solid-tumor cancers (Warner et al. (2003) *Molecular Cancer Therapeutics* 2:589-95).

Hauf et al. (*J. Cell. Biol. (*2003) 161:281-294) identified the indolinone (Hesperadin) as an inhibitor of Aurora B, which causes cells to enter anaphase with monooriented chromosomes, having both sister kinetochores attached to a single spindle pole (a condition known as syntelic attachment).

Ditchfield et al. (J. Cell. Biol. (2003) 161:267-280) described ZM447439 ((4-(4-(N-benzoylamino)anilino)--6-methoxy-7-(3-(1-morpholino)propoxy) quinazoline), an AK inhibitor which interferes with chromosome alignment, segregation, and cytokinesis.

It has been found by the inventors of this patent application that the compounds of the invention also inhibit RON kinase.

"Recepteur d'origine nantais" (RON) is a receptor tyrosine kinase (RTK) normally expressed at low levels mostly on epithelial cells (Zhang et al., Cancer Res. 68(16), 2008, 6680-6687). It is closely related to c-Met in terms of homology and function. Both RON and c-Met are activated in response to their respective ligand: macrophage-stimulating protein (MSP) for RON and hepatocyte growth factor (HGF) for c-Met. The two RTKs induce an invasive program consisting of cell proliferation, migration, and invasion, all of which are important at multiple points during tumorigenesis. RON and c-Met elicit these functions through a unique docking site located at their COOH terminus. On receptor activation, two tyrosine residues at the COOH terminus become phosphorylated and form a multifunctional docking site for SH2 domain-containing adaptor proteins. This event subsequently triggers a complex signalling cascade that includes activation of the phosphatidylinositol 3-kinase and the mitogen-activated protein kinase (MAPK) pathways and results in the characteristic functional responses associated with RON and c-Met.

The oncogenic potential of RON and c-Met has been shown in vitro as well as in transgenic animals. Oncogene addiction refers to the dependence of tumor cell survival on an activated oncogene, such as BCR-ABL, in chronic myelogenous leukemia. This concept suggests that inhibition of the activated oncogene is sufficient to obtain a clinical response. This has been proven in the clinic with several kinase inhibitors, such as imatinib and gefitinib. In the case of kinases, oncogene addiction may stem from constitutive activity that can arise as a result of gene translocation, mutation, or amplification. c-Met and RON can be constitutively activated through ligand-independent mechanisms in tumor cells. Constitutively activated c-Met can result from gene amplification or activating mutations. The "oncogene addiction" to c-Met is exemplified by the recent identification of a subset of gastric cancer cell lines harboring MET gene amplification. These cells are dependent on c-Met for growth and survival and are sensitive to a c-Met inhibitor. Unlike c-Met, RON-activating mutations or gene amplification has not been described. Instead, constitutively active RON variants generated by alternative splicing or by methylation-dependent promoter usage [short form RON have been identified. Cells expressing these RON proteins show greater scatter activity, focus formation, anchorage-independent growth, and tumor formation in nude mice compared with cells expressing wild-type RON.

Therefore, RON kinase is a promising target for cancer therapies as well.

DESCRIPTION OF THE INVENTION

It is the object of the present invention to provide novel protein kinase inhibitors useful in the treatment of hyperproliferative diseases, especially those related to the hyperactivity of Aurora Kinase and RON kinase, such as cancer in mammals with superior pharmacological properties both with respect to their activities as well as their solubility, metabolic clearance and bioavailability characteristics.

As a result, this invention provides novel, substituted bicyclic urea compounds and pharmaceutically acceptable salts, solvates or prodrugs thereof, that are protein kinase inhibitors and useful in the treatment of the above mentioned diseases. The compounds are defined by Formula (I):

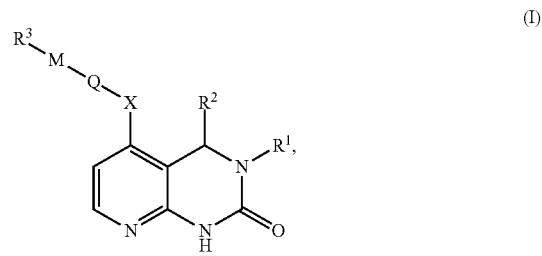

and pharmaceutically acceptable salts, solvates or prodrugs thereof,
wherein:
  X is a bond, NH, O, S, or $CH_2NH$ or $CH_2O$, wherein the NH or O moieties are connected to the 2-oxo-1,2,3,4-tetrahydropyrido[2,3-d]pyrimidine moiety,
  Q is a 5- or 6-membered monocyclic, or 9- or 10-membered bycyclic, aromatic, homo- or heterocycle having 1 or 2 N, O and/or S atoms, which may be unsubstituted or, independently of one another, mono- or disubstituted by Hal, LA, $C(Hal)_3$, $OC(Hal)_3$, OH, SH, O(LA), $NH_2$, NH(LA), $N(LA)_2$, $NO_2$, CN, OCN, 4-fluorophenyl, oxo or SCN,
  M is a bond, $CH_2$, CO, $SO_2$, CONH, NHCO, NHCONH, $SO_2NH$, $NHSO_2$, $NHSO_2NH$ or $CH_2NHCO$, wherein the CO moiety is connected to Q,
  $R^1$ is H, A, Ar or Ar-A,
  $R^2$ is H, or
  $R^1$ and $R^2$ together with the N and C atoms to which they are attached, may form a 5- or 6-membered aliphatic heterocycle having 1 or 2 N, O and/or S atoms, which may be unsubstituted or substituted by Hal, A, OH, $NH_2$ or CN,
  $R^3$ is A or Q, or
  $R^3$-M may be absent,
  Ar is a mono- or bicyclic aromatic homo- or heterocycle having 1 to 4 N, O and/or S atoms and 5 to 10 skeleton atoms, which may be unsubstituted or, independently of one another, mono-, di- or trisubstituted by Hal, A, OH, SH, OA, $NH_2$, NHA, $NA_2$, $NO_2$, CN, OCN, SCN, COOH, COOA, $CONH_2$, CONHA, CONH(LAr), $CONA_2$, NHCOA, NHCO(LAr), NHCONHA, $NHCONH_2$, $NHSO_2A$, CHO, COA, $SO_2NH_2$, $SO_2A$ and/or $SO_2Hal$,
  A is unbranched or branched, linear or cyclic alkyl having 1,2,3,4,5,6,7 or 8 C atoms, in which one or two $CH_2$ groups may be replaced by an O or S atom and/or by an NH, CO, N(LA), $SO_2$, CONH, NHCO or —CH=CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$, $N_3$, $NO_2$ or CN,
  LA is unbranched or branched, linear alkyl having 1,2,3 or 4 C atoms,
  Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

For the avoidance of any doubt as to the orientation of linkers M and X in the chain of substituents $R^3$-M-Q-X, this chain reads from left to right $R^3$-M-Q-X.

Hal denotes fluorine, chlorine, bromine or iodine, in particular fluorine or chlorine.

"A" denotes alkyl, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

"A" further denotes alkyl as defined above, in which one or two $CH_2$ groups may be replaced by O or S atoms and/or by NH, CO, NA, CONH, NHCO or —CH=CH-groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy. In other examples of "A", one or two $CH_3$ groups is replaced by OH, SH, $NH_2$, N(LA)H, N(LA)$_2$, $N_3$, $NO_2$, $CHal_3$ or CN, such as, for example, N,N'-dimethylaminoalkyl, 2-am inoethyl, 3-am inopropyl, 4-am inobutyl, 5-am inopentyl, 3-aminomethylcyclobutyl, cyanoalkyl or $CF_3$.

"A" may also be cyclic, wherein the cyclic moiety can be substituted by, or incorporated in an otherwise non-cyclic structure. Examples for cyclic "A" include 2- or 3-furyl, 2,3-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 2-, 3-, 5- or 6-piperidin-1 or 4-yl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoro-methylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl, indan-1-, 2-, 4- or 5-yl, 1,2,3,4-tetrahydro-naphthalenyl, tetrahydrofuran-2- or 3-yl, 2-oxo-1,2-dihydropyridin-1-, 3-, 4-, 5- or 6-yl, or 2,3-dihydro-2-oxofuranyl, each of which is unsubstituted or may be mono-, di- or trisubstituted, for example, by carbonyl oxygen, F, Cl, Br, methyl, ethyl, propyl, —$CH_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

"LA" denotes unbranched or branched, linear alkyl having 1,2,3 or 4 C atoms, i.e. methyl, ethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoro-methyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methyl-amino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p- chlorophenyl, o-, m- or p-(methyl-sulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxy-phenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-tri-chlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3, 4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6,-or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or -5-yl or 2,1,3-benzoxadiazol-5-yl, furan-2- or 3-yl, 2,3-dihydro-benzofuran-2-, 3-, 4- or 5-yl, each of which is unsubstituted or may be mono-, di- or trisubstituted, for example, by F, Cl, Br, methyl, ethyl, propyl, phenyl, benzyl, -$CH_2$-cyclohexyl, hydroxyl, methoxy, ethoxy, amino, methylamino, dimethylamino, nitro, cyano, carboxyl, methoxycarbonyl, amino-carbonyl, methylaminocarbonyl, dimethylaminocarbonyl, acetamino, ureido, methyl-sulfonylamino, formyl, acetyl, aminosulfonyl and/or methylsulfonyl.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the Formula (I) may have one or more centres of chirality. They may, accordingly, occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

A preferred group of compounds of Formula (I) conforms to Formula (II),

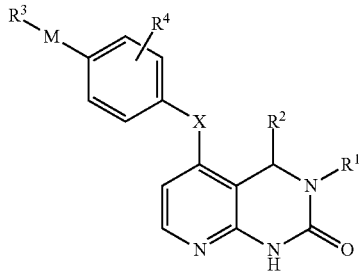

and pharmaceutically acceptable salts, solvates or prodrugs thereof,
wherein:
$R^3$ is phenyl, pyridyl or 2-oxo-1,2-dihydropyridinyl, each of which is unsubstituted, or substituted by $R^4$,
$R^4$ is H, Hal or A, and the remaining substituents have the meaning indicated for Formula (I) above.

Another preferred group of compounds of Formula (I) conforms to Formulae (III), (IV), (V), (VI), (VII) or (VIII),

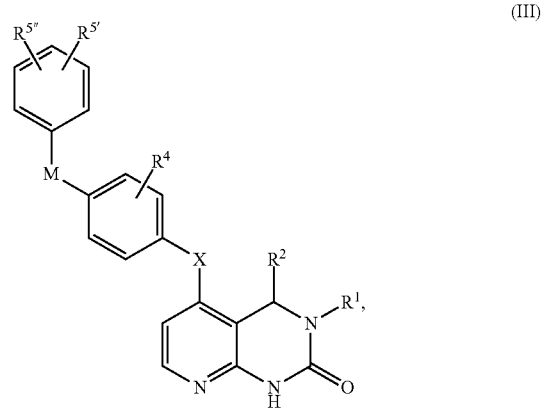

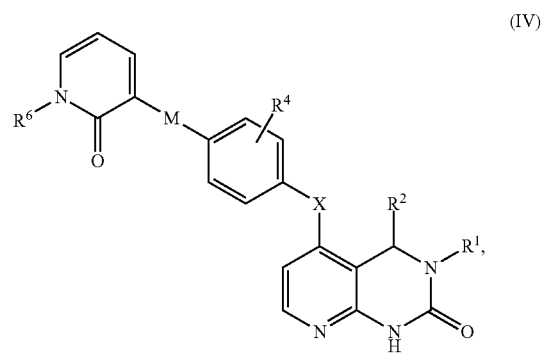

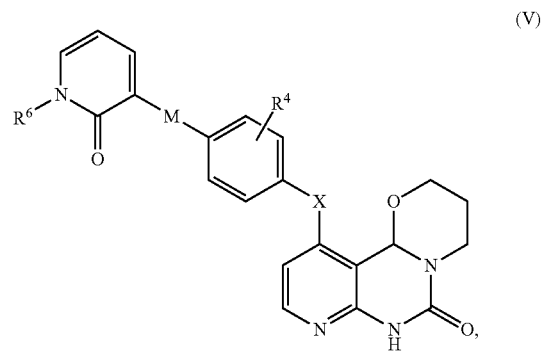

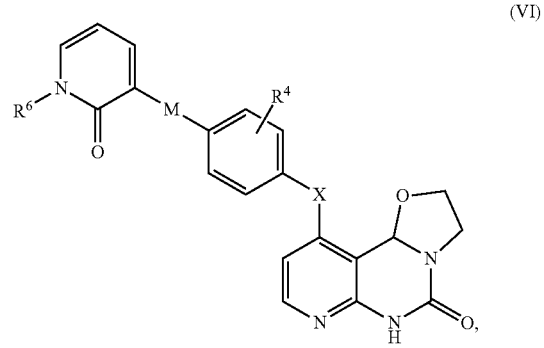

-continued

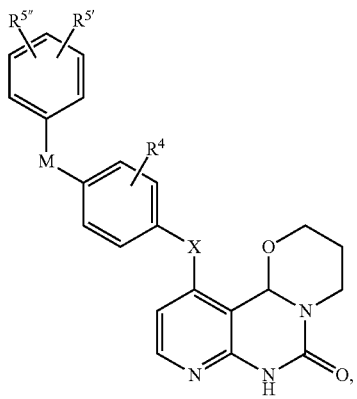
(VII)

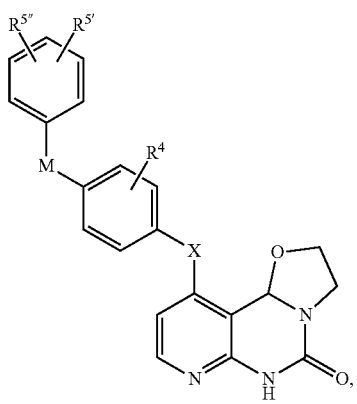
(VIII)

and pharmaceutically acceptable salts, solvates or prodrugs thereof,
wherein:
$R^4$, $R^{5'}$, $R^{5''}$ each, independently of one another, are H, Hal or A,
$R^6$ is H, A or Ar,
and the remaining substituents have the meaning indicated for Formula (I) above.

Even more preferred are compounds of Subformulae A, B, C, D, E, F, G, H, J, K, L, M, N, O and P of Formulae (III), (IV), (V), (VI), (VII) and (VIII), and pharmaceutically acceptable salts, solvates or prodrugs thereof, wherein
in Subformula A
X is NH,
and the remaining residues have the meaning as indicated for Formula (I) above,
in Subformula B
X is O,
and the remaining residues have the meaning as indicated for Formula (I) above,
in Subformula C
X is NH,
M is CONH,
and the remaining residues have the meaning as indicated for Formula (I) above,
in Subformula D
X is O,
M is CONH,
and the remaining residues have the meaning as indicated for Formula (I) above,
in Subformula E
$R^4$ is H or F,
$R^{5'}$, $R^{5''}$ each, independently of one another, are H, F, Br, CN, $CH_3$, $OCH_3$ or $CF_3$,
and the remaining residues have the meaning as indicated for Formula (I) above,
in Subformula F
M is NHCONH,
and the remaining residues have the meaning as indicated for Formula (I) above,
in Subformula G
$R^1$ is H,
and the remaining residues have the meaning as indicated for Formula (I) above,
in Subformula H
M is CONH,
and the remaining residues have the meaning as indicated for Formula (I) above,
in Subformula J
$R^1$ is H,
M is CONH,
and the remaining residues have the meaning as indicated for Formula (I) above,
in Subformula K
$R^1$ is A, Ar or Ar-A,
and the remaining residues have the meaning as indicated for Formula (I) above,
in Subformula L
$R^1$ is A, Ar or Ar-A,
M is CONH,
and the remaining residues have the meaning as indicated for Formula (I) above,
in Subformula M
$R^4$ is H or F,
$R^{5'}$, $R^{5''}$ each, independently of one another, are H, F or $CF_3$,
and the remaining residues have the meaning as indicated for Formula (I) above,
in Subformula N
$R^4$ is H or F,
$R^{5'}$ is 4-fluoro,
$R^{5''}$ is 2-(trifluoromethyl),
and the remaining residues have the meaning as indicated for Formula (I) above,
in Subformula O
$R^3$ is H, methyl, ethyl, 3-hydroxypropyl or 2,2,2-trifluoroethyl,
and the remaining residues have the meaning as indicated for Formula (I) above,
in Subformula P
$R^3$ is H, methyl or ethyl,
and the remaining residues have the meaning as indicated for Formula (I) above,
in Subformula Q
$R^1$ is ethyl,
and the remaining residues have the meaning as indicated for Formula (I) above.

In another preferred Subformula (Ia) of compounds of Formula (I) X is a bond, and the remaining residues have the meaning as indicated for Formula (I) above.

In more preferred Subformula (Ib) of these compounds X is a bond, Q is thienyl, and the remaining residues have the meaning as indicated for Formula (I) above.

In an even more preferred Subformula (Ic) of these compounds, X is a bond, Q is thienyl, M is $CH_2NHCO$, wherein the CO moiety is connected to Q, and the remaining residues have the meaning as indicated for Formula (I) above.

Especially preferred compounds according to Formula (I), (II), (III), (IV), (V), (VI), (VII) or (VIII) include the compounds shown in the examples section below, or the pharmaceutically acceptable salts, solvates or prodrugs each thereof.

For the AK A or RON kinase inhibition the following classification is used:
$IC_{50}$<10 nM "+++"
10 nM≤$IC_{50}$<100 nM "++"
100 nM≤$IC_{50}$<1 μM "+"

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other protein kinase inhibitors, particularly AK or RON.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for use in the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast cancer, in particular the basal-like or triple negative types of breast cancer, colorectal, lung, prostate or pancreatic cancer or glioblastoma.

The invention also relates to the use of compounds according to the invention for the preparation of a medicament for the treatment of hyperproliferative diseases related to the hyperactivity of protein kinases as well as diseases modulated by protein kinase cascades in mammals, or disorders mediated by aberrant proliferation, such as cancer and inflammation.

The invention also relates to a compound or pharmaceutical composition for use in the treatment of a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for use in the treatment of a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity and age-related macular degeneration.

This invention also relates to a compound or pharmaceutical composition for use in the treatment of cancer in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, p70S6K, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal, or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Some abbreviations that may appear in this application are as follows:
Abbreviations

| Designation | |
|---|---|
| AcOH | Acetic acid |
| ATP | Adenosine triphosphate |
| B | Broad peak |
| Bop—Cl | Bis(2-oxo-3-oxazolidinyl)phosphonic chloride |
| Boc | Butyloxycarbonyl |
| Bu | Butyl |
| CDI | N,N-Carbonyldiimidazole |
| d | Doublet |
| DCE | 1,2-dichloroethane |
| DCM | Dichloromethane |
| dd | Doublet of doublets |
| DIEA | Diisopropylethyl amine |
| DMF | N,N-Dimethylformamide |
| DMSO | Dimethylsulfoxide |
| DTT | Dithiothreitol |
| Et | Ethyl |
| EtOAc | Acetic acid ethyl ester |
| h | Hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| m | Multiplet |
| M | Molecular ion |
| m/z | Mass-to-charge ratio |
| Me | Methyl |
| min | Minute |
| MS | Mass spectrometry |
| N | Normal (unit of concentration) |
| nBuLi | n-Butyllithium |
| NMP | N-Methyl-2-pyrrolidone |
| NMR | Nuclear Magnetic Resonance |
| obsd. | Observed |
| psi | Pounds per square inch |
| q | Quartette (or quartet) |
| Rf | Retention factor |
| rt | Room temperature |
| s | Singlet |
| t | Tertiary |
| TEA | Triethyl amine |
| Tert | Tertiary |
| TFA | Trifluoroacetic acid |
| THF | Tetrahydrofuran |
| UV | Ultraviolet |
| VIS | Visible |
| X-Phos | 2-Dicyclohexylphosphino-2',4',6'-triisopropylbiphenyl |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formulae (I)-(VIII) and Subformulae A-P thereof, according to the hereinafter described schemes and working examples.

General Synthetic Procedures

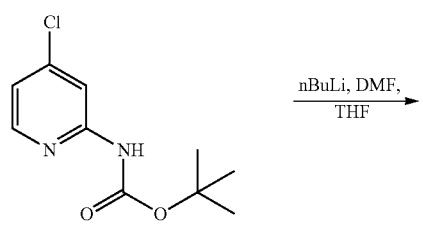

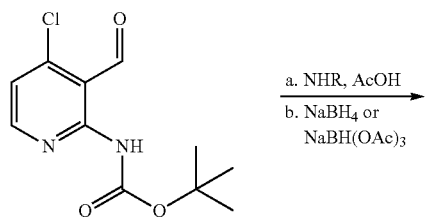

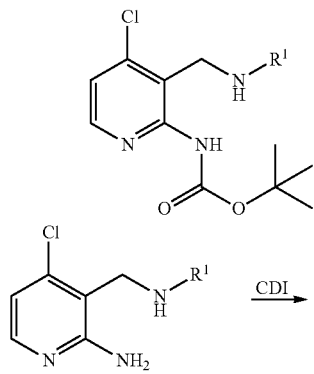

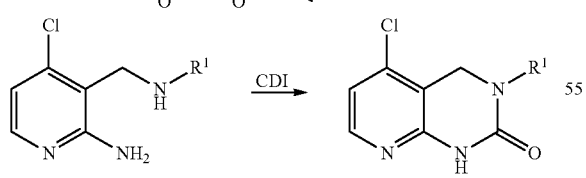

Scheme 1: The pyridine starting material starting material is reacted with nBuLi to form an anion, which is quenched with DMF to provide the aldehyde intermediate. A reductive amination is performed with the aldehyde and an amine which provides an amine intermediate. Subsequent Boc deprotection provides a diamine, which can be converted to the desired urea scaffold upon reaction with CDI.

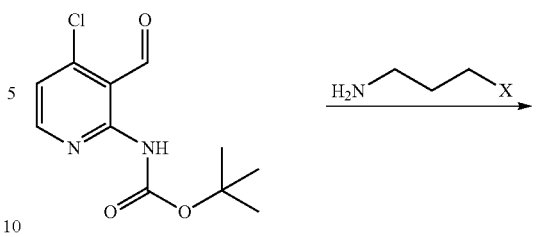

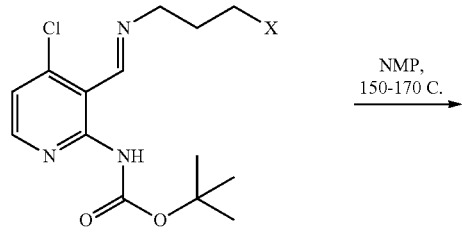

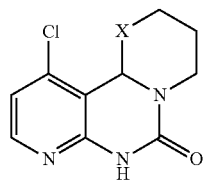

Scheme 2: The same aldehyde intermediate as in Scheme 1 can be combined with an amine to form an imine. A nucleophile (X) on the imine intermediate can attack the imine to provide a heterocycle. The resulting heterocycle can be heated in NMP to provide the desired tricyclic ureas scaffold.

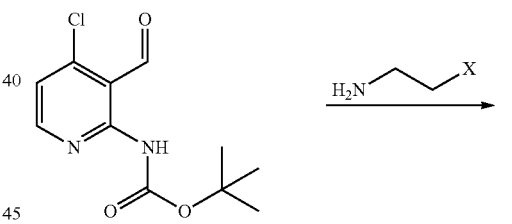

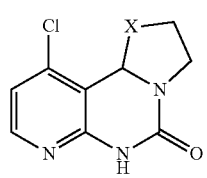

Scheme 3: The same aldehyde intermediate as in Scheme 1 can be combined with an amine to form an imine. A nucleophile (X) on the imine intermediate can attack the imine to provide a heterocycle. The resulting heterocycle can be heated in NMP to provide the desired tricyclic ureas scaffold.

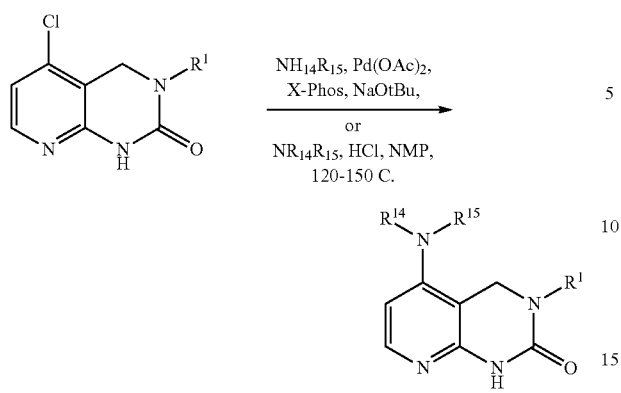

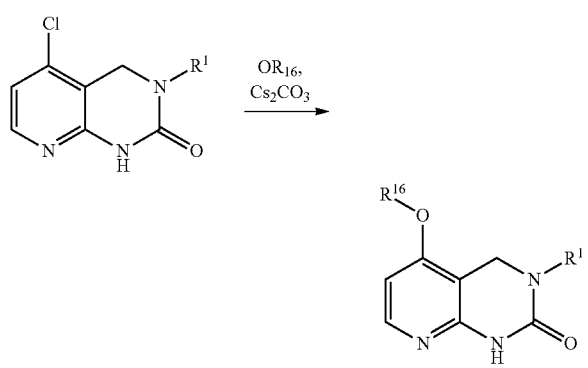

Scheme 4: The suitably functionalized urea scaffold can be reacted with an amine via a metal-mediated cross coupling or an acid catalyzed cross coupling to provide a bicyclic scaffold with a amine moiety.

Scheme 5: An ether moiety can be introduced to the scaffold via an aromatic nucleophilic substitution reaction with a suitably functionalized urea scaffold.

Scheme 6: The aniline can be converted to the desired amide through reaction with an acid chloride or via carboxylic acid/coupling agent amide conditions.

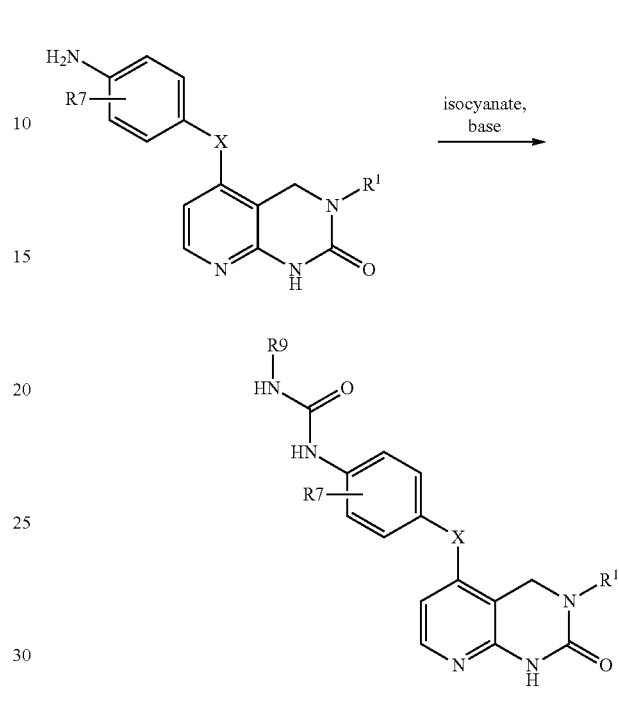

Scheme 7: The aniline can be converted to the desired urea through reaction with an isocyanate under basic conditions.

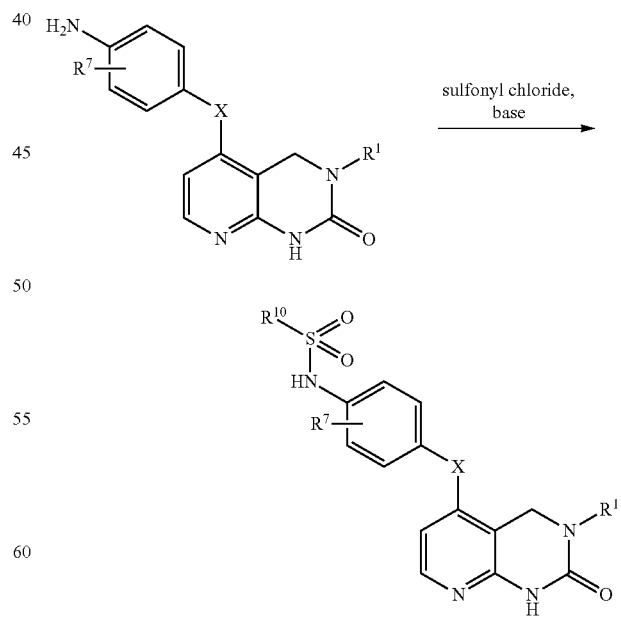

Scheme 8: The aniline can be converted to the desired sulfonamide through reaction with a sulfonyl chloride under basic conditions.

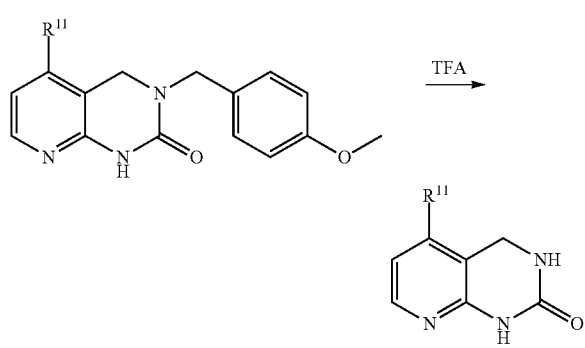

Scheme 9: The para-methoxy benzyl protecting group can be removed under acidic reaction conditions with TFA.

Analytical Methodology

LC-MS data were obtained using an Agilent 1100 HPLC system

Column: Waters, Xterra MS C18, 2.5 pm, 2.1 mm x 20 mm.

Mobile phase: A: 0.1% Formic acid in Water

B: 0.1% Formic acid in Methanol

Gradient: Increase 15% B to 95% B in 3.2 min and hold for 1.4 min.

Decrease 95%B to 15% B for 0.1 min and hold for 2.3 min.

Run time: 7 min

Flow rate: 0.4 ml/min

Injection Volume: User defined

UV: 254 nm, followed by mass spectrometry on a Finnigan LCQ Duo system (type of ionisation: ESI, positive mode (analysing positively charged analytes)).

Proton magnetic resonance ($^1$H NMR) spectra were recorded on JEOL Eclipse 400 MHz ($^1$ H) NMR spectrometer. All spectra were determined in the solvents indicated. Although chemical shifts are reported in ppm downfield of tetramethylsilane, they are referenced to the residual proton peak of the respective solvent peak for 1H NMR. Interproton coupling contants are reported in Hertz (Hz).

EXAMPLES

Chemical Synthesis

The examples presented below are intended to illustrate particular embodiments of the invention, and are not intended to limit the scope of the specification or the claims in any way.

All temperatures are given in degrees Centigrade. Reagents were purchased from commercial sources or prepared following literature procedures.

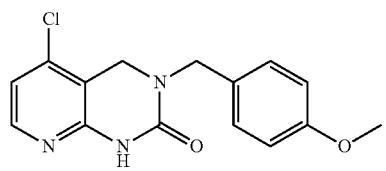 [SMILES: COc1ccc(CN2Cc3c(Cl)ccnc3NC2=O)cc1]

5-chloro-3-(4-methoxybenzyl)-3,4-dihydropyrido [2,3-d] pyrimidin-2 (1 H)-one (1)

Tert-butyl 4-chloro-3-formylpyridin-2-ylcarbamate

A solution of tert-butyl (4-chloropyridin-2-yl) carbamate (15.0 g, 65.59 mmol) in THF (300 mL) was cooled to −78 °C.

To this stirred solution was added dropwise nBuLi (55.1 mL; 2.50 M; 137.7 mmol) over 20 min. The resulting light yellow reaction solution was stirred at −78 ° C. for 30 min. Then DMF (15.1 mL, 196.8 mmol) was added dropwise over 5 min. The reaction mixture was stirred for 1 h at −78 ° C. The reaction was quenched with MeOH (2 equivalents), and then conc. HCl (16 ml) was added. The resulting mixture was concentrated. The residue was suspended in EtOAc, washed with 5% $NaHCO_3$, and brine, and evaporated. The crude material was suspended in hexane (100 mL). The resulting precipitate was filtered to provide the desired intermediate (12.8 g, 76% yield) as a white solid.

Tert-butyl 4-chloro-3-((4-methoxybenzylamino) methyl) pyridin-2-ylcarbamate tert-Butyl (4-chloro-3-formylpyridin-2-yl) carbamate (300 mg, 1.56 mmol),1-(4-methoxyphenyl) methylamine (0.25 mL, 1.95 mmol), AcOH (1 eq), and $NaBH(OAc)_3$ were suspended in DCE, and the reaction mixture was stirred overnight at room temperature. The reaction was quenched with satd. aqueous $NaHCO_3$, and extracted with EtOAc. The organic extracts were dried over $MgSO_4$, filtered, and concentrated to provide the desired intermediate (440 mg), which was used directly in the next reaction.

4-chloro-3-((4-methoxybenzylamino)methyl)pyridin-2-amine

TFA (5 mL) was added to a solution of tert-butyl 4-chloro-3-((4-methoxybenzylamino)methyl) pyridin-2-ylcarbamate (440 mg, 1.56 mmol) in DCM (5 mL), and stirred overnight at room temperature. The reaction mixture was concentrated to provide the desired intermediate (350 mg), which was used directly in the next reaction.

5-chloro-3-(4-methoxybenzyl)-3,4-dihydropyrido [2,3-d] pyrimidin-2 (1H)-one (1)

CDI (583 mg, 3.56 mmol) was added to a solution of 4-chloro-3-((4-methoxybenzylamino)methyl) pyridin-2-amine (100 mg, 1.19 mmol) in acetonitrile (5 mL), and stirred for 1 h at room temperature. The resulting precipitate was filtered, and washed with $H_2O$ and MeOH, to provide 1 as a solid. LC-MS (M+H=303, obsd.=303. $^1$H NMR: (DMSO-D6) δ 3.74 (s, 3H); 4.34 (s, 2H); 4.52(s, 2H); 6.92 (d, 2H); 7.03 (d, 1H); 7.26 (d, 2H); 8.03 (d, 1H); 10.08 (s, 1H).

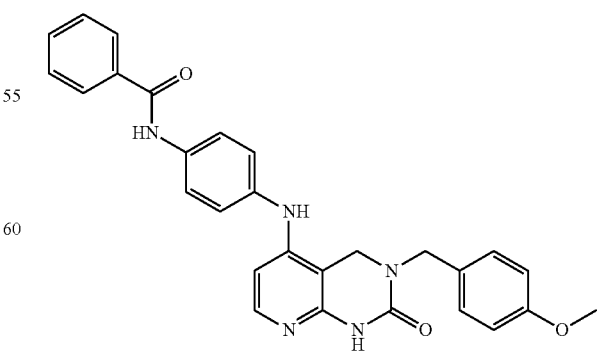

$IC_{50}$ (AK) "+"

N-(4-(3-(4-methoxybenzyl-2-oxo-1,2,3,4-tetrahydropyrido[2,3-d] pyrimidin-5-ylamino) phenyl) benzamide (2)

1 (50 mg, 0.16 mmol), N-(4-aminophenyl) benzamide (35 mg, 0.16 mmol), and 4.0M HCI in dioxane (40 μmL, 0.16mmol) were combined in a 5 mL seal tube. The tube was placed in the microwave for 100 min at 150° C. The reaction mixture was diluted EtOAc (30 mL), washed with 5% NaHCO$_3$ (10 mL), and brine (10 mL). The organic extracts were dried over MgSO$_4$, filtered, and concentrated. The crude material was purified via silica gel chromatography with a gradient of 2 to 8% MeOH in DCM/TEA (99.5/0.5) to provide 2 (10 mg) as a solid. LC-MS (M+H=480, obsd.=480).$^1$H NMR: (DMSO-D6) δ 3.74 (s, 3H); 4.27 (s, 2H); 4.50(s, 2H); 6.44 (d, 1H); 6.94 (d, 2H); 7.14 (d, 2H); 7.27 (d, 2H); 7.54 (m, 3H), 7.75 (m, 3H), 7.93-7.96(m, 4H), 9.48 (s, 1H).

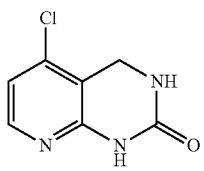 [SMILES: O=C1NCc2c(Cl)ccnc2N1]

5-chloro-3,4-dihydropyrido [2,3-d] pyrimidin-2 (1H)-one (3)

1 (90 mg, 0.3 mmol) and TFA (2 mL) were added to a 5 mL sealed tube, and stirred overnight at 80° C. The TFA was removed, and the material was suspended in ether. The resulting precipitate was filtered to provide 3 (56 mg, 99% yield). LC-MS (M+H=184, obsd.=184). $^1$H NMR: (DMSO-D6) δ 4.37 (s, 2H); 7.03(d, 2H); 7.13 (s, 1H); 8.02 (d, 1H); 9.77 (s, 1H).

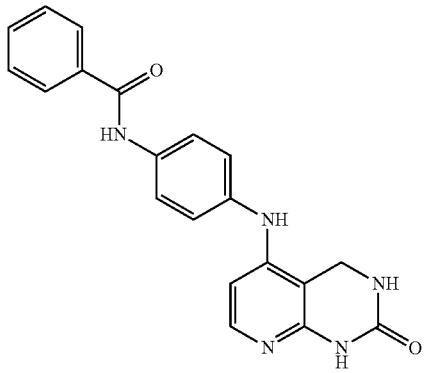 [SMILES: O=C1NCc2c(Nc3ccc(NC(=O)c4ccccc4)cc3)ccnc2N1]

IC$_{50}$ (AK) "++"

N-(4-(2-oxo-1,2,3,4-tetrahydropyrido [2,3-d] pyrimidin-5-ylamino)phenyl)benzamide (4)

The title compound was synthesized according to the procedure described for the preparation of Example 3 using 2. LC-MS (M+H=360, obsd.=360).

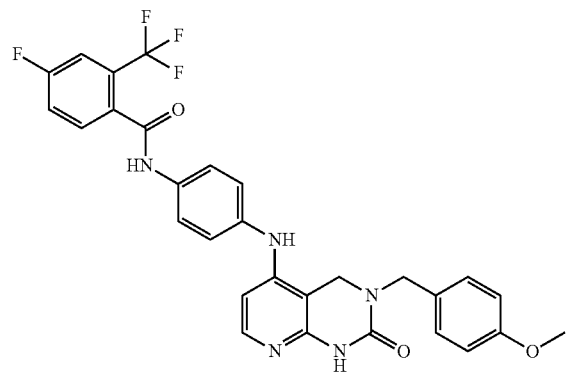 [SMILES: COc1ccc(CN2Cc3c(Nc4ccc(NC(=O)c5ccc(F)cc5C(F)(F)F)cc4)ccnc3NC2=O)cc1]

IC50 (AK) "+"

4-fluoro-N-(4-(3-(4-methoxybenzyl)-2-oxo-1,2,3,4-tetrahydropyrido [2,3-d] pyrimidin-5-ylamino)phenyl)-2-(trifluoromethyl) benzamide (5)

The title compound was synthesized according to the procedure described for the preparation of Example 2 using 1 and N-(4-amino-phenyl)-4-fluoro-2-trifluoromethyl-benzamide. LC-MS (M+H=566, obsd.=566).

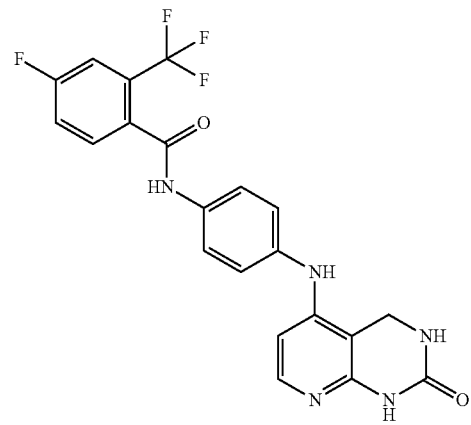 [SMILES: O=C1NCc2c(Nc3ccc(NC(=O)c4ccc(F)cc4C(F)(F)F)cc3)ccnc2N1]

IC50 (AK) "+++"

4-fluoro-N-(4-(2-oxo-1,2,3,4-tetrahydropyrido[2,3-d]pyrimidin-5-ylamino)phenyl)-2-(trifluoromethyl) benzamide (6)

The title compound was synthesized according to the procedure described for the preparation of Example 3 using 5. LC-MS (M+H=446, obsd.=446).

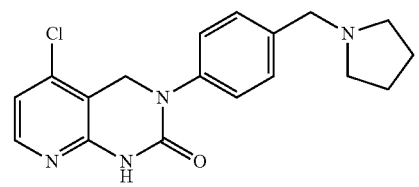 [SMILES: O=C1Nc2nccc(Cl)c2CN1c1ccc(CN2CCCC2)cc1]

5-chloro-3-(4-(pyrrolidin-1-ylmethyl)phenyl)-3,4-dihydropyrido[2,3-d]pyrimidin-2(1H)-one (7)

The title compound was synthesized according to the procedure described for the preparation of Example 1 using 4-pyrrolidin-1-ylmethyl-phenylamine. LC-MS (M+H=343, obsd.=343). 1H NMR (DMSO-D6) δ 1.85-1.87 (m, 2H); 2.04 (m, 2H); 3.12-3.14 (m, 2H); 4.39 (d, 2H); 4.90 (s, 2H); 7.14 (m, 1H); 7.41-1.42(m, 1H), 7.52-5.53(m, 2H); 7.55-5.56 (m, 1H), 9.77 (s, 1H), 10.44 (s, 1H).

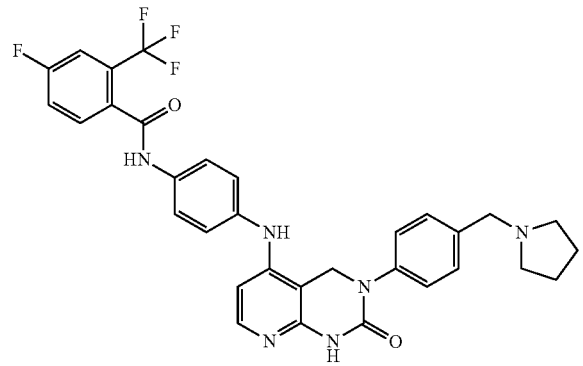 [SMILES: O=C(Nc1ccc(Nc2ccnc3c2CN(c2ccc(CN4CCCC4)cc2)C(=O)N3)cc1)c1ccc(F)cc1C(F)(F)F]

IC$_{50}$ (AK) "+"

4-fluoro-N-(4-(2-oxo-3-(4-(pyrrolidin-1-ylmethyl)phenyl)-1,2,3,4-tetrahydropyrido[2,3-d]pyrimidin-5-ylamino)phenyl)-2-(trifluoromethyl)benzamide (8)

The title compound was synthesized according to the procedure described for the preparation of Example 2 using 7 and N-(4-amino-phenyl)-4-fluoro-2-trifluoromethyl-benzamide. LC-MS (M+H=605, obsd.=605).

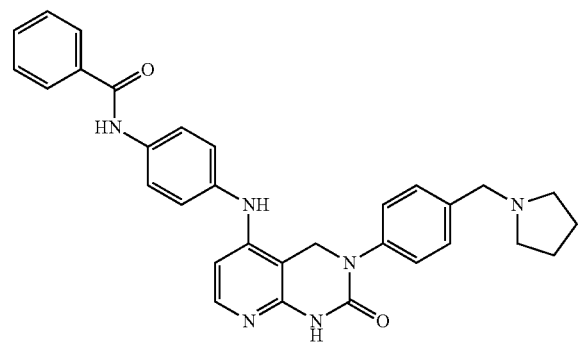 [SMILES: O=C(Nc1ccc(Nc2ccnc3c2CN(c2ccc(CN4CCCC4)cc2)C(=O)N3)cc1)c1ccccc1]

IC$_{50}$ (AK) "+"

N-(4-(2-oxo-3-(4-(pyrrolidin-1-ylmethyl)phenyl)-1,2,3,4-tetrahydropyrido[2,3-d]pyrimidin-5-ylamino)phenyl)benzamide (9)

The title compound was synthesized according to the procedure described for the preparation of Example 2 using 7 and N-(4-aminophenyl)benzamide. LC-MS (M+H=519, obsd.=519).

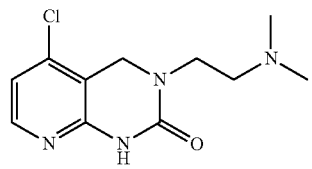 [SMILES: CN(C)CCN1Cc2c(Cl)ccnc2NC1=O]

5-chloro-3-(2-(dimethylamino) ethyl)-3,4-dihydropyrido [2,3-d] pyrimidin-2 (1 H)-one (10)

The title compound was synthesized according to the procedure described for the preparation of Example 1 using N*1*,N*1*-dimethyl-ethane-1,2-diamine. LC-MS (M+H=255, obsd.=255). $^1$H NMR: (DMSO-D6) δ 2.62 (s, 6H); 3.06 (t, 2H); 3.68 (t, 2H); 4.56 (s, 2H); 7.06 (s, 1H), 8.05 (d, 1H), 10.08 (s, 1H).

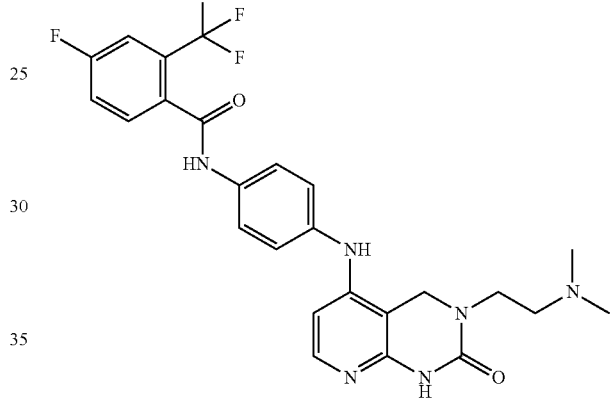

IC$_{50}$ (AK) "+"

N-(4-(3-(2-(dimethylamino) ethyl)-2-oxo-1,2,3,4-tetrahydropyrido [2,3-d] pyrimidin-5-ylamino) phenyl)-4-fluoro-2-(trifluoromethyl) benzamide (11)

The title compound was synthesized according to the procedure described for the preparation of Example 2 using 10 and N-(4-amino-phenyl)-4-fluoro-2-trifluoromethyl-benzamide. LC-MS (M+H=517, obsd.=517).

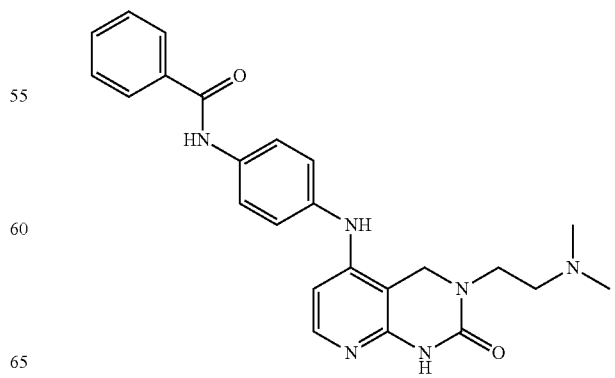

N-(4-(3-(2-(dimethylamino) ethyl)-2-oxo-1,2,3,4-tetrahydropyrido [2,3-d] pyrimidin-5-ylamino) phenyl) benzamide (12)

The title compound was synthesized according to the procedure described for the preparation of Example 2 using 10 and N-(4-aminophenyl) benzamide. LC-MS (M+H=431, obsd.=431).

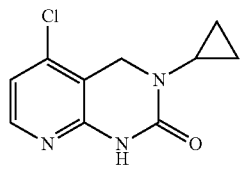 [SMILES: O=C1Nc2nccc(Cl)c2CN1C1CC1]

5-chloro-3-cyclopropyl-3,4-dihydropyrido [2,3-d] pyrimidin-2 (1H)-on (13)

The title compound was synthesized according to the procedure described for the preparation of Example 1 using cyclopropylamine. LC-MS (M+H=224, obsd.=224). $^1$HNMR: (DMSO-D6) δ 0.63 (d, 2H); 0.74 (d, 2H); 2.51(m, 1H); 4.43 (s,2H); 7.04 (m, 1H); 8.02 (m, 1H); 7.17 (s, 1H).

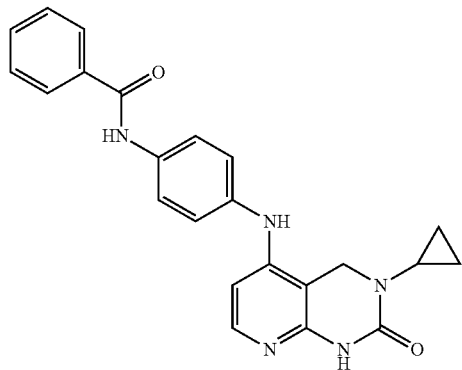 [SMILES: O=C(Nc1ccc(Nc2ccnc3c2CN(C2CC2)C(=O)N3)cc1)c1ccccc1]

IC$_{50}$ (AK) "+"

N-(4-(3-cyclopropyl-2-oxo-1,2,3,4-tetrahydropyrido [2,3-d] pyrimidin-5-ylamino) phenyl) benzamide (14)

The title compound was synthesized according to the procedure described for the preparation of Example 2 using 13 and N-(4-aminophenyl) benzamide. LC-MS (M+H=400, obsd.=400).

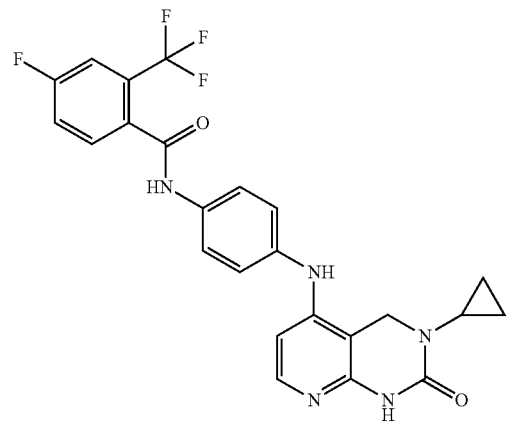 [SMILES: O=C(Nc1ccc(Nc2ccnc3c2CN(C2CC2)C(=O)N3)cc1)c1ccc(F)cc1C(F)(F)F]

IC$_{50}$ (AK) "++"

N-(4-(3-cyclopropyl-2-oxo-1,2,3,4-tetrahydropyrido [2,3-d] pyrimidin-5-ylamino) phenyl)-4-fluoro-2-(trifluoromethyl) benzamide (15)

The title compound was synthesized according to the procedure described for the preparation of Example 2 using 13 and N-(4-amino-phenyl)-4-fluoro-2-trifluoromethyl-benzamide. LC-MS (M+H=486, obsd.=486).

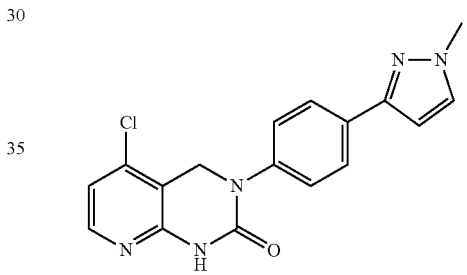

5-chloro-3-(1-methyl-1H-pyrazol-3-yl)-3,4-dihydropyrido [2,3-d] pyrimidin-2 (1 H)-one (16)

The title compound was synthesized according to the procedure described for the preparation of Example 1 using 4-(1-methyl-1H-pyrazol-3-yl)-phenylamine. LC-MS (M+H=264, obsd.=264).

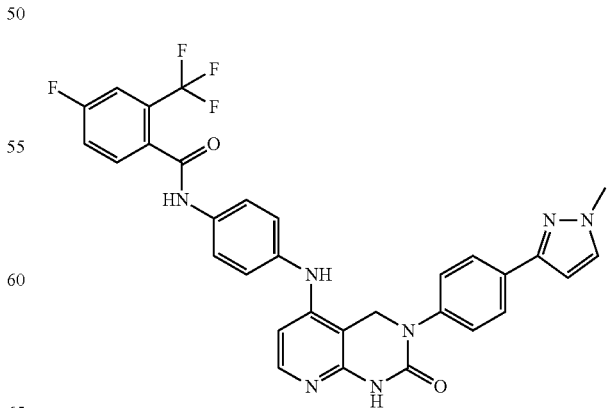

IC$_{50}$ (AK) "++"

4-fluoro-N-(4-(3-(1-methyl-1H-pyrazol-3-yl)-2-oxo-1,2,3,4-tetrahydropyrido[2,3-d]pyrimidin-5-ylamino)phenyl)-2-(trifluoromethyl)benzamide (17)

The title compound was synthesized according to the procedure described for the preparation of Example 2 using 16 and N-(4-amino-phenyl)-4-fluoro-2-trifluoromethyl-benzamide. LC-MS (M+H=526, obsd.=526).

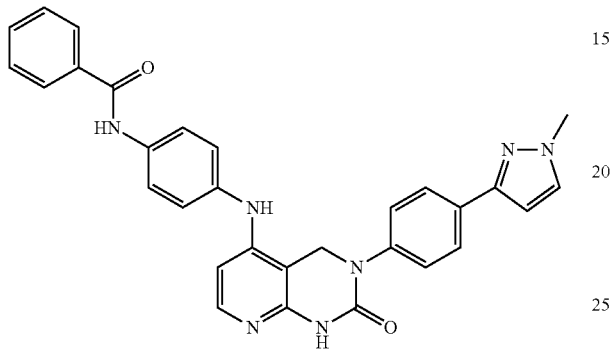

IC$_{50}$ (AK) "++"

N-(4-(3-(1-methyl-1H-pyrazol-3-yl)-2-oxo-1,2,3,4-tetrahydropyrido [2,3-d] pyrimidin-5-ylamino) phenyl) benzamide (18)

The title compound was synthesized according to the procedure described for the preparation of Example 2 using 16 and N-(4-aminophenyl) benzamide. LC-MS (M+H=440, obsd.=440).

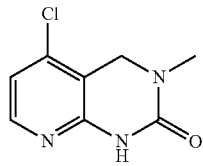

5-chloro-3-methyl-3,4-dihydropyrido [2,3-d] pyrimidin-2 (1H)-one (19)

Methylamine (0.62 g, 19.9 mmol) was added to a solution of tert-butyl (4-chloro-3-formylpyridin-2-yl) carbamate (3.40 g, 13.2 mmol) in toluene (15 mL), and stirred overnight at room temperature. The reaction mixture was concentrated and resuspended in THF (30 mL). NaBH$_4$ was added (1.0 g, 26.5 mmol), and the reaction mixture was stirred for 24 h at room temperature. The reaction mixture was filtered. The precipitate was suspended in 5% NaHCO$_3$ (100 mL), stirred for 1 h, filtered, washed with H$_2$O and CH$_3$CN, dried under vacuum to provide 19 (900 mg, 34% yield) as a solid. LC-MS (M+H=198, obsd.=198).

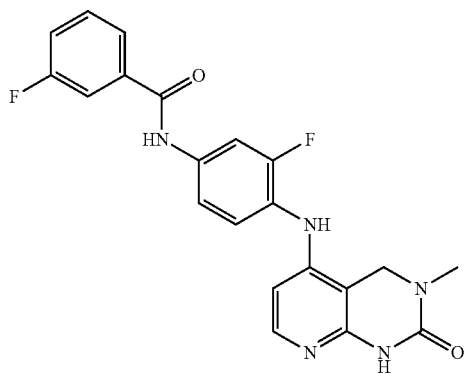 [SMILES: CN1Cc2c(Nc3ccc(NC(=O)c4cccc(F)c4)cc3F)ccnc2NC1=O]

IC$_{50}$ (AK) "+++"

3-fluoro-N-(3-fluoro-4-(3-methyl-2-oxo-1,2,3,4-tetrahydropyrido [2,3-d] pyrimidin-5-ylamino) phenyl) benzamide (20)

19 (40.0 mg, 0.20 mmol), N-(4-amino-3-fluorophenyl)-3-fluorobenzamide (50.2 mg, 0.20 mmol), and HCl (51.0 μl, 0.18 mol) were suspended in NMP (1 mL), and stirred for 1 h at 170° C. in a microwave. The resulting mixture was purified by HPLC to provide 20 (17 mg, 20% yield) as a solid. LC-MS (M+H=410, obsd.=410).

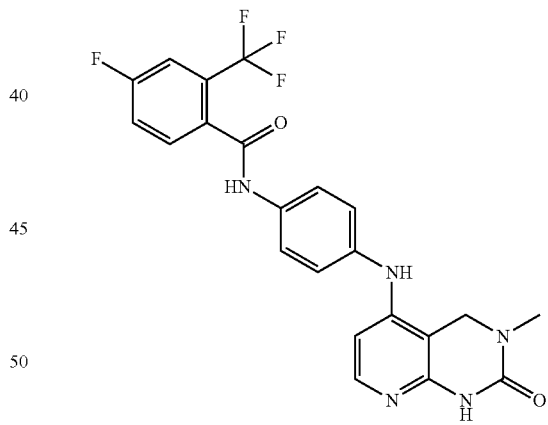

IC$_{50}$ (AK) "+++"

4-fluoro-N-(4-(3-methyl-2-oxo-1,2,3,4-tetrahydropyrido [2,3-d] pyrimidin-5-ylamino) phenyl)-2-(trifluoromethyl) benzamide (21)

The title compound was synthesized according to the procedure described for the preparation of Example 20 using 19 and N-(4-amino-phenyl)-4-fluoro-2-trifluoromethyl-benzamide. LC-MS (M+H=460, obsd.=460). $^1$H NMR: (DMSO-D6) δ 2.94 (s, 3H), 4.43(s, 2H), 6.53(d, 1H), 7.26 (d, 2H), 7.75-7.82 (m, 7H), 9.05(s, 1H), 10.27 (s, 1H); 10.73 (s, 1H).

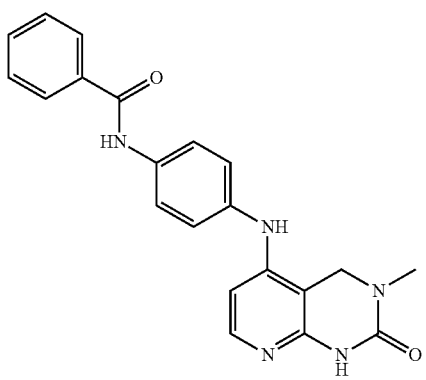 [SMILES: CN1Cc2c(Nc3ccc(NC(=O)c4ccccc4)cc3)ccnc2NC1=O]

IC$_{50}$ (AK) "++"

N-(4-(3-methyl-2-oxo-1,2,3,4-tetrahydropyrido [2,3-d] pyrimidin-5-ylamino) phenyl) benzamide (22)

The title compound was synthesized according to the procedure described for the preparation of Example 20 using 19 and N-(4-aminophenyl) benzamide. LC-MS (M+H=374, obsd.=374).

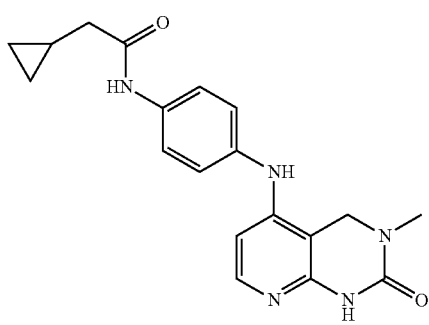 [SMILES: CN1Cc2c(Nc3ccc(NC(=O)CC4CC4)cc3)ccnc2NC1=O]

IC$_{50}$ (AK) "+"

2-cyclopropyl-N-(4-(3-methyl-2-oxo-1,2,3,4-tetrahydropyrido [2,3-d] pyrimidin-5-ylamino) phenyl) acetamide (23)

The title compound was synthesized according to the procedure described for the preparation of Example 20 using 19 and N-(4-amino-phenyl)-2-cyclopropyl-acetamide. LC-MS (M+H=352, obsd.=352).

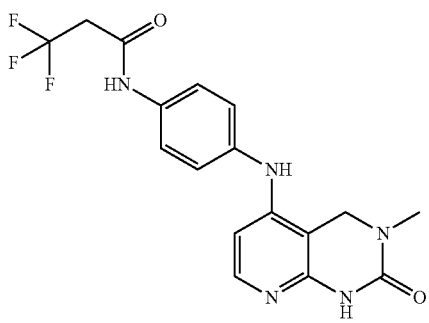 [SMILES: CN1Cc2c(Nc3ccc(NC(=O)CC(F)(F)F)cc3)ccnc2NC1=O]

IC$_{50}$ (AK) "+"

3,3,3-trifluoro-N-(4-(3-methyl-2-oxo-1,2,3,4-tetrahydropyrido [2,3-d] pyrimidin-5-ylamino) phenyl) propanamide (24)

The title compound was synthesized according to the procedure described for the preparation of Example 20 using 19 and N-(4-amino-phenyl)-3,3,3-trifluoro-propionamide. LC-MS (M+H=380, obsd.=380).

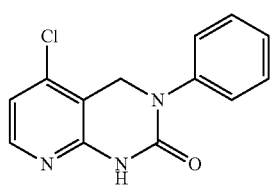 [SMILES: O=C1Nc2nccc(Cl)c2CN1c1ccccc1]

5-chloro-3-phenyl-3,4-dihydropyrido [2,3-d] pyrimidin-2 (1H)-one (25)

The title compound was synthesized according to the procedure described for the preparation of Example 1 using aniline. LC-MS (M+H=261, obsd.=261).

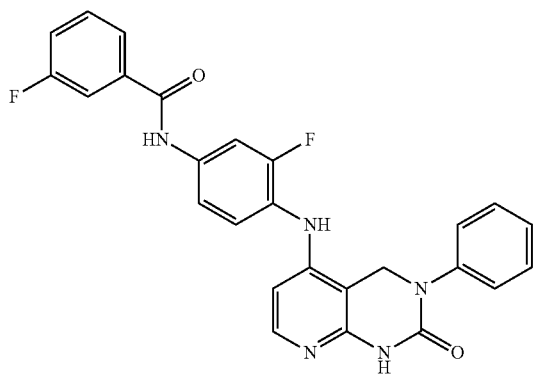 [SMILES: O=C(Nc1ccc(Nc2ccnc3c2CN(c2ccccc2)C(=O)N3)c(F)c1)c1cccc(F)c1]

IC$_{50}$ (AK) "++"

3-fluoro-N-(3-fluoro-4-(2-oxo-3-phenyl-1,2,3,4-tetrahydropyrido [2,3-d] pyrimidin-5-ylamino) phenyl) benzamide (26)

The title compound was synthesized according to the procedure described for the preparation of Example 20 using 25 and N-(4-amino-3-fluorophenyl)-3-fluorobenzamide. LC-MS (M+H=472, obsd.=472).

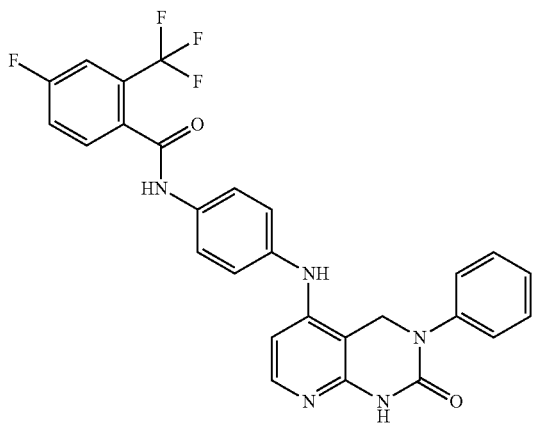 [SMILES: O=C(Nc1ccc(Nc2ccnc3c2CN(c2ccccc2)C(=O)N3)cc1)c1ccc(F)cc1C(F)(F)F]

IC$_{50}$ (AK) "++"

4-fluoro-N-(4-(2-oxo-3-phenyl-1,2,3,4-tetrahydropyrido [2,3-d] pyrimidin-5-ylamino) phenyl)-2-(trifluoromethyl) benzamide (27)

The title compound was synthesized according to the procedure described for the preparation of Example 2 using 25 and N-(4-amino-phenyl)-4-fluoro-2-trifluoromethyl-benzamide. LC-MS (M+H=522, obsd.=522).

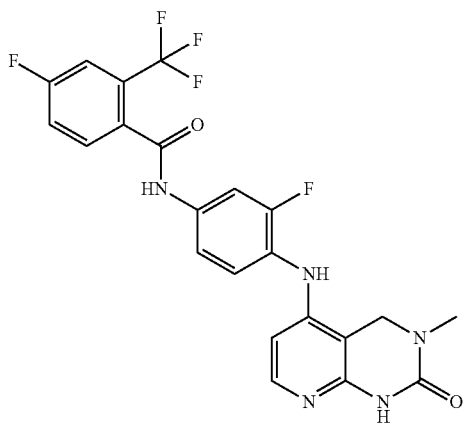 [SMILES: CN1Cc2c(Nc3ccc(NC(=O)c4ccc(F)cc4C(F)(F)F)cc3F)ccnc2NC1=O]

IC$_{50}$(AK) "+++"

4-fluoro-N-(3-fluoro-4-(3-methyl-2-oxo-1,2,3,4-tetrahydropyrido [2,3-d] pyrimidin-5-ylamino) phenyl)-2-(trifluoromethyl) benzamide (28)

19 (176 mg, 0.89 mmol), Pd(OAc)$_2$ (29 mg, 0.13 mmol), X-Phos (127 mg, 0.27 mmol), N-(4-amino-3-fluorophenyl)-5-fluoro-2-(trifluoromethyl) benzamide (267 mg, 0.85 mmol), and NaOtBu (171 mg, 1.78 mmol) were suspended in dioxane (2 mL) and stirred at 100° C. for 4 h. The crude reaction mixture was purified directly via HPLC to provide 28 (110 mg, 25% yield) as a solid. LC-MS (M+H=478, obsd.=478).

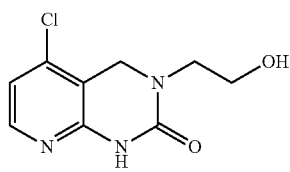

5-chloro-3-(2-hydroxyethyl)-3,4-dihydropyrido [2,3-d] pyrimidin-2 (1 H)-one (29)

The title compound was synthesized according to the procedure described for the preparation of Example 19 using 2-aminoethanol. LC-MS (M+H=228, obsd.=228).

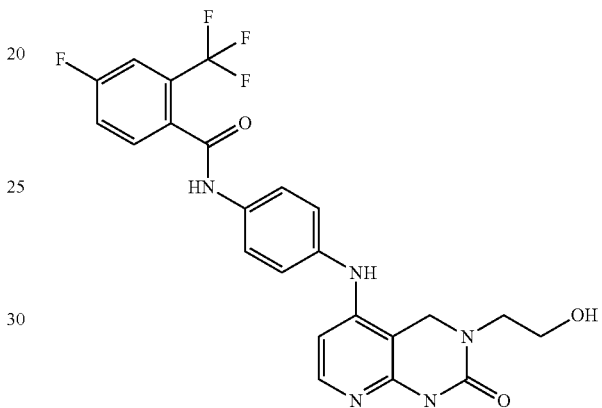

IC$_{50}$ (AK) "++"

4-fluoro-N-(4-(3-(2-hydroxyethyl)-2-oxo-1,2,3,4-tetrahydropyrido [2,3-d] pyrimidin-5-ylamino) phenyl)-2-(trifluoromethyl) benzamide (30)

The title compound was synthesized according to the procedure described for the preparation of Example 20 using 29 and N-(4-amino-phenyl)-4-fluoro-2-trifluoromethyl-benzamide. LC-MS (M+H=490, obsd.=490). $^1$HNMR: (DMSO-D6) δ 3.43 (t, 2H); 3.63 (t, 2H); 4.54 (s, 2H); 6.53 (d, 2H); 7.26(d, 2H), 7.75-7.78 (m, 6H); 9.13 (s, 1H); 10.28(s, 1H); 10.73(2, 1H).

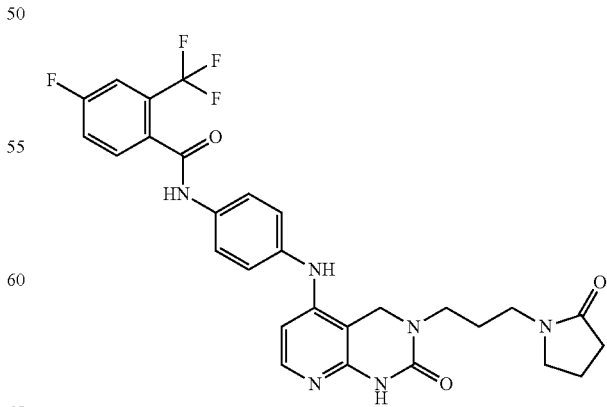

IC$_{50}$ (AK) "++"

4-fluoro-N-(4-(2-oxo-3-(3-(2-oxopyrrolidin-1-yl)
propyl)-1,2,3,4-tetrahydropyrido [2,3-d] pyrimidin-
5-ylamino) phenyl)-2-(trifluoromethyl) benzamide
(31)

The intermediate scaffold was synthesized according to the procedure described for the preparation of Example 19 using 1-(3-amino-propyl)-pyrrolidin-2-one. The title compound was synthesized according to the procedure described for the preparation of Example 20 using the above intermediate and N-(4-amino-phenyl)-4-fluoro-2-trifluoromethyl-benzamide. LC-MS (M+H=571, obsd.=571). $^1$H NMR: (DMSO-D6) δ 1.80 (m, 2H); 1.93 (m, 2H); 2.49(t, 2H); 3.32 (t, 2H); 3.35-3.37 (m, 4H); 4.46 (s, 2H); 6.53 (d, 1H); 7.27(d, 1H); 7.76-7.79 (m, 6H); 9.14 (s, 1H); 10.37 (s, 1H); 10.75(s, 1H).

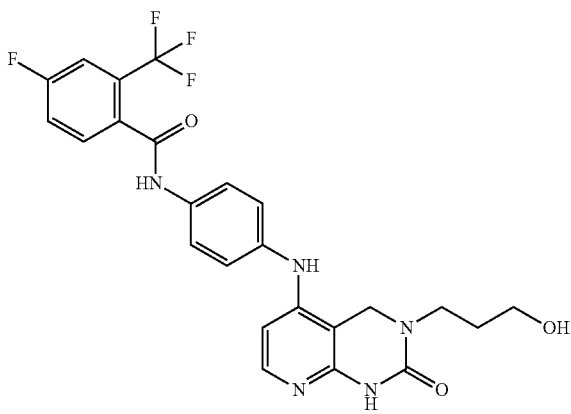 [SMILES: O=C(Nc1ccc(Nc2ccnc3c2CN(CCCO)C(=O)N3)cc1)c1ccc(F)cc1C(F)(F)F]

IC$_{50}$ (AK) "+++"

4-fluoro-N-(4-(3-(3-hydroxypropyl)-2-oxo-1,2,3,4-
tetrahydropyrido [2,3-d] pyrimidin-5-ylamino) phe-
nyl)-2-(trifluoromethyl) benzamide (32)

The intermediate scaffold was synthesized according to the procedure described for the preparation of Example 19 using 3-amino-propan-1-ol.

The title compound was synthesized according to the procedure described for the preparation of Example 20 using the above intermediate and N-(4-amino-phenyl)-4-fluoro-2-trifluoromethyl-benzamide. LC-MS (M+H=504, obsd.=504).

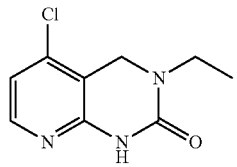

5-chloro-3-ethyl-3, 4-dihydropyrido[2,3-d]pyrimi-
din-2 (1H)-one (33)

The intermediate scaffold was synthesized according to the procedure described for the preparation of Example 19 using ethylamine. LC-MS (M+H=212, obsd.=212). $^1$H NMR: (DMSO-D6) δ 1.08(t, 3H); 3.34-3.40(m, 2H); 4.50(s, 2H); 7.03(d, 1H); 8.02 (d, 1H); 9.91 (s, 1H).

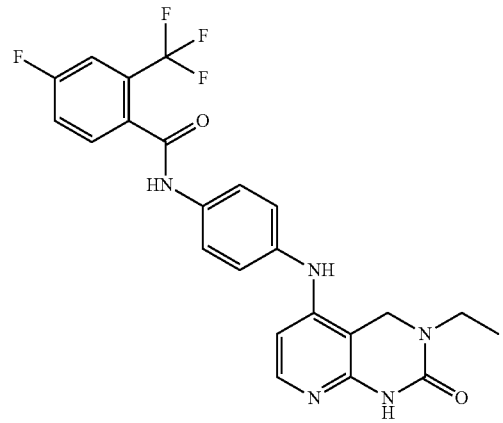 [SMILES: CCN1Cc2c(Nc3ccc(NC(=O)c4ccc(F)cc4C(F)(F)F)cc3)ccnc2NC1=O]

IC$_{50}$ (AK) "+++"

N-(4-(3-ethyl-2-oxo-1,2,3,4-tetrahydropyrido [2,3-d]
pyrimidin-5-ylamino) phenyl)-4-fluoro-2-(trifluo-
romethyl) benzamide (34)

The title compound was synthesized according to the procedure described for the preparation of Example 20 using 33 and N-(4-amino-phenyl)-4-fluoro-2-trifluoromethyl-benzamide. LC-MS (M+H=474, obsd.=474).

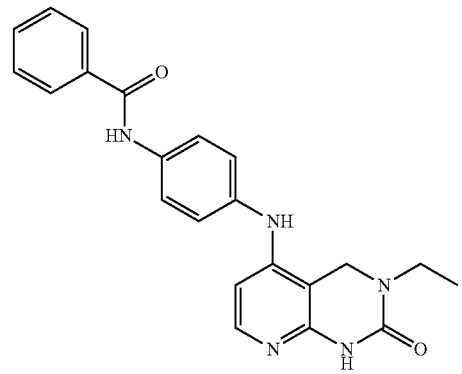 [SMILES: CCN1Cc2c(Nc3ccc(NC(=O)c4ccccc4)cc3)ccnc2NC1=O]

IC$_{50}$ (AK) "++"

N-(4-(3-ethyl-2-oxo-1,2,3,4-tetrahydropyrido [2,3-d]
pyrimidin-5-ylamino) phenyl) benzamide (35)

The title compound was synthesized according to the procedure described for the preparation of Example 20 using 33 and N-(4-aminophenyl) benzamide. LC-MS (M+H=388, obsd.=388).

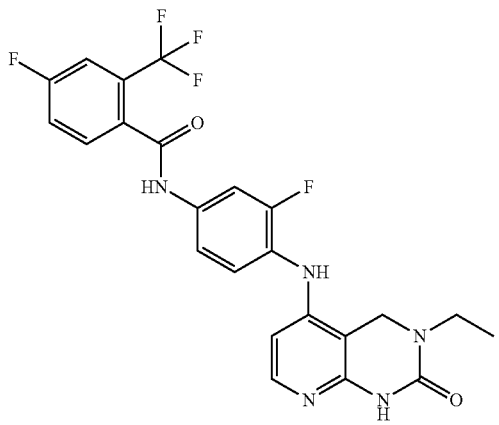 [SMILES: CCN1Cc2c(Nc3ccc(NC(=O)c4ccc(F)cc4C(F)(F)F)cc3F)ccnc2NC1=O]

IC$_{50}$ (AK) "+++"

N-(4-(3-ethyl-2-oxo-1,2,3,4-tetrahydropyrido [2,3-d] pyrimidin-5-ylamino)-3-fluorophenyl)-4-fluoro-2-(trifluoromethyl) benzamide (36)

The title compound was synthesized according to the procedure described for the preparation of Example 28 using 33 and N-(4-amino-3-fluorophenyl)-5-fluoro-2-(trifluoromethyl) benzamide. LC-MS (M+H=492, obsd.=492).

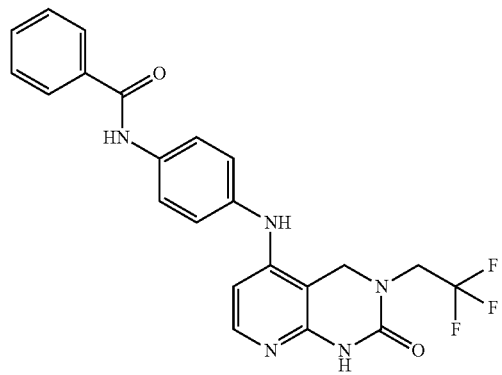 [SMILES: O=C(Nc1ccc(Nc2ccnc3c2CN(CC(F)(F)F)C(=O)N3)cc1)c1ccccc1]

IC$_{50}$ (AK) "++"

N-(4-(2-oxo-3-(2,2,2-trifluoroethyl)-1,2,3,4-tetrahydropyrido[2,3-d]pyrimidin-5-ylmino)phenyl)benzamide (37)

The intermediate scaffold was synthesized according to the procedure described for the preparation of Example 19 using 2,2,2-trifluoro-ethylamine.

title compound was synthesized according to the procedure described for the preparation of Example 20 using the above intermediate and N-(4-aminophenyl) benzamide. LC-MS (M+H=442, obsd.=442).

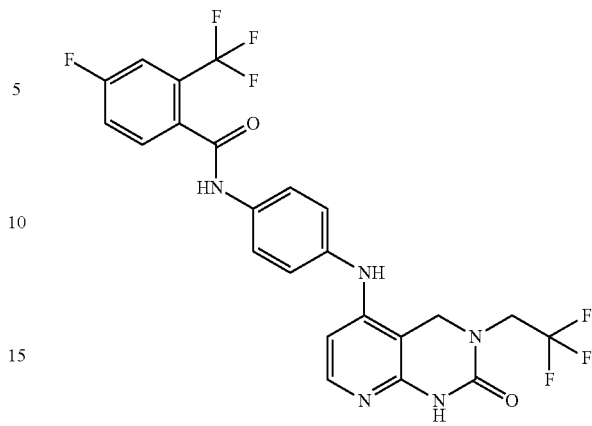

IC$_{50}$ (AK) "++"

4-fluoro-N-(4-(2-oxo-3-(2,2,2-trifluoroethyl)-1,2,3,4-tetrahydropyrido [2,3-d] pyrimidin-5-ylamino) phenyl)-2-(trifluoromethyl) benzamide (38)

The title compound was synthesized according to the procedure described for the preparation of Example 20 using the scaffold intermediate from example 37 and N-(4-amino-3-fluorophenyl)-5-fluoro-2-(trifluoromethyl) benzamide. LC-MS (M+H=528, obsd.=528).

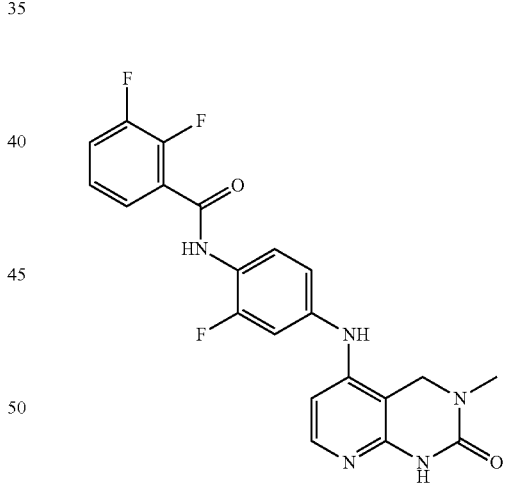

IC$_{50}$ (AK) "++"

2,3-difluoro-N-(2-fluoro-4-(3-methyl-2-oxo-1,2,3,4-tetrahydropyrido [2,3-d] pyrimidin-5-ylamino) phenyl) benzamide (39)

The title compound was synthesized according to the procedure described for the preparation of Example 20 using 19 and N-(4-amino-2-fluoro-phenyl)-2,3-difluoro-benzamide. LC-MS (M+H=428, obsd.=428).

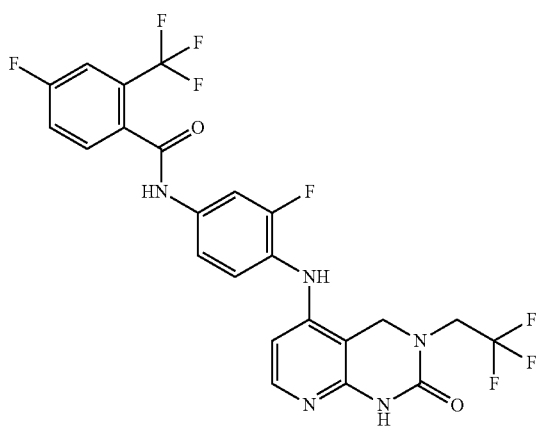 [SMILES: O=C(Nc1ccc(Nc2ccnc3c2CN(CC(F)(F)F)C(=O)N3)c(F)c1)c1ccc(F)cc1C(F)(F)F]

IC$_{50}$ (AK) "+++"

4-fluoro-N-(3-fluoro-4-(2-oxo-3-(2,2,2-trifluoroethyl)-1,2,3,4-tetrahydropyrido[2,3-d]pyrimidin-5-ylamino)phenyl)-2-(trifluoromethyl) benzamide (40)

The title compound was synthesized according to the procedure described for the preparation of Example 28 using scaffold intermediate from example 37 and N-(4-amino-3-fluorophenyl)-5-fluoro-2-(trifluoromethyl) benzamide. LC-MS (M+H=546, obsd.=546). $^1$HNMR: (DMSO-D6) δ 4.19-4.22 (m, 2H); 4.61 (s, 2H); 6.22 (d, 1H); 7.36 (m, 1H); 7.50(m, 1H); 7.78-7.85(m, 5H); 8.85(s, 1H), 10.5 (s, 1H); 10.94 (s, 1H).

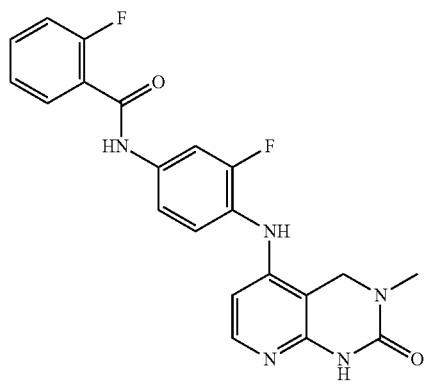 [SMILES: CN1Cc2c(Nc3ccc(NC(=O)c4ccccc4F)cc3F)ccnc2NC1=O]

IC$_{50}$ (AK) "++"

2-fluoro-N-(3-fluoro-4-(3-methyl-2-oxo-1,2,3,4-tetrahydropyrido[2,3-d] pyrimidin-5-ylamino) phenyl) benzamide (41)

The title compound was synthesized according to the procedure described for the preparation of Example 20 using 19 and N-(4-amino-3-fluoro-phenyl)-2-fluoro-benzamide. LC-MS (M+H=410, obsd.=410).

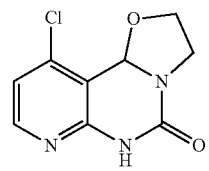 [SMILES: O=C1Nc2nccc(Cl)c2C2OCCN12]

10-chloro-6, 10b-dihydro-2H-oxazolo[3,2-c] pyrido [3,2-e] pyrimidin-5 (3H)-one (42)

tert-Butyl(4-chloro-3-formylpyridin-2-yl)carbamate (2.0 g, 7.79 mmol), 2-aminoethanol (0.57 g, 9.35 mmol), and AcOH (0.47 g; 7.79 mmol) were suspended in toluene (20 mL), and stirred overnight at room temperature. The reaction mixture was concentrated, and suspended in hexanes/ether (5/1, v/v). The resulting precipitate was filtered, suspended in NMP (3 mL) in 20 ml seal tube, and heated for 30 min. at 150° C. The crude product was purified directly via HPLC to provide 42 (270 mg, 10% yield) as a solid. LC-MS (M+H=226, obsd.=226).

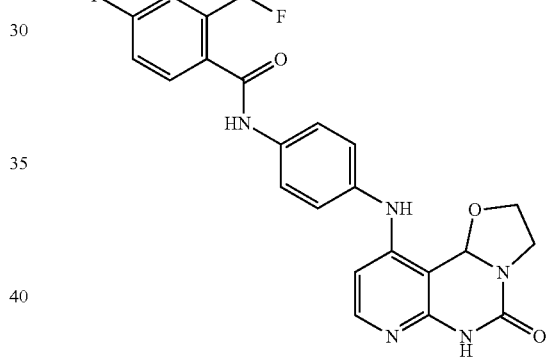

IC$_{50}$ (AK) "+"

4-fluoro-N-(4-(5-oxo-3,5,6,10b-tetrahydro-2H-oxazolo[3,2-c] pyrido [3,2-e] pyrimidin-10-ylamino) phenyl)-2-(trifluoromethyl) benzamide (43)

42 (16 mg, 0.07 mmol), N-(4-aminophenyl)-4-fluoro-2-(trifluoromethyl) benzamide (22 mg, 0.07 mmol), and 4.0M HCl in dioxane (18 µl, 0.07 mmol) were suspended in a sealed tube, and placed in microwave at 140° C. for 1 h. The crude product was purified directly via HPLC to provide 43. LC-MS (M+H=488, obsd.=488).

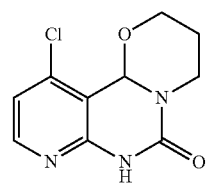 [SMILES: O=C1Nc2nccc(Cl)c2C2OCCCN12]

11-chloro-3,4,7,11b-tetrahydro-[1,3] oxazino [3,2-c] pyrido [3,2-e] pyrimidin-6 (2H)-one (44)

The title compound was synthesized according to the procedure described for the preparation of Example 42 using 3-aminopropan-1-ol. LC-MS (M+H=240, obsd.=240). ¹H NMR: (DMSO-D6) δ 1.45-1.51 (m, 1H); 1.80-1.83 (m, 1H); 3.21-3.27 (m, 1H); 4.02-4.07(m, 2H); 4.35-4.10 (m, 1H); 6.01 (s, 1H); 7.16 (d, 1H); 8.21 (d, 1H); 10.65 (s, 1H).

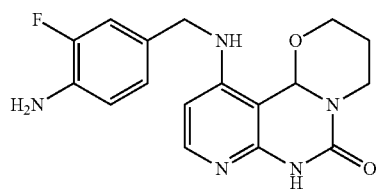 [SMILES: Nc1ccc(CNc2ccnc3c2C2OCCCN2C(=O)N3)cc1F]

11-(4-amino-3-fluorobenzylamino)-3,4,7,11b-tetrahydro-[1,3]oxazino[3,2-c]pyrido[3,2-e]pyrimidin-6 (2H)-one (45)

44 (300 mg; 1.25 mmol), 4-(aminomethyl)-2-fluoroaniline hydrochloride (442 mg; 2.50 mmol) and DIEA (1.1 mL; 6.26 mmol) were suspended in NMP (6 mL), and stirred at 120° C. for 72 h. The reaction mixture was quenched with H₂O. The resulting precipitate was filtered and dried under vacuum to provide 45 (230 mg, 53% yield) as a solid. LC-MS (M+H=344, obsd.=344).

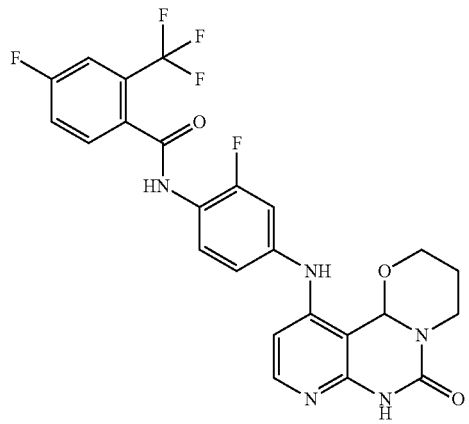 [SMILES: O=C(Nc1ccc(Nc2ccnc3c2C2OCCCN2C(=O)N3)cc1F)c1ccc(F)cc1C(F)(F)F]

4-fluoro-N-(2-fluoro-4-(6-oxo-2,3,4,6,7,11b-hexahydro-[1,3] oxazino [3,2-c] pyrido [3,2-e] pyrimidin-11-ylamino)phenyl)-2-(trifluoromethyl) benzamide (46)

The title compound was synthesized according to the procedure described for the preparation of Example 45 using 44 and N-(4-amino-2-fluorophenyl)-4-fluoro-2-(trifluoromethyl) benzamide. LC-MS (M+H=520, obsd.=520).

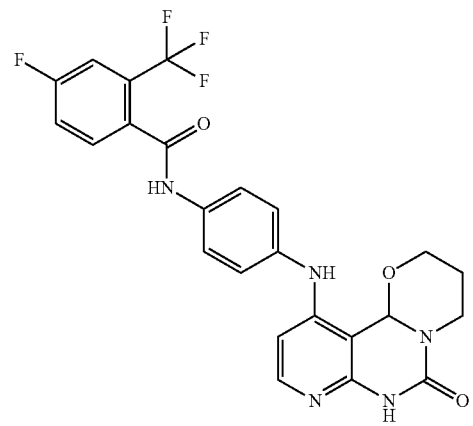 [SMILES: O=C(Nc1ccc(Nc2ccnc3c2C2OCCCN2C(=O)N3)cc1)c1ccc(F)cc1C(F)(F)F]

4-fluoro-N-(4-(6-oxo-2,3,4,6,7,11b-hexahydro-[1,3] oxazino [3,2-c] pyrido [3,2-e]pyrimidin-11-ylamino) phenyl)-2-(trifluoromethyl) benzamide (47)

The title compound was synthesized according to the procedure described for the preparation of Example 2 using 44 and N-(4-amino-phenyl)-4-fluoro-2-trifluoromethyl-benzamide. LC-MS (M+H=502, obsd.=502).

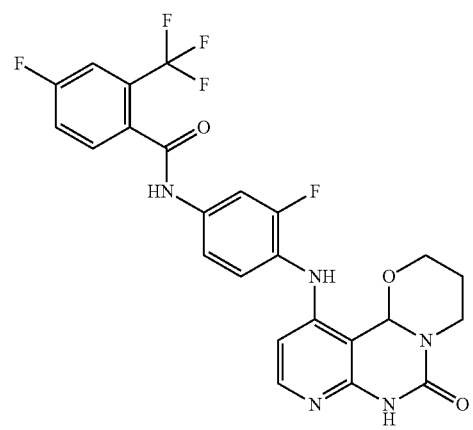 [SMILES: O=C(Nc1ccc(Nc2ccnc3c2C2OCCCN2C(=O)N3)c(F)c1)c1ccc(F)cc1C(F)(F)F]

4-fluoro-N-(3-fluoro-4-(6-oxo-2,3,4,6,7,11b-hexahydro-[1,3] oxazino [3,2-c] pyrido [3,2-e] pyrimidin-11-ylamino) phenyl)-2-(trifluoromethyl) benzamide (48)

The title compound was synthesized according to the procedure described for the preparation of Example 2 using 44 and N-(4-amino-3-fluoro-phenyl)-4-fluoro-2-trifluoromethyl-benzamide. LC-MS (M+H=520, obsd.=520).

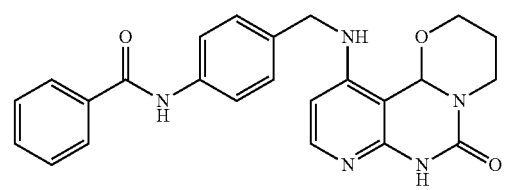 [SMILES: O=C(Nc1ccc(CNc2ccnc3c2C2OCCCN2C(=O)N3)cc1)c1ccccc1]

N-(4-((6-oxo-2,3,4,6,7,11b-hexahydro-[1,3] oxazino [3,2-c] pyrido [3,2-e] pyrimidin-11-ylamino) methyl) phenyl) benzamide (49)

44 (50 mg; 0.21 mmol), N-[4-(aminomethyl) phenyl]benzamide hydrochloride (110 mg; 0.42 mmol), and DIEA (112 µl; 0.63 mmol) were suspended in NMP (1 mL), and stirred overnight at 110° C. The crude product was purified directly via HPLC to provide 49 (13 mg, 15% yield) as a solid. LC-MS (M+H=430, obsd.=430).

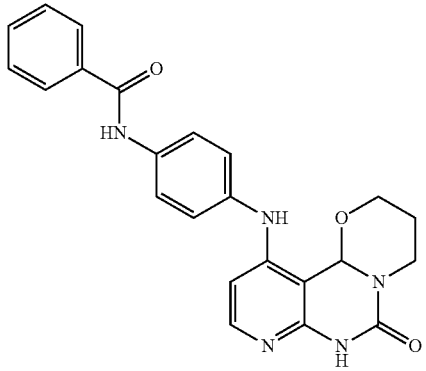 [SMILES: O=C(Nc1ccc(Nc2ccnc3c2C2OCCCN2C(=O)N3)cc1)c1ccccc1]

N-(4-(6-oxo-2,3,4,6,7,11b-hexahydro-[1,3] oxazino [3,2-c] pyrido [3,2-e] pyrimidin-11-ylamino) phenyl) benzamide (50)

44 (40 mg; 0.17 mmol), N-(4-aminophenyl) benzamide (39 mg; 0.18 mmol), and 4.0M HCl in dioxane (51 µl; 0.17 mol) were suspended in NMP (1 mL) and placed in a microwave at 120° C. for 1 h. The crude product was purified directly via HPLC to provide 50 (9 mg, 13% yield) as a solid. LC-MS (M+H=416, obsd.=416).

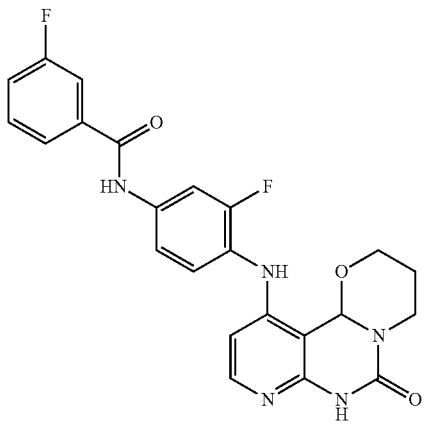 [SMILES: O=C(Nc1ccc(Nc2ccnc3c2C2OCCCN2C(=O)N3)c(F)c1)c1cccc(F)c1]

3-fluoro-N-(3-fluoro-4-(6-oxo-2,3,4,6,7,11b-hexahydro-[1,3] occasion [3,2-c] pyrido [3,2-e] pyrimidin-11-ylamino) phenyl) benzamide (51)

The title compound was synthesized according to the procedure described for the preparation of Example 50 using 44 and N-(4-amino-3-fluorophenyl)-3-fluorobenzamide. LC-MS (M+H=452, obsd.=452).

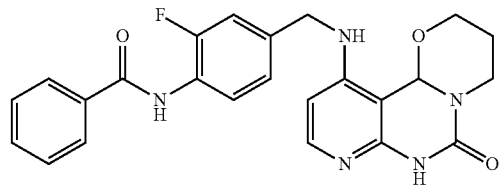 [SMILES: O=C(Nc1ccc(CNc2ccnc3c2C2OCCCN2C(=O)N3)cc1F)c1ccccc1]

N-(2-fluoro-4-((6-oxo-2,3,4,6,7,11b-hexahydro-[1,3] oxazino [3,2-c] pyrido [3,2-e] pyrimidin-11-ylamino) methyl)phenyl) benzamide (52)

Benzoic acid (35 mg; 0.17 mmol), Bop-Cl (39 mg; 0.16 mmol), DIEA (0.04 mL; 0.25 mmol), and 45 (55mg, 0.26 mmol) were suspended in DMF (2 mL), and stirred overnight at room temperature. The crude reaction mixture was purified directly via HPLC to provide 52 (7 mg, 10% yield) as a solid. LC-MS (M+H=448, obsd.=448).

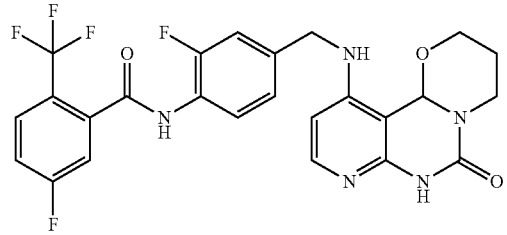 [SMILES: O=C(Nc1ccc(CNc2ccnc3c2C2OCCCN2C(=O)N3)cc1F)c1cc(F)ccc1C(F)(F)F]

5-fluoro-N-(2-fluoro-4-((6-oxo-2,3,4,6,7,11b-hexahydro-[1,3]oxazino[3,2-c]pyrido[3,2-e]pyrimidin-11-ylamino)methyl)phenyl)-2-(trifluoromethyl) benzamide (53)

The title compound was synthesized according to the procedure described for the preparation of Example 52 using 45 and 5-fluoro-2-trifluoromethyl-benzoic acid. LC-MS (M+H=534, obsd.=534).

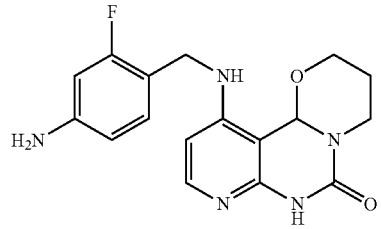 [SMILES: Nc1ccc(CNc2ccnc3c2C2OCCCN2C(=O)N3)c(F)c1]

11-(4-amino-2-fluorobenzylamino)-3,4,7,11b-tetrahydro-[1,3] oxazino [3,2-c] pyrido [3,2-e] pyrimidin-6 (2H)-one (54)

The title compound was synthesized according to the procedure described for the preparation of Example 45 using 44 and 4-(aminomethyl)-3-fluoroaniline hydrochloride. LC-MS (M+H=344, obsd.=344).

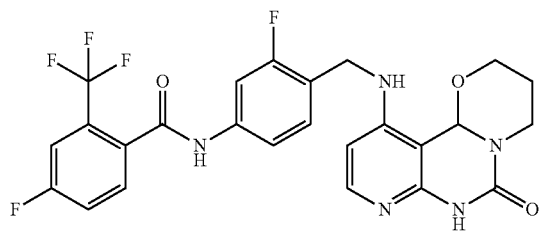 [SMILES: O=C(Nc1ccc(CNc2ccnc3c2C2OCCCN2C(=O)N3)c(F)c1)c1ccc(F)cc1C(F)(F)F]

4-fluoro-N-(3-fluoro-4-((6-oxo-2,3,4,6,7,11b-hexahydro-[1,3] oxazino [3,2-c] pyrido [3,2-e] pyrimidin-11-ylamino) methyl) phenyl)-2-(trifluoromethyl)benzamide (55)

The title compound was synthesized according to the procedure described for the preparation of Example 52 using 54 and 4-fluoro-2-trifluoromethyl-benzoic acid. LC-MS (M+H=534, obsd.=534).

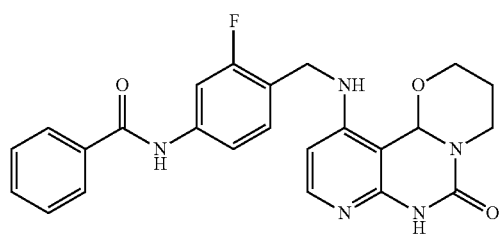 [SMILES: O=C(Nc1ccc(CNc2ccnc3c2C2OCCCN2C(=O)N3)c(F)c1)c1ccccc1]

N-(3-fluoro-4-((6-oxo-2,3,4,6,7,11b-hexahydro-[1,3] oxazino [3,2-c] pyrido [3,2-e] pyrimidin-11-ylamino) methyl) phenyl) benzamide (56)

The title compound was synthesized according to the procedure described for the preparation of Example 52 using 54 and benzoic acid. LC-MS (M+H=448, obsd.=448).

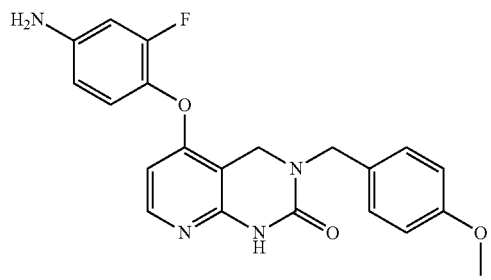 [SMILES: COc1ccc(CN2Cc3c(Oc4ccc(N)cc4F)ccnc3NC2=O)cc1]

5-(4-amino-2-fluorophenoxy)-3-(4-methoxybenzyl)-3,4-dihydropyrido[2,3-d]pyrimidin-2(1H)-one (57)

The title compound was synthesized with 1,4-amino-2-fluoro-phenol, $Cs_2CO_3$ in DMF. The compound was purified via precipitation from $H_2O$, filtering, and drying under vacuum. LC-MS (M+H=395, obsd.=395).

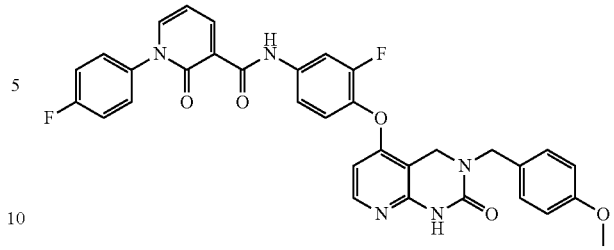

N-(3-fluoro-4-{[3-(4-methoxybenzyl)-2-oxo-1,2,3,4-tetrahydropyrido[2,3-d]pyrimidin-5-yl]oxy}phenyl)-1-(4-fluorophenyl)-2-oxo-1,2-dihydropyridine-3-carboxamide (58)

The title compound was synthesized according to the procedure described for the preparation of Example 52 using 57 and 1-(4-fluoro-phenyl)-2-oxo-1,2-dihydro-pyridine-3-carboxylic acid. LC-MS (M+H=610, obsd.=610).

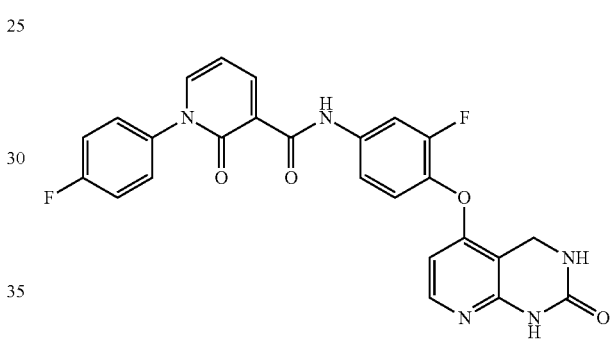

$IC_{50}$ (RON) "+++"

N-{3-fluoro-4-[(2-oxo-1,2,3,4-tetrahydropyrido[2,3-d]pyrimidin-5-yl)oxy]phenyl}-1-(4-fluorophenyl)-2-oxo-1,2-dihydropyridine-3-carboxamide (59)

The title compound was synthesized according to the procedure described for the preparation of Example 3 using 58 with HPLC purification. LC-MS (M+H=490, obsd.=490).

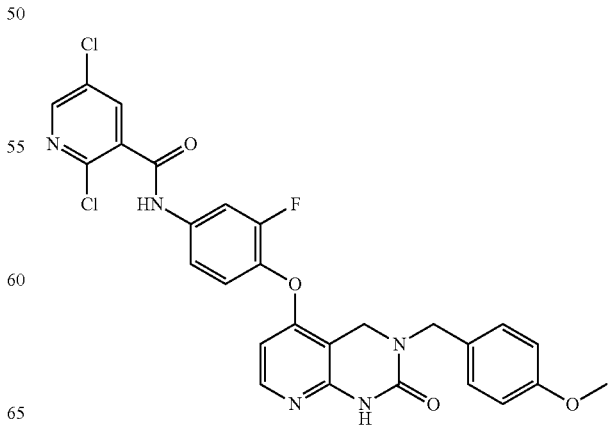

2,5-dichloro-N-(3-fluoro-4-{[3-(4-methoxybenzyl)-2-oxo-1,2,3,4-tetrahydropyrido[2,3-d]pyrimidin-5-yl]oxy}phenyl)nicotinamide (60)

57 (50 mg, 0.13 mmol) and 2,5-dichloropyridine-3-carbonyl chloride (29 mg, 0.14 mmol) were suspended in pyridine (1 mL), and stirred overnight at room temperature. The crude product was purified directly via HPLC. LC-MS (M+H=568, obsd.=568).

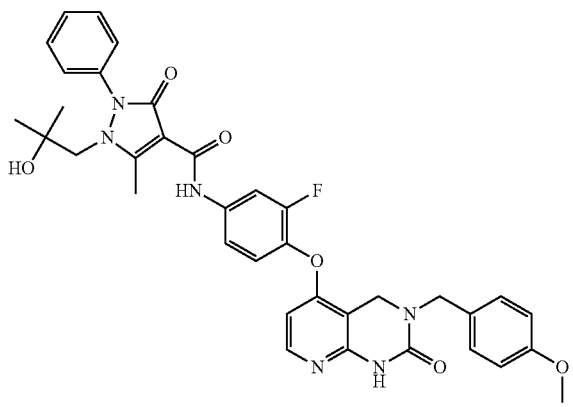 [SMILES: COc1ccc(CN2Cc3c(Oc4ccc(NC(=O)c5c(C)n(CC(C)(C)O)n(-c6ccccc6)c5=O)cc4F)ccnc3NC2=O)cc1]

N-(3-fluoro-4-{[3-(4-methoxybenzyl)-2-oxo-1,2,3,4-tetrahydropyrido[2,3-d]pyrimidin-5-yl]oxy}phenyl)-1-(2-hydroxy-2-methylpropyl)-5-methyl-3-oxo-2-phenyl-2,3-dihydro-1H-pyrazole-4-carboxamide (61)

1-(2-Hydroxy-2-methyl-propyl)-5-methyl-3-oxo-2-phenyl-2,3-dihydro-1H-pyrazole-4-carboxylic acid (40 mg; 0.14 mmol), Bop-Cl (48 mg; 0.19 mmol), and DIEA (0.06 mL; 0.38 mmol) were dissolved in dioxane (3 mL), and stirred for 2 h at room temperature. 57 (50 mg; 0.13 mmol) was added, and reaction mixture was stirred overnight at room temperature. The crude product was purified via silica gel chromatography. LC-MS (M+H=667, obsd.=667).

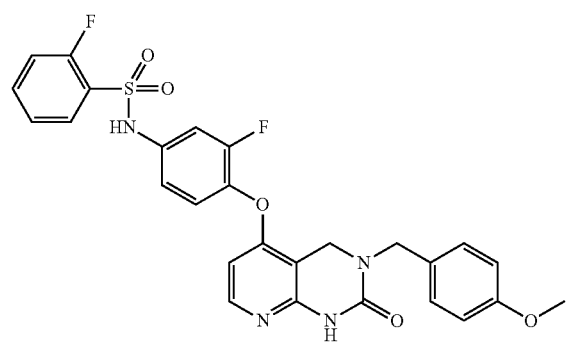 [SMILES: COc1ccc(CN2Cc3c(Oc4ccc(NS(=O)(=O)c5ccccc5F)cc4F)ccnc3NC2=O)cc1]

2-fluoro-N-(3-fluoro-4-{[3-(4-methoxybenzyl)-2-oxo-1,2,3,4-tetrahydropyrido[2,3-d]pyrimidin-5-yl]oxy}phenyl)benzenesulfonamide (62)

57 (45 mg, 0.11 mmol) and 2-fluorobenzenesulfonyl chloride (24 mg, 0.12 mmol) were suspended in pyridine (1 mL), and stirred overnight at room temperature. The crude product was purified directly via HPLC. LC-MS (M+H=553, obsd.=553).

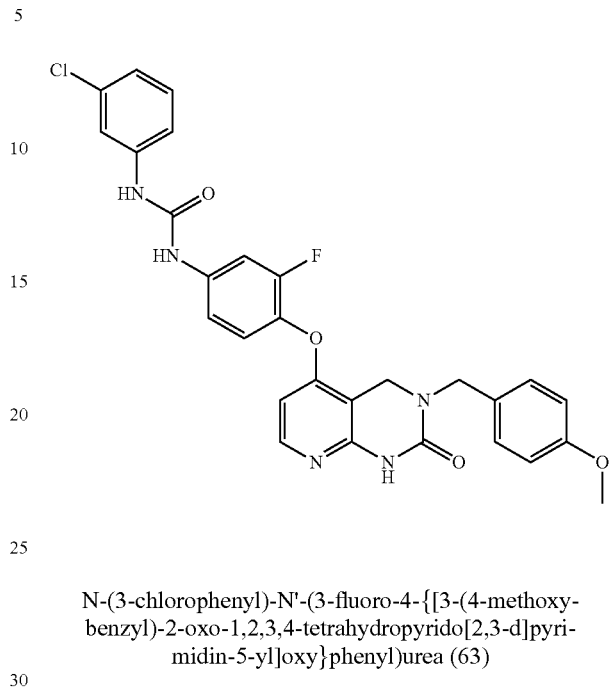

N-(3-chlorophenyl)-N'-(3-fluoro-4-{[3-(4-methoxybenzyl)-2-oxo-1,2,3,4-tetrahydropyrido[2,3-d]pyrimidin-5-yl]oxy}phenyl)urea (63)

57 (20 mg, 0.05 mmol), DIEA (304, 0.15 mmol), and 3-chlorophenyl isocyanate (9.4 mg, 0.06 mmol) were suspended in dioxane (2 mL), and stirred overnight at room temperature. The crude product was purified directly via HPLC. LC-MS (M+H=548, obsd.=548).

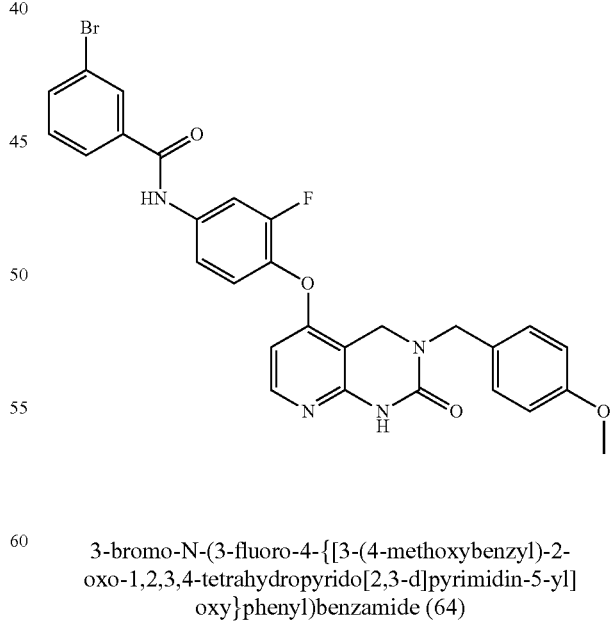

3-bromo-N-(3-fluoro-4-{[3-(4-methoxybenzyl)-2-oxo-1,2,3,4-tetrahydropyrido[2,3-d]pyrimidin-5-yl]oxy}phenyl)benzamide (64)

The title compound was synthesized according to the procedure described for the preparation of Example 61 using 57 and 3-bromo benzoic acid. LC-MS (M+H=578, obsd.=578).

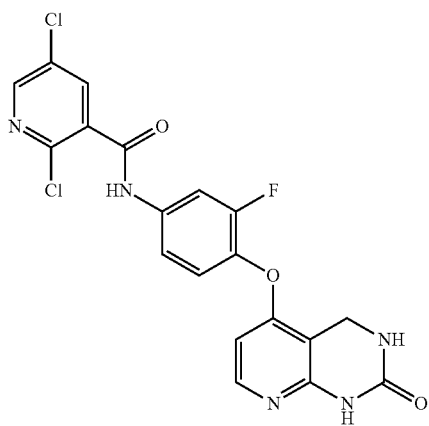 [SMILES: O=C1NCc2c(Oc3ccc(NC(=O)c4cc(Cl)cnc4Cl)cc3F)ccnc2N1]

IC$_{50}$ (AK) "++"
IC$_{50}$ (RON) "++"

2,5-dichloro-N-{3-fluoro-4-[(2-oxo-1,2,3,4-tetrahydropyrido[2,3-d]pyrimidin-5-yl)oxy]phenyl}-nicotinamide (65)

The title compound was synthesized according to the procedure described for the preparation of Example 3 using 60. LC-MS (M+H=449, obsd.=449).

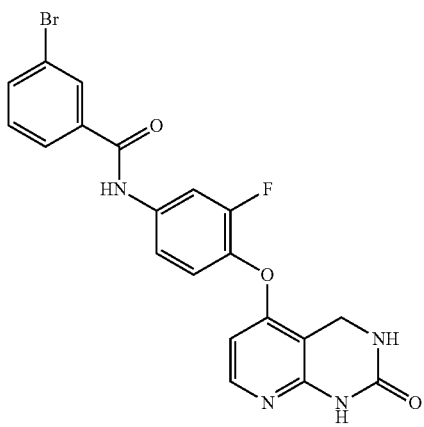 [SMILES: O=C1NCc2c(Oc3ccc(NC(=O)c4cccc(Br)c4)cc3F)ccnc2N1]

IC$_{50}$ (AK) "++"
IC$_{50}$ (RON) "++"

3-bromo-N-{3-fluoro-4-[(2-oxo-1,2,3,4-tetrahydropyrido[2,3-d]pyrimidin-5-yl)oxy]phenyl}-benzamide (66)

The title compound was synthesized according to the procedure described for the preparation of Example 3 using 64. LC-MS (M+H=458, obsd.=458).

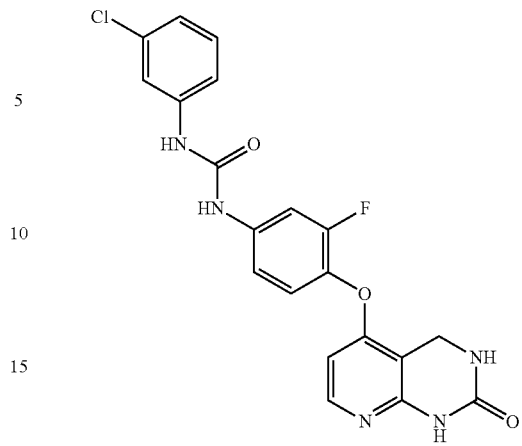

IC$_{50}$ (AK) "++"
IC$_{50}$ (RON) "++"

N-(3-chlorophenyl)-N'-{3-fluoro-4-[(2-oxo-1,2,3,4-tetrahydropyrido[2,3-d]pyrimidin-5-yl)oxy]phenyl}urea (67)

The title compound was synthesized according to the procedure described for the preparation of Example 3 using 63. LC-MS (M+H=428, obsd.=428).

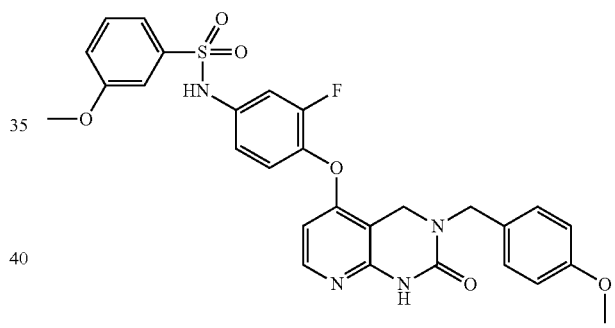

N-(3-fluoro-4-{[3-(4-methoxybenzyl)-2-oxo-1,2,3,4-tetrahydropyrido[2,3-d]pyrimidin-5-yl]oxy}phenyl)-3-methoxybenzenesulfonamide (68)

The title compound was synthesized according to the procedure described for the preparation of Example 62 using 57 and 3-methoxybenzenesulfonyl chloride. LC-MS (M+H=565, obsd.=565).

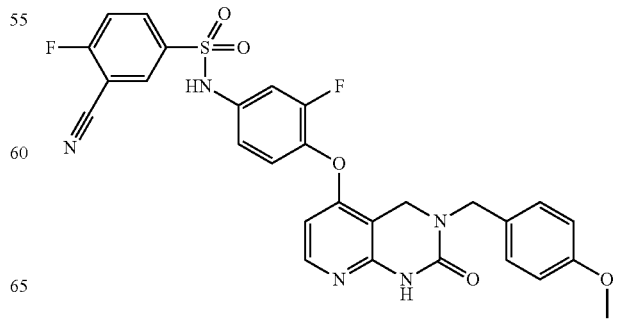

3-cyano-4-fluoro-N-(3-fluoro-4-{[3-(4-methoxybenzyl)-2-oxo-1,2,3,4-tetrahydropyrido[2,3-d]pyrimidin-5-yl]oxy}phenyl)benzenesulfonamide (69)

The title compound was synthesized according to the procedure described for the preparation of Example 62 using 57 and 3-cyano-4-fluoro-benzenesulfonyl chloride. LC-MS (M+H=578, obsd.=578).

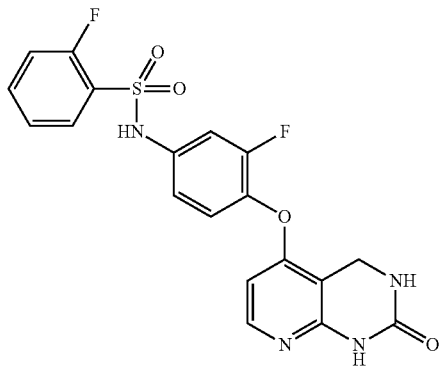 [SMILES: O=C1NCc2c(Oc3ccc(NS(=O)(=O)c4ccccc4F)cc3F)ccnc2N1]

IC$_{50}$ (AK) "+"
IC$_{50}$ (RON) "+"

2-fluoro-N-{3-fluoro-4-[(2-oxo-1,2,3,4-tetrahydro pyrido[2,3-d]pyrimidin-5-yl)oxy]phenyl}benzenesulfonamide (70)

The title compound was synthesized according to the procedure described for the preparation of Example 3 using 62. LC-MS (M+H=433, obsd.=433).

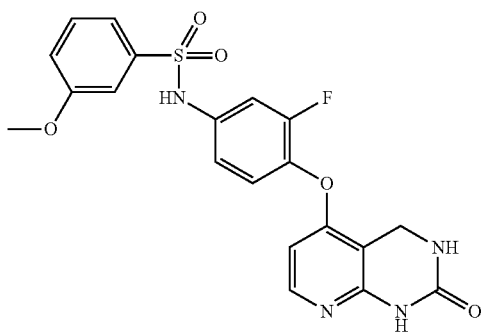 [SMILES: COc1cccc(S(=O)(=O)Nc2ccc(Oc3ccnc4c3CNC(=O)N4)c(F)c2)c1]

IC$_{50}$ (AK) "+"
IC$_{50}$ (RON) "+"

N-{3-fluoro-4-[(2-oxo-1,2,3,4-tetrahydropyrido[2,3-d]pyrimidin-5-yl)oxy]phenyl}-3-methoxybenzenesulfonamide (71)

The title compound was synthesized according to the procedure described for the preparation of Example 3 using 68. LC-MS (M+H=445, obsd.=445).

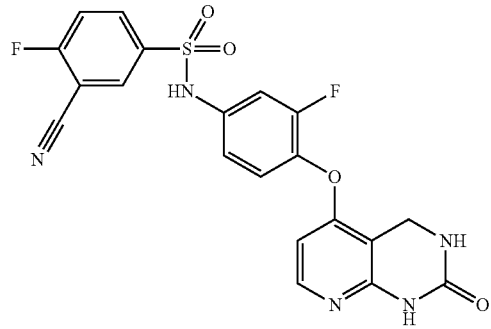 [SMILES: N#Cc1cc(S(=O)(=O)Nc2ccc(Oc3ccnc4c3CNC(=O)N4)c(F)c2)ccc1F]

3-cyano-4-fluoro-N-{3-fluoro-4-[(2-oxo-1,2,3,4-tetrahydropyrido[2,3-d]pyrimidin-5-yl)oxy]phenyl}benzenesulfonamide (72)

The title compound was synthesized according to the procedure described for the preparation of Example 3 using 69. LC-MS (M+H=458, obsd.=458).

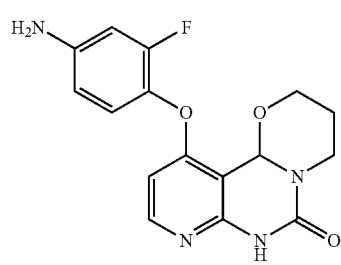 [SMILES: Nc1ccc(Oc2ccnc3c2C2OCCCN2C(=O)N3)c(F)c1]

11-(4-amino-2-fluorophenoxy)-3,4,7,11b-tetrahydro-2H,6H-pyrido[2',3':4,5]pyrimido[6,1-b][1,3]oxazin-6-one (73)

The title compound was synthesized according to the procedure described for the preparation of Example 57 using 44 and 4-amino-2-fluoro-phenol. LC-MS (M+H=331, obsd.=331).

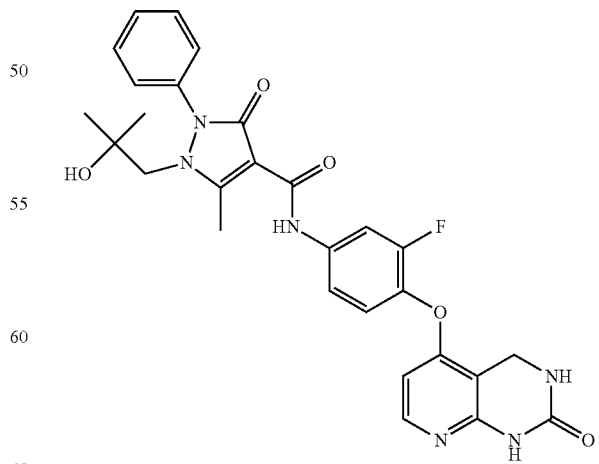

IC$_{50}$ (RON) "+"

N-{3-fluoro-4-[(2-oxo-1,2,3,4-tetrahydropyrido[2,3-d]pyrimidin-5-yl)oxy]phenyl}-1-(2-hydroxy-2-methylpropyl)-5-methyl-3-oxo-2-phenyl-2,3-dihydro-1H-pyrazole-4-carboxamide (74)

The title compound was synthesized according to the procedure described for the preparation of Example 3 using 61. LC-MS (M+H=547, obsd.=547).

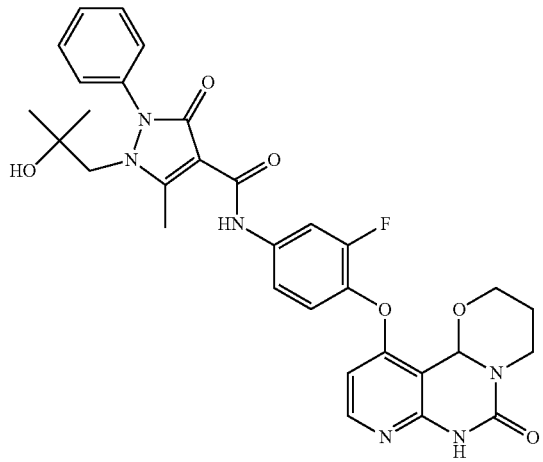 [SMILES: Cc1c(C(=O)Nc2ccc(Oc3ccnc4c3C3OCCCN3C(=O)N4)c(F)c2)c(=O)n(-c2ccccc2)n1CC(C)(C)O]

IC$_{50}$ (RON) "+"

N-{3-fluoro-4-[(6-oxo-3,4,7,11b-tetrahydro-2H,6H-pyrido[2',3':4,5]pyrimido[6,1-b][1,3]oxazin-11-yl)oxy]phenyl}-1-(2-hydroxy-2-methylpropyl)-5-methyl-3-oxo-2-phenyl-2,3-dihydro-1H-pyrazole-4-carboxamide (75)

The title compound was synthesized according to the procedure described for the preparation of Example 61 using 73 and 1-(2-hydroxy-2-methyl-propyl)-5-methyl-3-oxo-2-phenyl-2,3-dihydro-1H-pyrazole-4-carboxylic acid. LC-MS (M+H=603, obsd.=603).

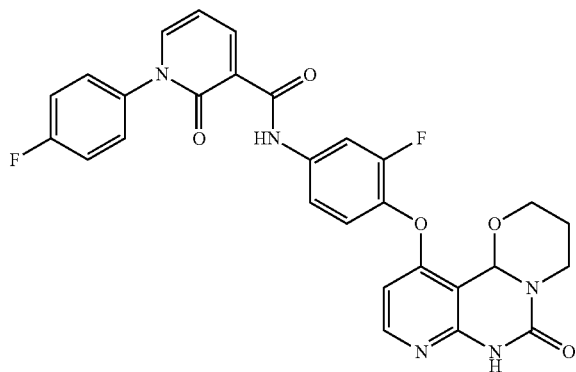 [SMILES: O=C(Nc1ccc(Oc2ccnc3c2C2OCCCN2C(=O)N3)c(F)c1)c1cccn(-c2ccc(F)cc2)c1=O]

IC$_{50}$ (RON) "++"

N-{3-fluoro-4-[(6-oxo-3,4,7,11b-tetrahydro-2H,6H-pyrido[2',3':4,5]pyrimido[6,1-b][1,3]oxazin-11-yl)oxy]phenyl}-1-(4-fluorophenyl)-2-oxo-1,2-dihydropyridine-3-carboxamide (76)

The title compound was synthesized according to the procedure described for the preparation of Example 61 using 73 and 1-(4-fluoro-phenyl)-2-oxo-1,2-dihydro-pyridine-3-carboxylic acid. LC-MS (M+H=546, obsd.=546).

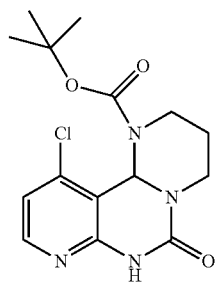 [SMILES: CC(C)(C)OC(=O)N1CCCN2C(=O)Nc3nccc(Cl)c3C21]

tert-butyl 11-chloro-6-oxo-3,4,7,11b-tetrahydro-2H-pyrido[3,2-e]pyrimido[1,2-c]pyrimidine-1(6H)-carboxylate (77)

tert-Butyl (4-chloro-3-formylpyridin-2-yl)carbamate (1.2 g, 4.67 mmol), tert-butyl (3-amino-propyl)carbamate (855 mg, 4.91 mmol), and AcOH (0.28 g, 4.67 mmol) were suspended in toluene (50 mL), and stirred overnight at room temperature. The reaction mixture was concentrated. The crude intermediate was dissolved in NMP (8 mL) in a 40 mL sealed tube, and stirred for 30 min. at 160 ° C. The reaction mixture was cooled, and the resulting precipitate was filtered, washed with MeOH, and dried under vacuum. LC-MS (M+H=339, obsd.=339).

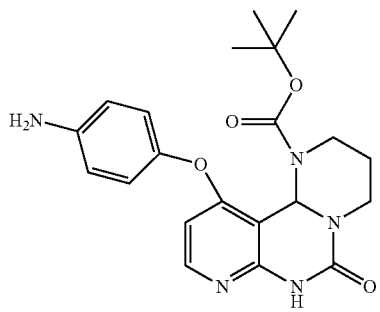 [SMILES: CC(C)(C)OC(=O)N1CCCN2C(=O)Nc3nccc(Oc4ccc(N)cc4)c3C21]

tert-butyl 11-(4-aminophenoxy)-6-oxo-3,4,7,11b-tetrahydro-2H-pyrido[3,2-e]pyrimido[1,2-c]pyrimidine-1(6H)-carboxylate (78)

The title compound was synthesized according to the procedure described for the preparation of Example 57 using 77 and 4-aminophenol. LC-MS (M+H=412, obsd.=412).

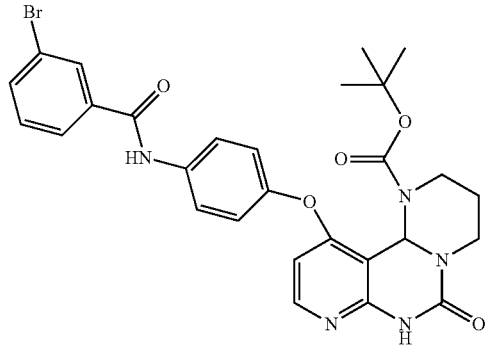 [SMILES: CC(C)(C)OC(=O)N1CCCN2C(=O)Nc3nccc(Oc4ccc(NC(=O)c5cccc(Br)c5)cc4)c3C21]

tert-butyl 11-{4-[(3-bromobenzoyl)amino]phenoxy}-6-oxo-3,4,7,11b-tetrahydro-2H-pyrido[3,2-e]pyrimido[1,2-c]pyrimidine-1(6H)-carboxylate (79)

The title compound was synthesized according to the procedure described for the preparation of Example 60 using 78 and 3-bromo benzoylchloride. LC-MS (M+H=595, obsd.=595).

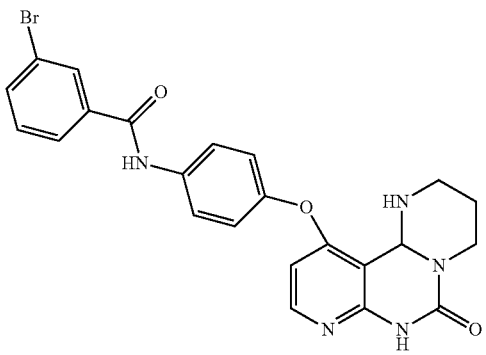 [SMILES: O=C(Nc1ccc(Oc2ccnc3c2C2NCCCN2C(=O)N3)cc1)c1cccc(Br)c1]

3-bromo-N-{4-[(6-oxo-1,3,4,6,7,11b-hexahydro-2H-pyrido[3,2-e]pyrimido[1,2-c]pyrimidin-11-yl)oxy]phenyl}benzamide (80)

The title compound was synthesized by de-protection of 79 by HCl in MeOH. LC-MS (M+H=495, obsd.=495).

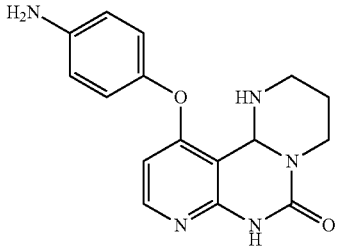 [SMILES: Nc1ccc(Oc2ccnc3c2C2NCCCN2C(=O)N3)cc1]

11-(4-aminophenoxy)-1,2,3,4,7,11b-hexahydro-6H-pyrido[3,2-e]pyrimido[1,2-c]pyrimidin-6-one (81)

The title compound was synthesized by de-protection of 78 by HCl in MeOH. LC-MS (M+H=312, obsd.=312).

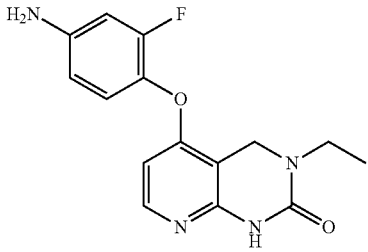 [SMILES: CCN1Cc2c(Oc3ccc(N)cc3F)ccnc2NC1=O]

5-(4-amino-2-fluorophenoxy)-3-ethyl-3,4-dihydropyrido[2,3-d]pyrimidin-2(1H)-one (82)

The title compound was synthesized according to the procedure described for the preparation of Example 57 using 33 and 4-amino-2-fluoro-phenol. LC-MS (M+H=303, obsd.=303).

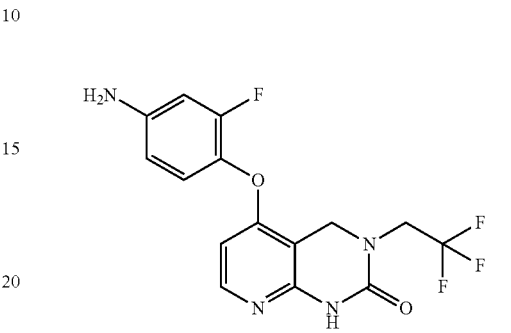

5-(4-amino-2-fluorophenoxy)-3-(2,2,2-trifluoroethyl)-3,4-dihydropyrido[2,3-d]pyrimidin-2(1H)-one (83)

The title compound was synthesized according to the procedure described for the preparation of Example 57 using the scaffold from example 37 and 4-amino-2-fluoro-phenol. LC-MS (M+H=357, obsd.=357).

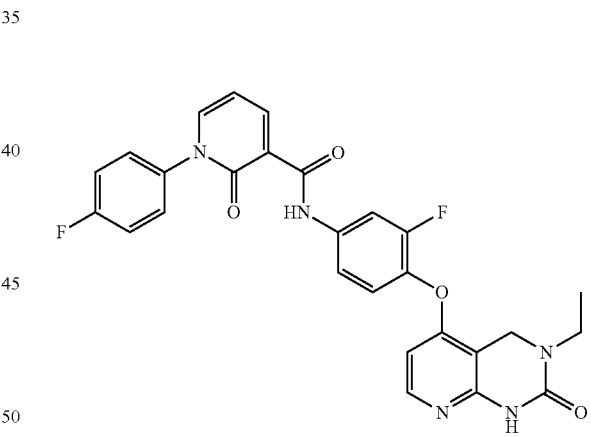

IC$_{50}$ (RON) "+++"

N-{4-[(3-ethyl-2-oxo-1,2,3,4-tetrahydropyrido[2,3-d]pyrimidin-5-yl)oxy]-3-fluorophenyl}-1-(4-fluorophenyl)-2-oxo-1,2-dihydropyridine-3-carboxamide (84)

The title compound was synthesized according to the procedure described for the preparation of Example 57 using 33 and 1-(4-fluoro-phenyl)-2-oxo-1,2-dihydro-pyridine-3-carboxylic acid (3-fluoro-4-hydroxy-phenyl)-amide. LC-MS (M+H=518, obsd.=518).

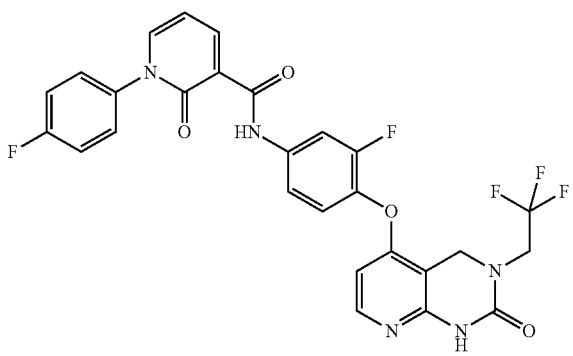 [SMILES: O=C(Nc1ccc(Oc2ccnc3c2CN(CC(F)(F)F)C(=O)N3)c(F)c1)c1cccn(-c2ccc(F)cc2)c1=O]

IC$_{50}$ (RON) "++"

N-(3-fluoro-4-{[2-oxo-3-(2,2,2-trifluoroethyl)-1,2,3,4-tetrahydropyrido[2,3-d]pyrimidin-5-yl]oxy}phenyl)-1-(4-fluorophenyl)-2-oxo-1,2-dihydropyridine-3-carboxamide (85)

The title compound was synthesized according to the procedure described for the preparation of Example 57 using the scaffold from example 37 and 1-(4-fluoro-phenyl)-2-oxo-1,2-dihydro-pyridine-3-carboxylic acid (3-fluoro-4-hydroxyphenyl)-amide. LC-MS (M+H=572, obsd.=572).

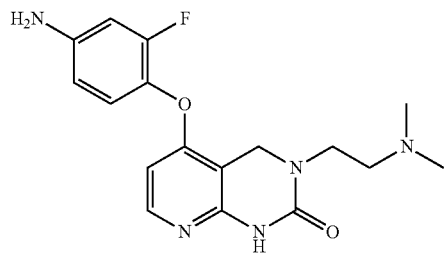 [SMILES: CN(C)CCN1Cc2c(Oc3ccc(N)cc3F)ccnc2NC1=O]

5-(4-amino-2-fluorophenoxy)-3-[2-(dimethylamino)ethyl]-3,4-dihydropyrido[2,3-d]pyrimidin-2(1H)-one (86)

The title compound was synthesized according to the procedure described for the preparation of Example 57 using 10 and 4-amino-2-fluoro-phenol. LC-MS (M+H=346, obsd.=346).

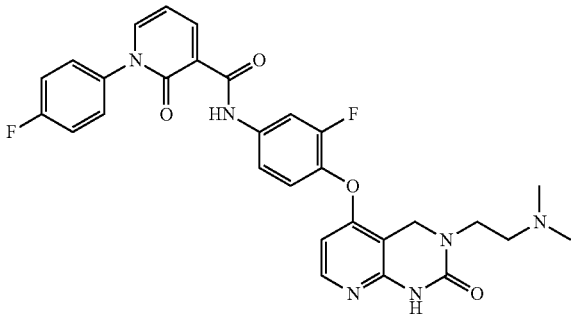 [SMILES: CN(C)CCN1Cc2c(Oc3ccc(NC(=O)c4cccn(-c5ccc(F)cc5)c4=O)cc3F)ccnc2NC1=O]

N-[4-({3-[2-(dimethylamino)ethyl]-2-oxo-1,2,3,4-tetrahydropyrido[2,3-d]pyrimidin-5-yl}oxy)-3-fluorophenyl]-1-(4-fluorophenyl)-2-oxo-1,2-dihydropyridine-3-carboxamide (87)

The title compound was synthesized according to the procedure described for the preparation of Example 61 using 86 and 1-(4-fluoro-phenyl)-2-oxo-1,2-dihydro-pyridine-3-carboxylic acid. LC-MS (M+H=561, obsd.=561).

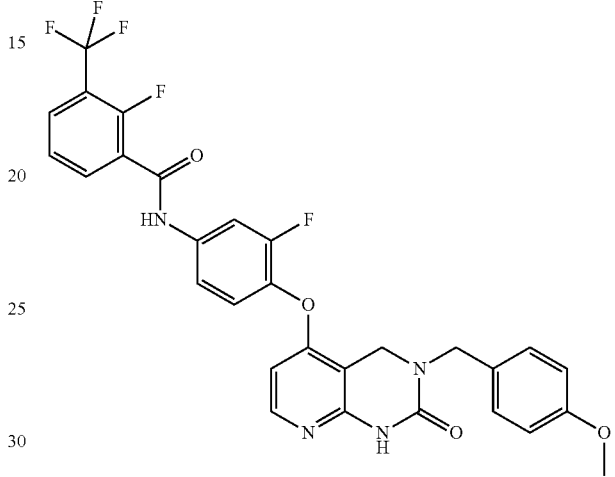

2-fluoro-N-(3-fluoro-4-{[3-(4-methoxybenzyl)-2-oxo-1,2,3,4-tetrahydropyrido[2,3-d]pyrimidin-5-yl]oxy}phenyl)-3-(trifluoromethyl)benzamide (88)

The title compound was synthesized according to the procedure described for the preparation of Example 60 using 57 and 2-fluoro-3-trifluoromethyl-benzoyl chloride. LC-MS (M+H=585, obsd.=585).

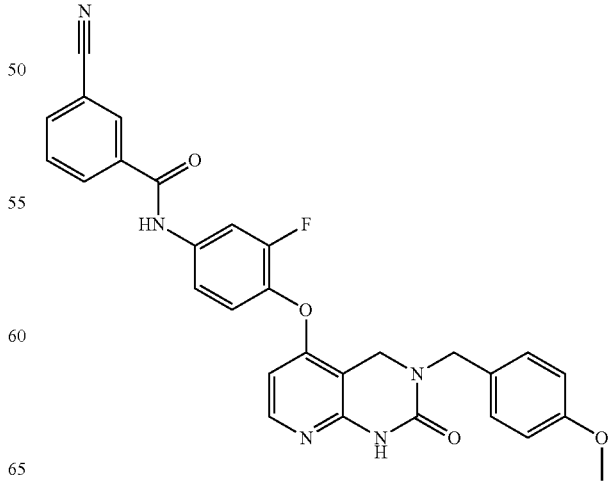

3-cyano-N-(3-fluoro-4-{[3-(4-methoxybenzyl)-2-oxo-1,2,3,4-tetrahydropyrido[2,3-d]pyrimidin-5-yl]oxy}phenyl)benzamide (89)

The title compound was synthesized according to the procedure described for the preparation of Example 60 using 57 and 3-cyano-benzoyl chloride. LC-MS (M+H=524, obsd.=524).

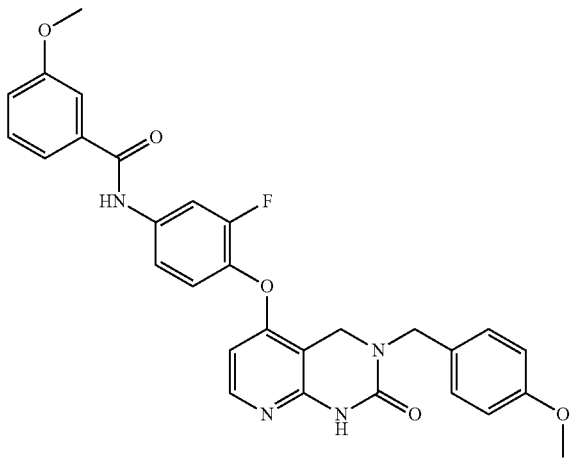 [SMILES: COc1ccc(CN2Cc3c(Oc4ccc(NC(=O)c5cccc(OC)c5)cc4F)ccnc3NC2=O)cc1]

N-(3-fluoro-4-{[3-(4-methoxybenzyl)-2-oxo-1,2,3,4-tetrahydropyrido[2,3-d]pyrimidin-5-yl]oxy}phenyl)-3-methoxybenzamide (90)

The title compound was synthesized according to the procedure described for the preparation of Example 60 using 57 and 3-methoxy-benzoyl chloride. LC-MS (M+H=529, obsd.=529).

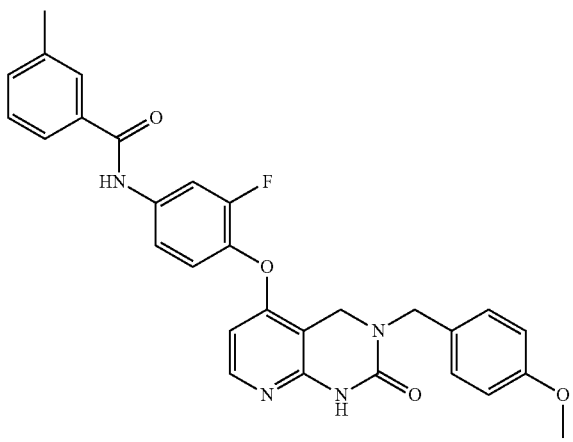 [SMILES: COc1ccc(CN2Cc3c(Oc4ccc(NC(=O)c5cccc(C)c5)cc4F)ccnc3NC2=O)cc1]

N-(3-fluoro-4-{[3-(4-methoxybenzyl)-2-oxo-1,2,3,4-tetrahydropyrido[2,3-d]pyrimidin-5-yl]oxy}phenyl)-3-methylbenzamide (91)

The title compound was synthesized according to the procedure described for the preparation of Example 60 using 57 and 3-methyl-benzoyl chloride. LC-MS (M+H=513, obsd.=513).

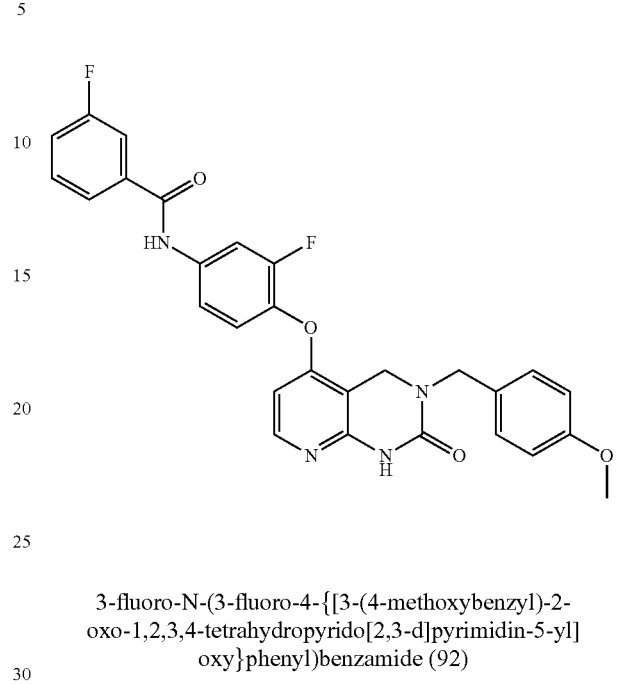

3-fluoro-N-(3-fluoro-4-{[3-(4-methoxybenzyl)-2-oxo-1,2,3,4-tetrahydropyrido[2,3-d]pyrimidin-5-yl]oxy}phenyl)benzamide (92)

The title compound was synthesized according to the procedure described for the preparation of Example 60 using 57 and 3-fluoro-benzoyl chloride. LC-MS (M+H=517, obsd.=517).

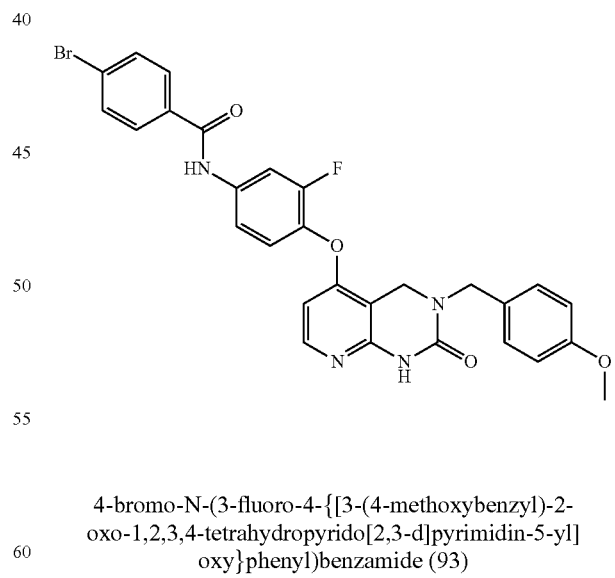

4-bromo-N-(3-fluoro-4-{[3-(4-methoxybenzyl)-2-oxo-1,2,3,4-tetrahydropyrido[2,3-d]pyrimidin-5-yl]oxy}phenyl)benzamide (93)

The title compound was synthesized according to the procedure described for the preparation of Example 60 using 57 and 4-bromo-benzoyl chloride. LC-MS (M+H=578, obsd.=578).

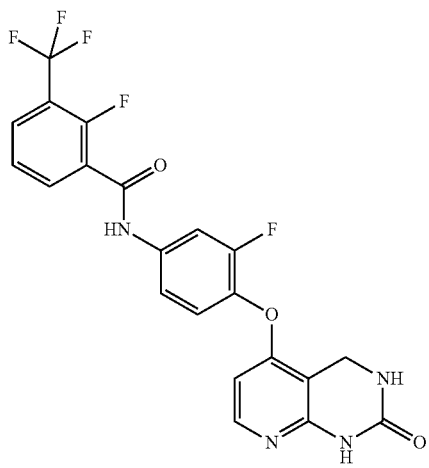 [SMILES: O=C1NCc2c(Oc3ccc(NC(=O)c4cccc(C(F)(F)F)c4F)cc3F)ccnc2N1]

IC$_{50}$ (RON) "++"

2-fluoro-N-{3-fluoro-4-[(2-oxo-1,2,3,4-tetrahydro-pyrido[2,3-d]pyrimidin-5-yl)oxy]phenyl}-3-(trifluoromethyl)benzamide (94)

The title compound was synthesized according to the procedure described for the preparation of Example 3 using 88. LC-MS (M+H=465, obsd.=465).

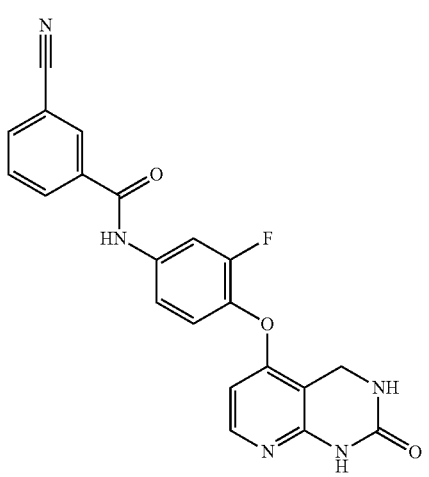 [SMILES: N#Cc1cccc(C(=O)Nc2ccc(Oc3ccnc4c3CNC(=O)N4)c(F)c2)c1]

IC$_{50}$ (RON) "++"

3-cyano-N-{3-fluoro-4-[(2-oxo-1,2,3,4-tetrahydro-pyrido[2,3-d]pyrimidin-5-yl)oxy]phenyl}benzamide (95)

The title compound was synthesized according to the procedure described for the preparation of Example 3 using 89. LC-MS (M+H=404, obsd.=404).

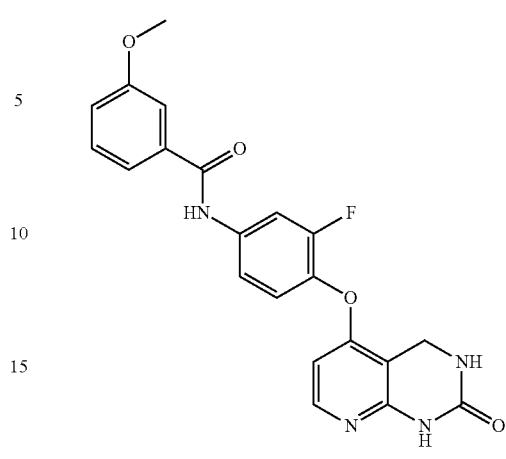

IC$_{50}$ (RON) "++"

N-{3-fluoro-4-[(2-oxo-1,2,3,4-tetrahydropyrido[2,3-d]pyrimidin-5-yl)oxy]phenyl}-3-methoxybenzamide (96)

The title compound was synthesized according to the procedure described for the preparation of Example 3 using 90. LC-MS (M+H=409, obsd.=409).

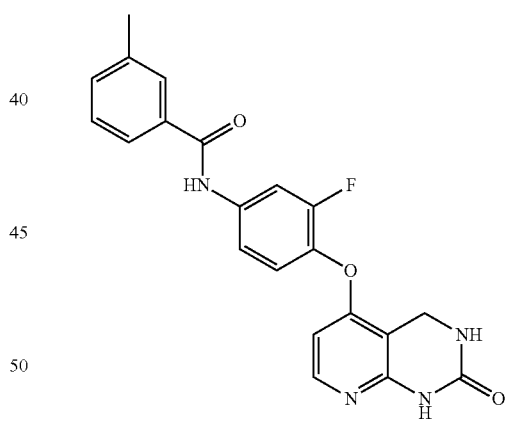

IC$_{50}$ (RON) "++"

N-{3-fluoro-4-[(2-oxo-1,2,3,4-tetrahydropyrido[2,3-d]pyrimidin-5-yl)oxy]phenyl}-3-methylbenzamide (97)

The title compound was synthesized according to the procedure described for the preparation of Example 3 using 91. LC-MS (M+H=393, obsd.=393).

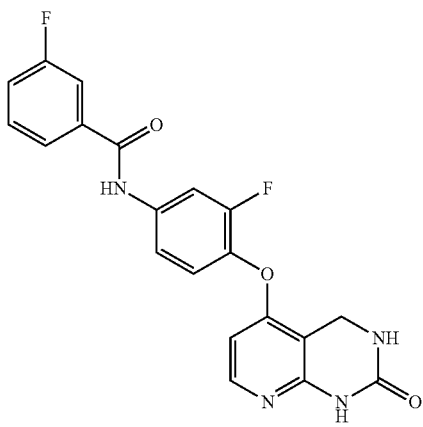

IC$_{50}$ (RON) "++"

3-fluoro-N-{3-fluoro-4-[(2-oxo-1,2,3,4-tetrahydro-pyrido[2,3-d]pyrimidin-5-yl)oxy]phenyl}benzamide (98)

The title compound was synthesized according to the procedure described for the preparation of Example 3 using 92. LC-MS (M+H=397, obsd.=397).

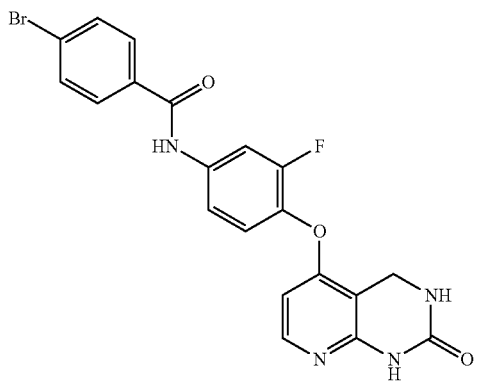 [SMILES: O=C1NCc2c(Oc3ccc(NC(=O)c4ccc(Br)cc4)cc3F)ccnc2N1]

IC$_{50}$ (RON) "+++"

4-bromo-N-{3-fluoro-4-[(2-oxo-1,2,3,4-tetrahydro-pyrido[2,3-d]pyrimidin-5-yl)oxy]phenyl}benzamide (99)

The title compound was synthesized according to the procedure described for the preparation of Example 3 using 93. LC-MS (M+H=458, obsd.=458).

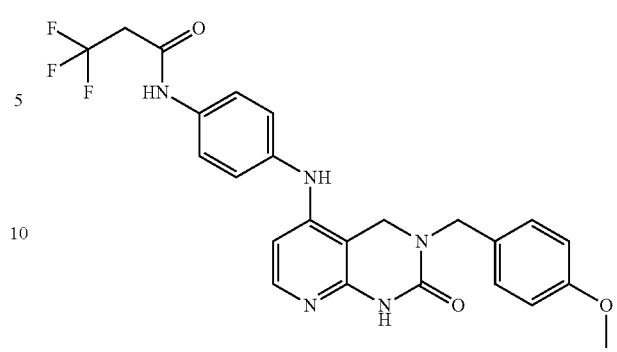

IC$_{50}$ (AK) "+"

3,3,3-trifluoro-N-(4-{[3-(4-methoxybenzyl)-2-oxo-1,2,3,4-tetrahydropyrido[2,3-d]pyrimidin-5-yl]amino}phenyl)propanamide (100)

1 (52 mg, 0.17 mmol), N-(4-aminophenyl)-3,3,3-trifluoropropanamide (44 mg, 0.17 mmol), and HCl (43 µL, 4.0M in dioxane, 0.17 mmol) were suspended in NMP (1 mL), and stirred in a microwave at 150° C. for 100 min. The crude product was purified directly via HPLC to provide 100 (39% yield). LC-MS (M+H=486, obsd.=486).

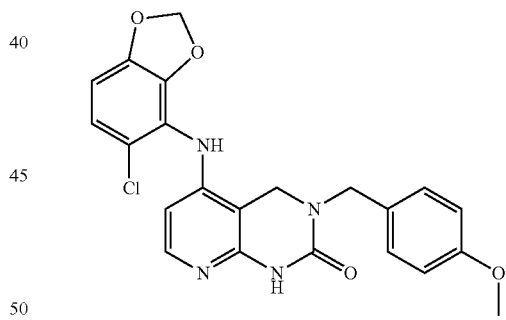

5-[(5-chloro-1,3-benzodioxol-4-yl)amino]-3-(4-methoxybenzyl)-3,4-dihydropyrido[2,3-d]pyrimidin-2(1H)-one (101)

1 (69 mg, 0.23 mmol), 5-chloro-1,3-benzodioxol-4-amine (47 mg, 0.27 mmol), Pd(OAc)$_2$ (2.5 mg, 0.01 mmol), X-Phos (11 mg, 0.02 mmol), and NaOtBu (65 mg, 0.68 mmol) were suspended in anhydrous dioxane (2 mL), and stirred in a microwave at 120° C. for 150 min. The crude product was purified directly via HPLC to provide 101 (35% yield). LC-MS (M+H=439, obsd.=439).

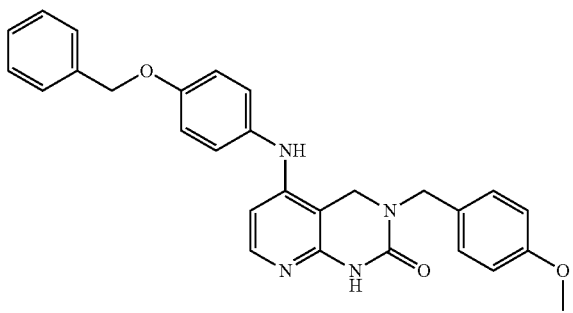 [SMILES: COc1ccc(CN2Cc3c(Nc4ccc(OCc5ccccc5)cc4)ccnc3NC2=O)cc1]

5-{[4-(benzyloxy)phenyl]amino}-3-(4-methoxybenzyl)-3,4-dihydropyrido[2,3-d]pyrimidin-2(1H)-one (102)

The title compound was synthesized according to the procedure described for the preparation of Example 100 using 1 and 4-benzyloxy-phenylamine. LC-MS (M+H=467, obsd.=467).

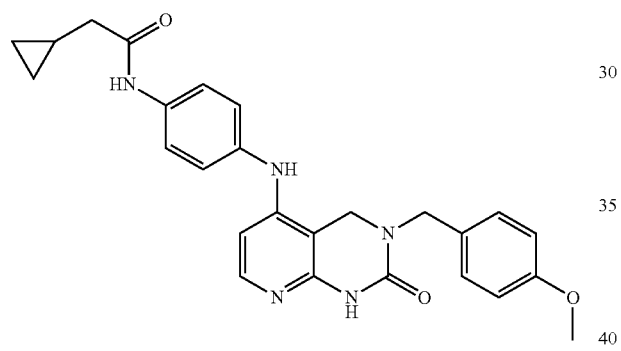

2-cyclopropyl-N-(4-{[3-(4-methoxybenzyl)-2-oxo-1,2,3,4-tetrahydropyrido[2,3-d]pyrimidin-5-yl]amino}phenyl)acetamide (103)

The title compound was synthesized according to the procedure described for the preparation of Example 100 using 1 and N-(4-amino-phenyl)-2-cyclopropyl-acetamide. LC-MS (M+H=458, obsd.=458).

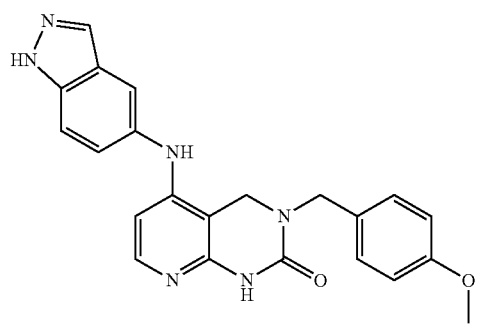 [SMILES: COc1ccc(CN2Cc3c(Nc4ccc5[nH]ncc5c4)ccnc3NC2=O)cc1]

5-(1H-indazol-5-ylamino)-3-(4-methoxybenzyl)-3,4-dihydropyrido[2,3-d]pyrimidin-2(1H)-one (104)

The title compound was synthesized according to the procedure described for the preparation of Example 100 using 1 and 1H-indazol-5-ylamine. LC-MS (M+H=401, obsd.=401).

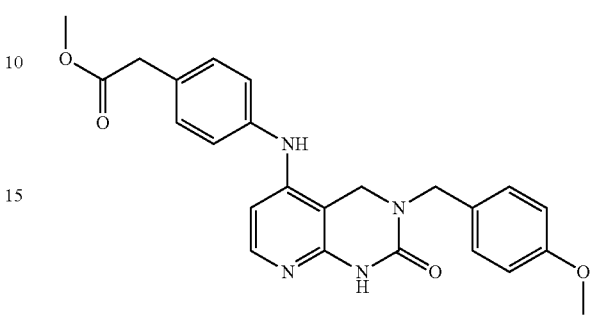

methyl (4-{[3-(4-methoxybenzyl)-2-oxo-1,2,3,4-tetrahydropyrido[2,3-d]pyrimidin-5-yl]amino}phenyl)acetate (105)

The title compound was synthesized according to the procedure described for the preparation of Example 100 using 1 and (4-amino-phenyl)-acetic acid methyl ester. LC-MS (M+H=433, obsd.=433).

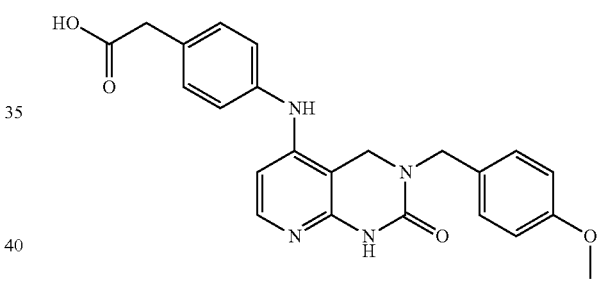

(4-{[3-(4-methoxybenzyl)-2-oxo-1,2,3,4-tetrahydropyrido[2,3-d]pyrimidin-5-yl]amino}phenyl)acetic acid (106)

The title compound was synthesized according to the procedure described for the preparation of Example 100 using 1 and (4-amino-phenyl)-acetic acid. LC-MS (M+H=419, obsd.=419).

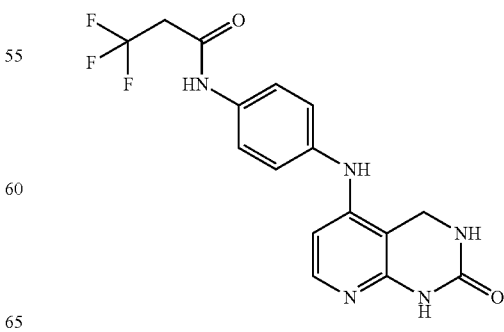

$IC_{50}$ (AK) "+"

3,3,3-trifluoro-N-{4-[(2-oxo-1,2,3,4-tetrahydropyrido[2,3-d]pyrimidin-5-yl)amino]phenyl}propanamide (107)

The title compound was synthesized according to the procedure described for the preparation of Example 3 using 100. LC-MS (M+H=366, obsd.=366).

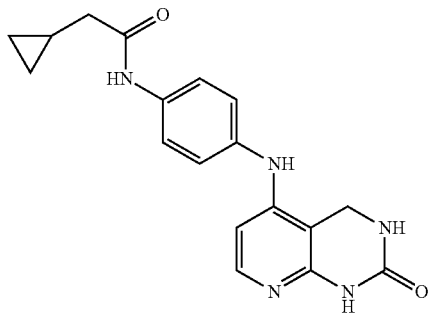 [SMILES: O=C(CC1CC1)Nc1ccc(Nc2ccnc3c2CNC(=O)N3)cc1]

IC$_{50}$ (AK) "++"

2-cyclopropyl-N-{4-[(2-oxo-1,2,3,4-tetrahydropyrido[2,3-d]pyrimidin-5-yl)amino]phenyl}acetamide (108)

The title compound was synthesized according to the procedure described for the preparation of Example 3 using 103. LC-MS (M+H=338, obsd.=338).

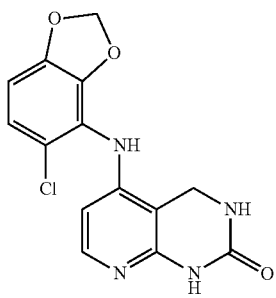 [SMILES: O=C1NCc2c(Nc3c(Cl)ccc4c3OCO4)ccnc2N1]

5-[(5-chloro-1,3-benzodioxol-4-yhamino]-3,4-dihydropyrido[2,3-d]pyrimidin-2(1H)-one (109)

The title compound was synthesized according to the procedure described for the preparation of Example 3 using 101. LC-MS (M+H=319, obsd.=319).

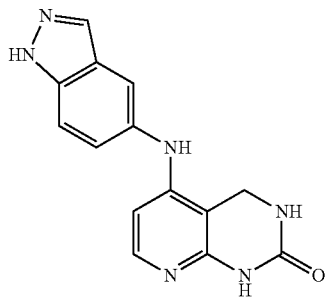 [SMILES: O=C1NCc2c(Nc3ccc4[nH]ncc4c3)ccnc2N1]

5-(1H-indazol-5-ylamino)-3,4-dihydropyrido[2,3-d]pyrimidin-2(1H)-one (110)

The title compound was synthesized according to the procedure described for the preparation of Example 3 using 104. LC-MS (M+H=281, obsd.=281).

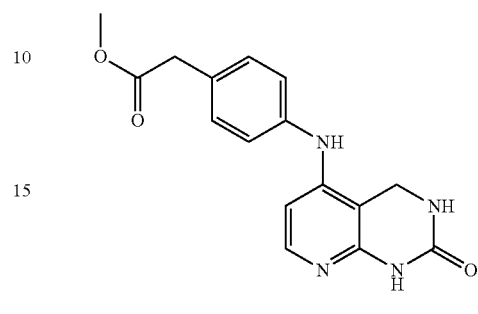

methyl {4-[(2-oxo-1,2,3,4-tetrahydropyrido[2,3-d]pyrimidin-5-yl)amino]phenyl}acetate (111)

The title compound was synthesized according to the procedure described for the preparation of Example 3 using 105. LC-MS (M+H=313, obsd.=313).

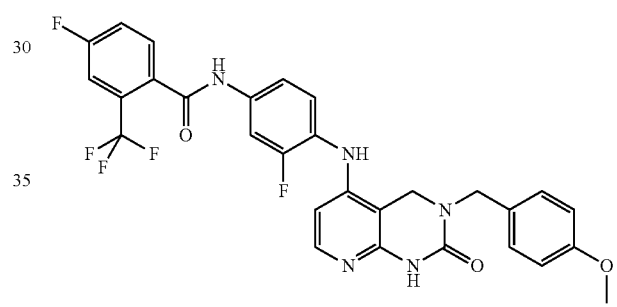

IC$_{50}$ (AK) "++"

4-fluoro-N-(3-fluoro-4-{[3-(4-methoxybenzyl)-2-oxo-1,2,3,4-tetrahydropyrido[2,3-d]pyrimidin-5-yl]amino}phenyl)-2-(trifluoromethyl)benzamide (112)

The title compound was synthesized according to the procedure described for the preparation of Example 100 using 1 and N-(4-amino-3-fluoro-phenyl)-4-fluoro-2-trifluoromethyl-benzamide. LC-MS (M+H=584, obsd.=584).

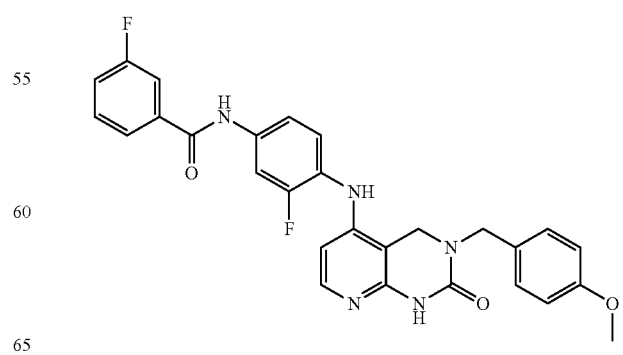

IC$_{50}$ (AK) "+"

3-fluoro-N-(3-fluoro-4-{[3-(4-methoxybenzyl)-2-oxo-1,2,3,4-tetrahydropyrido[2,3-d]pyrimidin-5-yl]amino}phenyl)benzamide (113)

The title compound was synthesized according to the procedure described for the preparation of Example 100 using 1 and N-(4-amino-3-fluoro-phenyl)-3-fluoro-benzamide. LC-MS (M+H=516, obsd.=516).

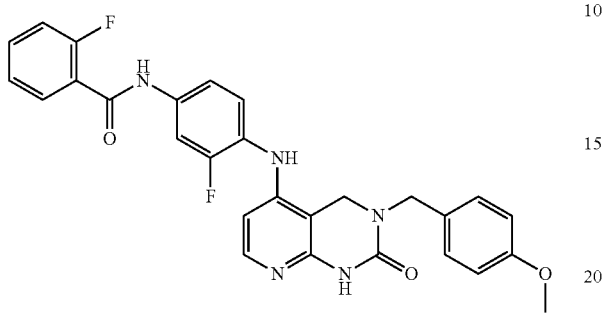

IC$_{50}$ (AK) "+"

2-fluoro-N-(3-fluoro-4-{[3-(4-methoxybenzyl)-2-oxo-1,2,3,4-tetrahydropyrido[2,3-d]pyrimidin-5-yl]amino}phenyl)benzamide (114)

The title compound was synthesized according to the procedure described for the preparation of Example 100 using 1 and N-(4-amino-3-fluoro-phenyl)-2-fluoro-benzamide. LC-MS (M+H=516, obsd.=516).

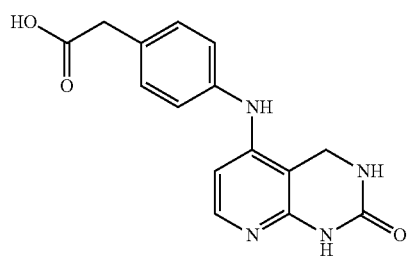 [SMILES: O=C(O)Cc1ccc(Nc2ccnc3c2CNC(=O)N3)cc1]

{4-[(2-oxo-1,2,3,4-tetrahydropyrido[2,3-d]pyrimidin-5-yl)amino]phenyl}acetic acid (115)

The title compound was synthesized according to the procedure described for the preparation of Example 3 using 106. LC-MS (M+H=299, obsd.=299).

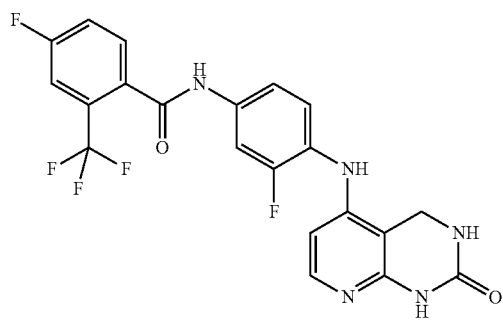 [SMILES: O=C1NCc2c(Nc3ccc(NC(=O)c4ccc(F)cc4C(F)(F)F)cc3F)ccnc2N1]

IC$_{50}$ (AK) "+++"

4-fluoro-N-{3-fluoro-4-[(2-oxo-1,2,3,4-tetrahydropyrido[2,3-d]pyrimidin-5-yl)amino]phenyl}-2-(trifluoromethyl)benzamide (116)

The title compound was synthesized according to the procedure described for the preparation of Example 3 using 112. LC-MS (M+H=464, obsd.=464).

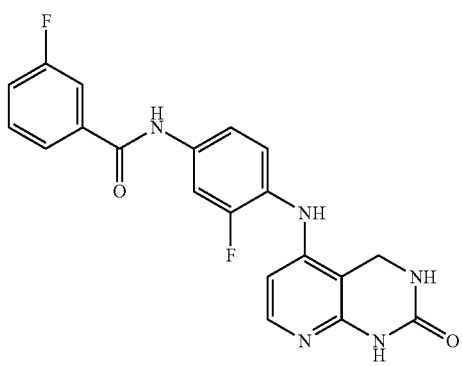 [SMILES: O=C1NCc2c(Nc3ccc(NC(=O)c4cccc(F)c4)cc3F)ccnc2N1]

IC$_{50}$ (AK) "++"

3-fluoro-N-{3-fluoro-4-[(2-oxo-1,2,3,4-tetrahydropyrido[2,3-d]pyrimidin-5-yl)amino]phenyl}benzamide (117)

The title compound was synthesized according to the procedure described for the preparation of Example 3 using 113. LC-MS (M+H=396, obsd.=396).

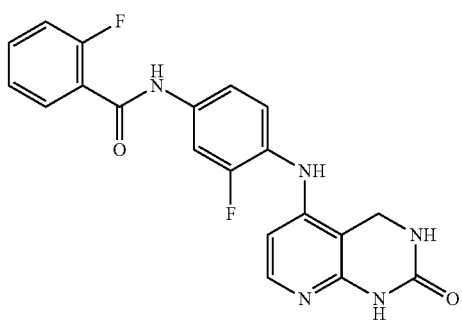 [SMILES: O=C1NCc2c(Nc3ccc(NC(=O)c4ccccc4F)cc3F)ccnc2N1]

IC$_{50}$ (AK) "++"

2-fluoro-N-{3-fluoro-4-[(2-oxo-1,2,3,4-tetrahydropyrido[2,3-d]pyrimidin-5-yl)amino]phenyl}benzamide (118)

The title compound was synthesized according to the procedure described for the preparation of Example 3 using 114. LC-MS (M+H=396, obsd.=396).

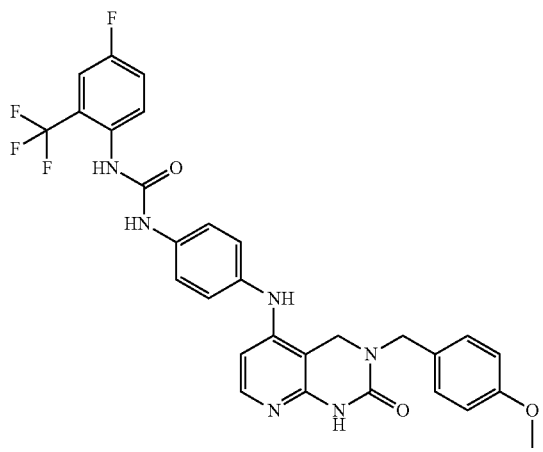 [SMILES: COc1ccc(CN2Cc3c(Nc4ccc(NC(=O)Nc5ccc(F)cc5C(F)(F)F)cc4)ccnc3NC2=O)cc1]

IC$_{50}$ (AK) "+"

N-[4-fluoro-2-(trifluoromethyl)phenyl]-N'-(4-{[3-(4-methoxybenzyl)-2-oxo-1,2,3,4-tetrahydropyrido[2,3-d]pyrimidin-5-yl]amino}phenyl)urea (119)

The title compound was synthesized according to the procedure described for the preparation of Example 63 using 5-[(Z)-4-amino-1-eth-(E)-ylidene-penta-2,4-dienylamino]-3-(4-methoxy-benzyl)-3,4-dihydro-1H-pyrido[2,3-d]pyrimidin-2-one and 4-fluoro-1-isocyanato-2-trifluoromethyl-benzene. LC-MS (M+H=581, obsd.=581).

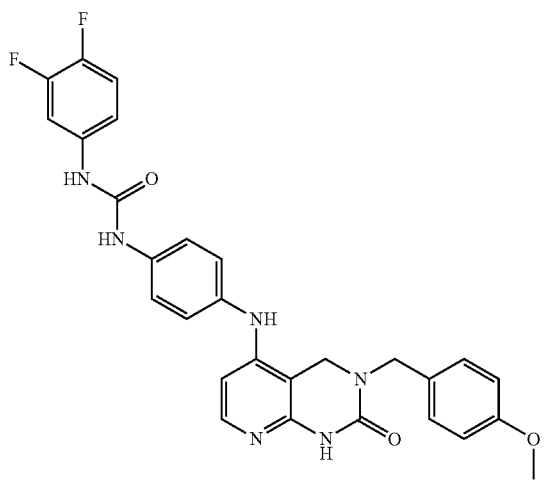 [SMILES: COc1ccc(CN2Cc3c(Nc4ccc(NC(=O)Nc5ccc(F)c(F)c5)cc4)ccnc3NC2=O)cc1]

IC$_{50}$ (AK) "+"

N-(3,4-difluorophenyl)-N'-(4-{[3-(4-methoxybenzyl)-2-oxo-1,2,3,4-tetrahydropyrido[2,3-d]pyrimidin-5-yl]amino}phenyl)urea (120)

The title compound was synthesized according to the procedure described for the preparation of Example 63 using 5-[(Z)-4-amino-1-eth-(E)-ylidene-penta-2,4-dienylamino]-3-(4-methoxy-benzyl)-3,4-dihydro-1H-pyrido[2,3-d]pyrimidin-2-one and 1,2-difluoro-4-isocyanato-benzene. LC-MS (M+H=531, obsd.=531).

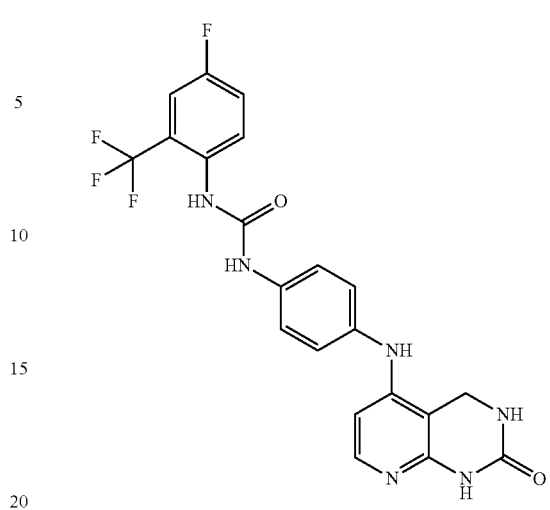

IC$_{50}$ (AK) "++"

N-[4-fluoro-2-(trifluoromethyl)phenyl]-N'-{4-[(2-oxo-1,2,3,4-tetrahydropyrido[2,3-d]pyrimidin-5-yl)amino]phenyl}urea (121)

The title compound was synthesized according to the procedure described for the preparation of Example 3 using 119. LC-MS (M+H=461, obsd.=461).

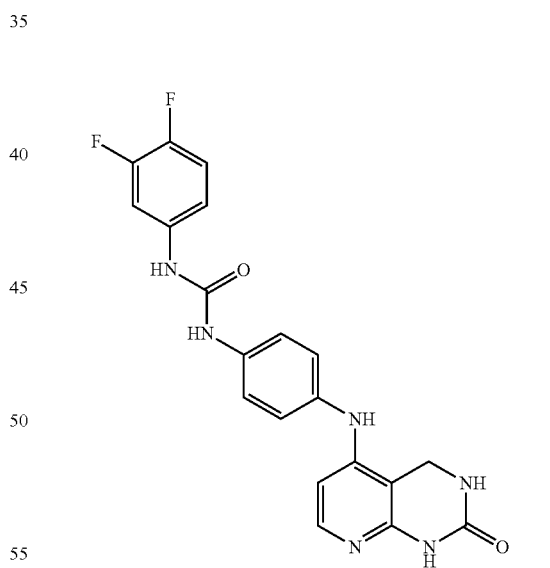

N-(3,4-difluorophenyl)-N'-{4-[(2-oxo-1,2,3,4-tetrahydropyrido[2,3-d]pyrimidin-5-yl)amino]phenyl}urea (122)

The title compound was synthesized according to the procedure described for the preparation of Example 3 using 120. LC-MS (M+H=411, obsd.=411).

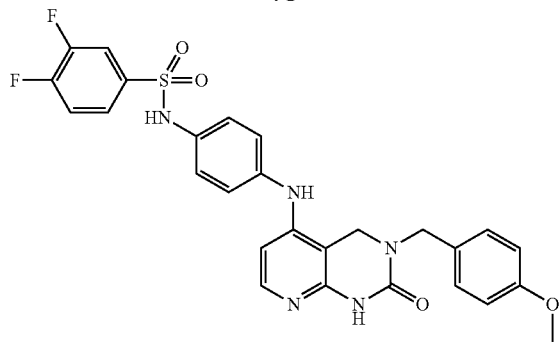

3,4-difluoro-N-(4-{[3-(4-methoxybenzyl)-2-oxo-1,2,3,4-tetrahydropyrido[2,3-d]pyrimidin-5-yl]amino}phenyl)benzenesulfonamide (123)

The title compound was synthesized according to the procedure described for the preparation of Example 62 using 5-[(Z)-4-amino-1-eth-(E)-ylidene-penta-2,4-dienylamino]-3-(4-methoxy-benzyl)-3,4-dihydro-1 H-pyrido[2,3-d]pyrimidin-2-one and 3,4-difluoro-benzenesulfonyl chloride. LC-MS (M+H=552, obsd.=552).

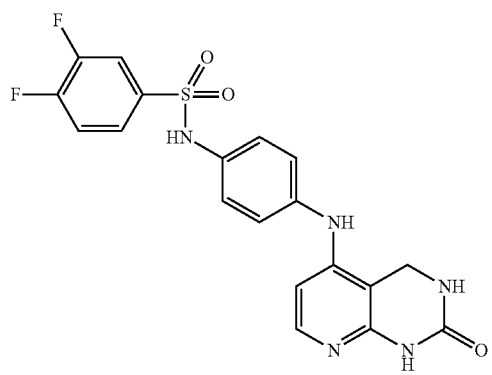 [SMILES: O=C1NCc2c(Nc3ccc(NS(=O)(=O)c4ccc(F)c(F)c4)cc3)ccnc2N1]

3,4-difluoro-N-{4-[(2-oxo-1,2,3,4-tetrahydropyrido[2,3-d]pyrimidin-5-yl)amino]phenyl}benzenesulfonamide (124)

The title compound was synthesized according to the procedure described for the preparation of Example 3 using 123. LC-MS (M+H=432, obsd.=432).

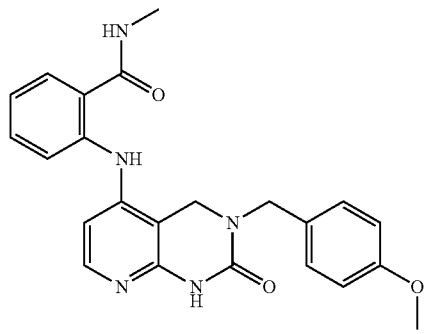 [SMILES: CNC(=O)c1ccccc1Nc1ccnc2c1CN(Cc1ccc(OC)cc1)C(=O)N2]

2-{[3-(4-methoxybenzyl)-2-oxo-1,2,3,4-tetrahydrocyrido[2,3-d]pyrimidin-5-yl]amino}-N-methylbenzamide (125)

The title compound was synthesized according to the procedure described for the preparation of Example 101 using 1 and 2-amino-N-methyl-benzamide. LC-MS (M+H=418, obsd.=418).

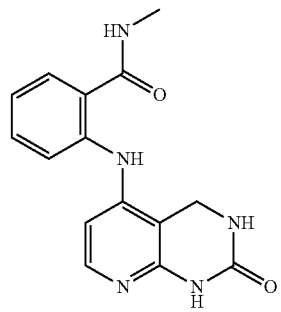 [SMILES: CNC(=O)c1ccccc1Nc1ccnc2c1CNC(=O)N2]

N-methyl-2-[(2-oxo-1,2,3,4-tetrahydropyrido[2,3-d]pyrimidin-5-yl)amino]benzamide (126)

The title compound was synthesized according to the procedure described for the preparation of Example 3 using 125. LC-MS (M+H=298, obsd.=298).

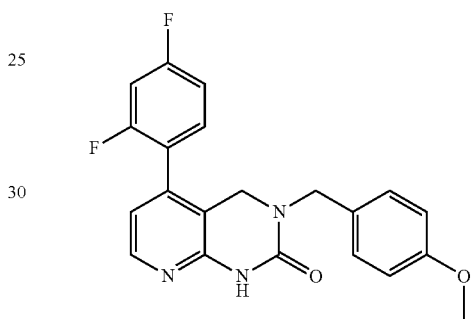

5-(2,4-difluorophenyl)-3-(4-methoxybenzyl)-3,4-dihydropyrido[2,3-d]pyrimidin-2(1H)-one (127)

1 (65 mg, 0.21 mmol), 2,4-difluorophenylboronic acid (101 mg, 0.64 mmol), Pd(OAc)$_2$ (5 mg, 0.02 mmol), S-Phos (18 mg, 0.04 mmol), and K$_2$CO$_3$ (88 mg; 0.64 mmol) were suspended in dioxane (2 mL), and stirred overnight at 100° C. The crude product was purified directly via HPLC to provide 127 (7% yield). LC-MS (M+H=382, obsd.=382).

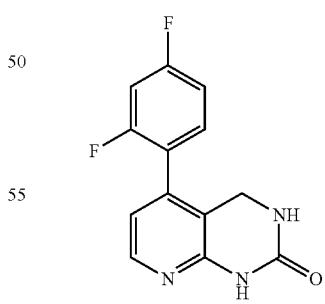

5-(2,4-difluorophenyl)-3,4-dihydropyrido[2,3-d]pyrimidin-2(1H)-one (128)

The title compound was synthesized according to the procedure described for the preparation of Example 3 using 127. LC-MS (M+H=262, obsd.=262).

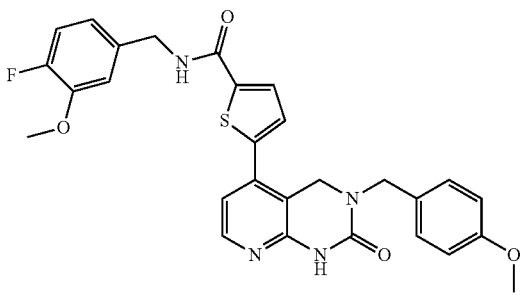 [SMILES: COc1ccc(CN2Cc3c(-c4ccc(C(=O)NCc5ccc(F)c(OC)c5)s4)ccnc3NC2=O)cc1]

IC$_{50}$ (AK) "++"

N-(4-fluoro-3-methoxybenzyl)-5-[3-(4-methoxybenzyl)-2-oxo-1,2,3,4-tetrahydropyrido[2,3-d]pyrimidin-5-yl]thiophene-2-carboxamide (129)

The title compound was synthesized according to the procedure described for the preparation of Example 127 using 1. LC-MS (M+H=533, obsd.=533).

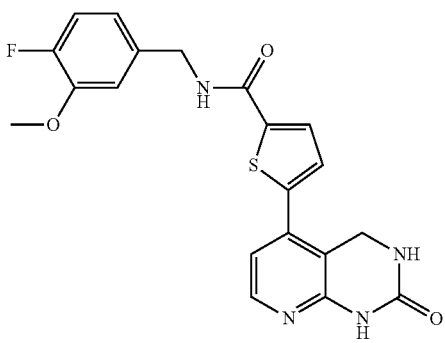 [SMILES: COc1cc(CNC(=O)c2ccc(-c3ccnc4c3CNC(=O)N4)s2)ccc1F]

IC$_{50}$ (AK) "++"

N-(4-fluoro-3-methoxybenzyl)-5-(2-oxo-1,2,3,4-tetrahydropyrido[2,3-d]pyrimidin-5-yl)thiophene-2-carboxamide (130)

The title compound was synthesized according to the procedure described for the preparation of Example 3 using 129. LC-MS (M+H=413, obsd.=413).

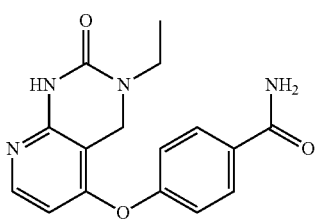 [SMILES: CCN1Cc2c(Oc3ccc(C(N)=O)cc3)ccnc2NC1=O]

4-(3-Ethyl-2-oxo-1,2,3,4-tetrahydro-pyrido[2,3-d]pyrimidin-5-yloxy)-benzamide (131)

The title compound was synthesized according to the procedure described for the preparation of Example 57 using 33 and 4-hydroxy-benzamide. LC-MS (M+1=313, obsd.=313).

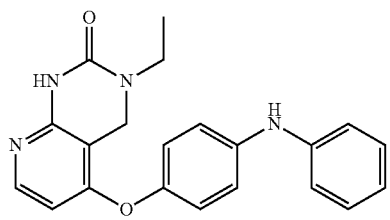 [SMILES: CCN1Cc2c(Oc3ccc(Nc4ccccc4)cc3)ccnc2NC1=O]

3-Ethyl-5-(4-phenylamino-phenoxy)-3,4-dihydro-1H-pyrido[2,3-d]pyrimidin-2-one (132)

The title compound was synthesized according to the procedure described for the preparation of Example 57 using 33 and 4-phenylamino-phenol. LC-MS (M+1=361, obsd.=361).

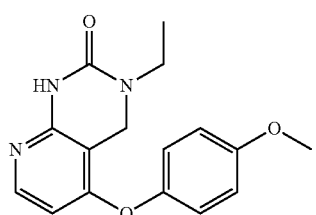

3-Ethyl-5-(4-methoxy-phenoxy)-3,4-dihydro-1H-pyrido[2,3-d]pyrimidin-2-one (133)

The title compound was synthesized according to the procedure described for the preparation of Example 57 using 33 and 4-methoxy-phenol. LC-MS (M+1=300, obsd.=300).

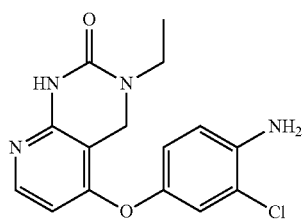 [SMILES: CCN1Cc2c(Oc3ccc(N)c(Cl)c3)ccnc2NC1=O]

5-(4-Amino-3-chloro-phenoxy)-3-ethyl-3,4-dihydro-1H-pyrido[2,3-d]pyrimidin-2-one (134)

The title compound was synthesized according to the procedure described for the preparation of Example 57 using 33 and 4-amino-3-chloro-phenol. LC-MS (M+1=319, obsd.=319).

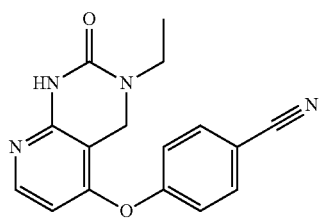 [SMILES: CCN1Cc2c(Oc3ccc(C#N)cc3)ccnc2NC1=O]

4-(3-Ethyl-2-oxo-1,2,3,4-tetrahydro-pyrido[2,3-d]pyrimidin-5-yloxy)-benzonitrile (135)

The title compound was synthesized according to the procedure described for the preparation of Example 57 using 33 and 4-hydroxy-benzonitrile. LC-MS (M+1=295, obsd.=295).

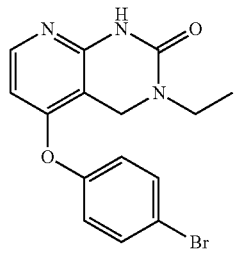 [SMILES: CCN1Cc2c(Oc3ccc(Br)cc3)ccnc2NC1=O]

5-(4-Bromo-phenoxy)-3-ethyl-3,4-dihydro-1H-pyrido[2,3-d]pyrimidin-2-one (136)

The title compound was synthesized according to the procedure described for the preparation of Example 57 using 33 and 4-bromophenol. LC-MS (M+1=348, obsd.=348).

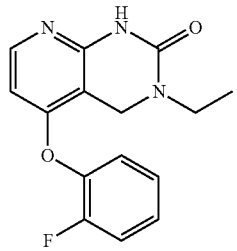 [SMILES: CCN1Cc2c(Oc3ccccc3F)ccnc2NC1=O]

3-Ethyl-5-(2-fluoro-phenoxy)-3,4-dihydro-1H-pyrido[2,3-d]pyrimidin-2-one (137)

The title compound was synthesized according to the procedure described for the preparation of Example 57 using 33 and 2-fluorophenol. LC-MS (M+1=288, obsd.=288).

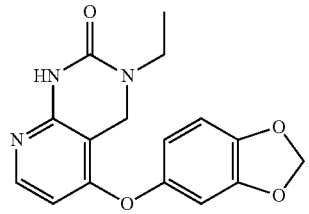 [SMILES: CCN1Cc2c(Oc3ccc4c(c3)OCO4)ccnc2NC1=O]

5-(Benzo[1,3]dioxol-5-yloxy)-3-ethyl-3,4-dihydro-1H-pyrido[2,3-d]pyrimidin-2-one (138)

The title compound was synthesized according to the procedure described for the preparation of Example 57 using 33 and benzo[1,3]dioxol-5-ol. LC-MS (M+1=314, obsd.=314).

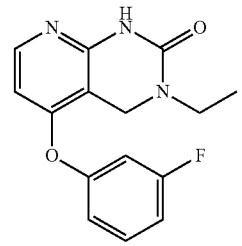 [SMILES: CCN1Cc2c(Oc3cccc(F)c3)ccnc2NC1=O]

3-Ethyl-5-(3-fluoro-phenoxy)-3,4-dihydro-1H-pyrido[2,3-d]pyrimidin-2-one (139)

The title compound was synthesized according to the procedure described for the preparation of Example 57 using 33 and 3-fluorophenol. LC-MS (M+1=288, obsd.=288).

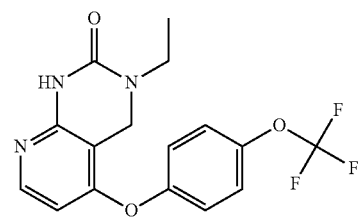 [SMILES: CCN1Cc2c(Oc3ccc(OC(F)(F)F)cc3)ccnc2NC1=O]

3-Ethyl-5-(4-trifluoromethoxy-phenoxy)-3,4-dihydro-1H-pyrido[2,3-d]pyrimidin-2-one (140)

The title compound was synthesized according to the procedure described for the preparation of Example 57 using 33 and 4-trifluoromethoxy-phenol. LC-MS (M+1=354, obsd.=354).

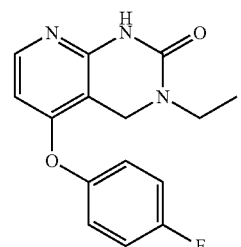

3-Ethyl-5-(4-fluoro-phenoxy)-3,4-dihydro-1H-pyrido[2,3-d]pyrimidin-2-one (141)

The title compound was synthesized according to the procedure described for the preparation of Example 57 using 33 and 4-fluorophenol. LC-MS (M+1=288, obsd.=288).

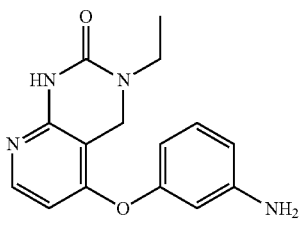 [SMILES: CCN1Cc2c(Oc3cccc(N)c3)ccnc2NC1=O]

5-(3-Amino-phenoxy)-3-ethyl-3,4-dihydro-1H-pyrido[2,3-d]pyrimidin-2-one (142)

The title compound was synthesized according to the procedure described for the preparation of Example 57 using 33 and 3-aminopheno. LC-MS (M+1=285, obsd.=285).

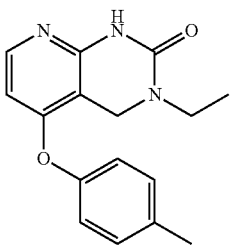 [SMILES: CCN1Cc2c(Oc3ccc(C)cc3)ccnc2NC1=O]

3-Ethyl-5-p-tolyloxy-3,4-dihydro-1H-pyrido[2,3-d]pyrimidin-2-one (143)

The title compound was synthesized according to the procedure described for the preparation of Example 57 using 33 and 4-methylphenol. LC-MS (M+1=284, obsd.=284).

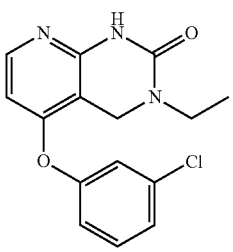

5-(3-Chloro-phenoxy)-3-ethyl-3,4-dihydro-1H-pyrido[2,3-d]pyrimidin-2-one (144)

The title compound was synthesized according to the procedure described for the preparation of Example 57 using 33 and 3-chlorophenol. LC-MS (M+1=304, obsd.=304).

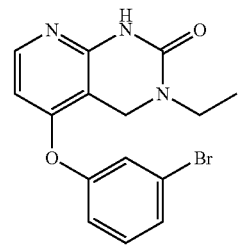 [SMILES: CCN1Cc2c(Oc3cccc(Br)c3)ccnc2NC1=O]

5-(3-Bromo-phenoxy)-3-ethyl-3,4-dihydro-1 H-pyrido[2,3-d]pyrimidin-2-one (145)

The title compound was synthesized according to the procedure described for the preparation of Example 57 using 33 and 3-bromophenol. LC-MS (M+1=348, obsd.=348).

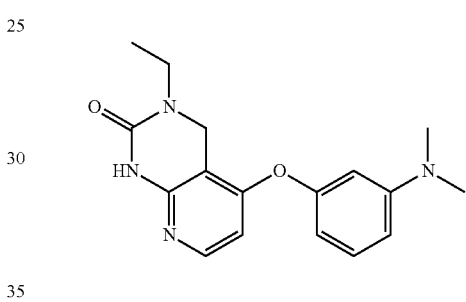

5-(3-Dimethylamino-phenoxy)-3-ethyl-3,4-dihydro-1H-pyrido[2,3-d]pyrimidin-2-one (146)

The title compound was synthesized according to the procedure described for the preparation of Example 57 using 33 and 3-dimethylaminophenol. LC-MS (M+1=313, obsd.=313).

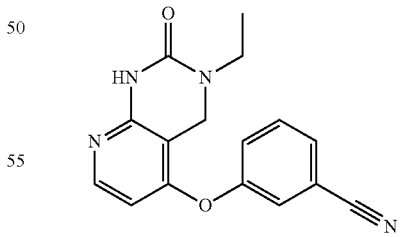

3-(3-Ethyl-2-oxo-1,2,3,4-tetrahydro-pyrido[2,3-d]pyrimidin-5-yloxy)-benzonitrile (147)

The title compound was synthesized according to the procedure described for the preparation of Example 57 using 33 and 3-hydroxy-benzonitrile. LC-MS (M+1=295, obsd.=295).

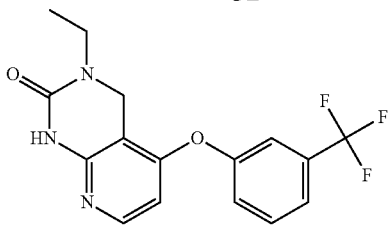

3-Ethyl-5-(3-trifluoromethyl-phenoxy)-3,4-dihydro-1H-pyrido[2,3-d]pyrimidin-2-one (148)

The title compound was synthesized according to the procedure described for the preparation of Example 57 using 33 and 3-trifluoromethoxy-phenol. LC-MS (M+1=354, obsd.=354).

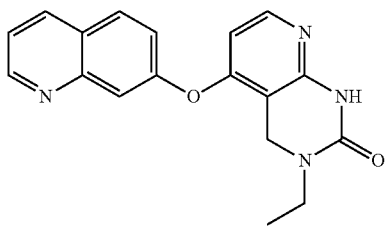 [SMILES: CCN1Cc2c(Oc3ccc4cccnc4c3)ccnc2NC1=O]

3-Ethyl-5-(quinolin-7-yloxy)-3,4-dihydro-1H-pyrido[2,3-d]pyrimidin-2-one (149)

The title compound was synthesized according to the procedure described for the preparation of Example 57 using 33 and quinolin-7-ol. LC-MS (M+1=321, obsd.=321).

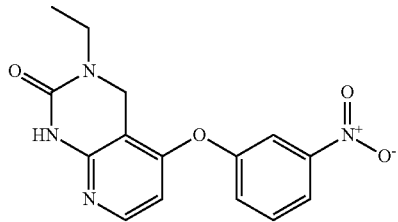 [SMILES: CCN1Cc2c(Oc3cccc([N+](=O)[O-])c3)ccnc2NC1=O]

3-Ethyl-5-(3-nitro-phenoxy)-3,4-dihydro-1H-pyrido[2,3-d]pyrimidin-2-one (150)

The title compound was synthesized according to the procedure described for the preparation of Example 57 using 33 and 3-nitrophenol. LC-MS (M+1=315, obsd.=315).

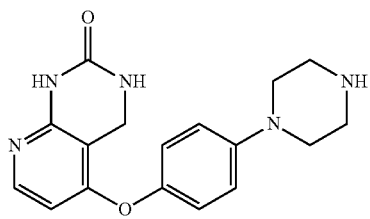 [SMILES: O=C1NCc2c(Oc3ccc(N4CCNCC4)cc3)ccnc2N1]

5-(4-Piperazin-1-yl-phenoxy)-3,4-dihydro-1H-pyrido[2,3-d]pyrimidin-2-one (151)

The title compound was synthesized according to the procedure described for the preparation of Example 57 using 1 and 4-piperazin-1-yl-phenol, followed by removing 3-(4-methoxybenzyl) group with the procedure described for the preparation of Example 3. LC-MS (M+1=326, obsd.=326).

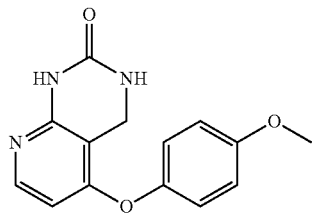 [SMILES: COc1ccc(Oc2ccnc3c2CNC(=O)N3)cc1]

5-(4-Methoxy-phenoxy)-3,4-dihydro-1H-pyrido[2,3-d]pyrimidin-2-one (152)

The title compound was synthesized according to the procedure described for the preparation of Example 57 using 1 and 4-methoxyphenol, followed by removing 3-(4-methoxybenzyl) group with the procedure described for the preparation of Example 3. LC-MS (M+1=272, obsd.=272).

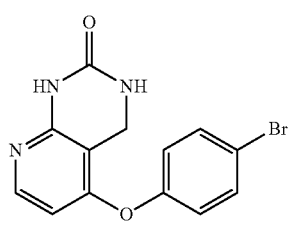

5-(4-Bromo-phenoxy)-3,4-dihydro-1H-pyrido[2,3-d]pyrimidin-2-one (153)

The title compound was synthesized according to the procedure described for the preparation of Example 57 using 1 and 4-bromophenol, followed by removing 3-(4-methoxybenzyl) group with the procedure described for the preparation of Example 3. LC-MS (M+1=320, obsd.=320).

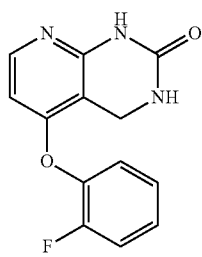 [SMILES: O=C1NCc2c(Oc3ccccc3F)ccnc2N1]

5-(2-Fluoro-phenoxy)-3,4-dihydro-1H-pyrido[2,3-d]pyrimidin-2-one (154)

The title compound was synthesized according to the procedure described for the preparation of Example 57 using 1 and 2-fluorophenol, followed by removing 3-(4-methoxybenzyl) group with the procedure described for the preparation of Example 3. LC-MS (M+1=260, obsd.=260).

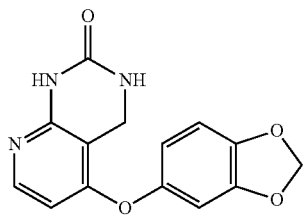 [SMILES: O=C1NCc2c(Oc3ccc4c(c3)OCO4)ccnc2N1]

5-(Benzo[1,3]dioxol-5-yloxy)-3,4-dihydro-1H-pyrido[2,3-d]pyrimidin-2-one (155)

The title compound was synthesized according to the procedure described for the preparation of Example 57 using 1 and benzo[1,3]dioxol-5-ol, followed by removing 3-(4-methoxybenzyl) group with the procedure described for the preparation of Example 3. LC-MS (M+1=287, obsd.=287).

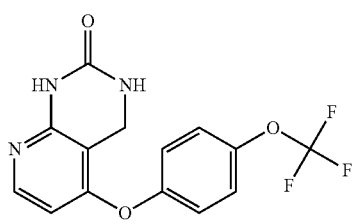 [SMILES: O=C1NCc2c(Oc3ccc(OC(F)(F)F)cc3)ccnc2N1]

5-(4-Trifluoromethoxy-phenoxy)-3,4-dihydro-1H-pyrido[2,3-d]pyrimidin-2-one (156)

The title compound was synthesized according to the procedure described for the preparation of Example 57 using 1 and 4-trifluoromethoxyphenol, followed by removing 3-(4-methoxybenzyl) group with the procedure described for the preparation of Example 3. LC-MS (M+1=326, obsd.=326).

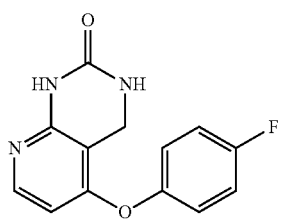 [SMILES: O=C1NCc2c(Oc3ccc(F)cc3)ccnc2N1]

5-(4-Fluoro-phenoxy)-3,4-dihydro-1H-pyrido[2,3-d]pyrimidin-2-one (157)

The title compound was synthesized according to the procedure described for the preparation of Example 57 using 1 and 4-fluorophenol, followed by removing 3-(4-methoxybenzyl) group with the procedure described for the preparation of Example 3. LC-MS (M+1=260, obsd.=260).

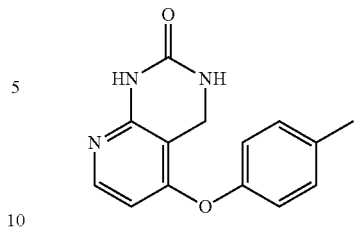

5-p-Tolyloxy-3,4-dihydro-1H-pyrido[2,3-d]pyrimidin-2-one (158)

The title compound was synthesized according to the procedure described for the preparation of Example 57 using 1 and 4-methylphenol, followed by removing 3-(4-methoxybenzyl) group with the procedure described for the preparation of Example 3. LC-MS (M+1=256, obsd.=256).

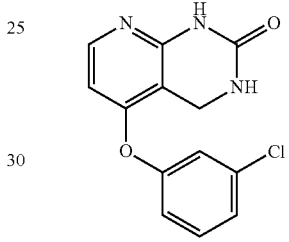

5-(3-Chloro-phenoxy)-3,4-dihydro-1H-pyrido[2,3-d]pyrimidin-2-one (159)

The title compound was synthesized according to the procedure described for the preparation of Example 57 using 1 and 4-chlorophenol, followed by removing 3-(4-methoxybenzyl) group with the procedure described for the preparation of Example 3. LC-MS (M+1=276, obsd.=276).

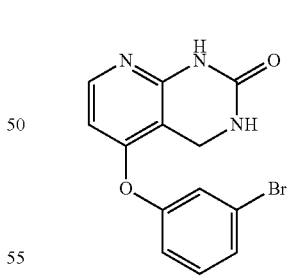

5-(3-Bromo-phenoxy)-3,4-dihydro-1H-pyrido[2,3-d]pyrimidin-2-one (160)

The title compound was synthesized according to the procedure described for the preparation of Example 57 using 1 and 3-bromophenol, followed by removing 3-(4-methoxybenzyl) group with the procedure described for the preparation of Example 3. LC-MS (M+1=320, obsd.=320).

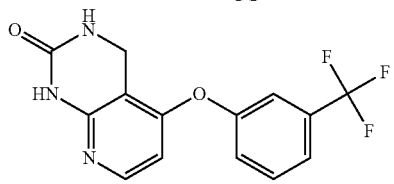

5-(3-Trifluoromethyl-phenoxy)-3,4-dihydro-1H-pyrido[2,3-d]pyrimidin-2-one (161)

The title compound was synthesized according to the procedure described for the preparation of Example 57 using 1 and 3-trifluoromethylphenol, followed by removing 3-(4-methoxybenzyl) group with the procedure described for the preparation of Example 3. LC-MS (M+1=310, obsd.=310).

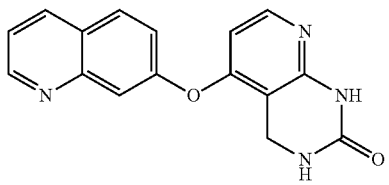 [SMILES: O=C1NCc2c(Oc3ccc4cccnc4c3)ccnc2N1]

5-(Quinolin-7-yloxy)-3,4-dihydro-1H-pyrido[2,3-d]pyrimidin-2-one (162)

The title compound was synthesized according to the procedure described for the preparation of Example 57 using 1 and quinolin-7-ol, followed by removing 3-(4-methoxybenzyl) group with the procedure described for the preparation of Example 3. LC-MS (M+1=293, obsd.=293).

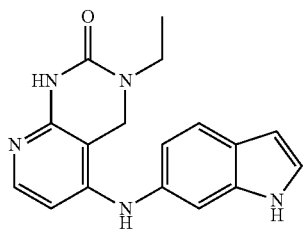 [SMILES: CCN1Cc2c(Nc3ccc4cc[nH]c4c3)ccnc2NC1=O]

3-Ethyl-5-(1H-indol-6-ylamino)-3,4-dihydro-1H-pyrido[2,3-d]pyrimidin-2-one (163)

The title compound was synthesized according to the procedure described for the preparation of Example 34 using 6-aminoindole. LC-MS (M+1=308, obsd.=308).

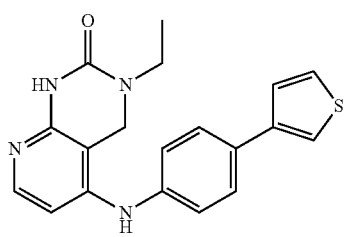 [SMILES: CCN1Cc2c(Nc3ccc(-c4ccsc4)cc3)ccnc2NC1=O]

3-Ethyl-5-(4-thiophen-3-yl-phenylamino)-3,4-dihydro-1H-pyrido[2,3-d]pyrimidin-2-one (164)

The title compound was synthesized according to the procedure described for the preparation of Example 34 using 4-thiophen-3-yl-phenylamine. LC-MS (M+1=351, obsd.=351).

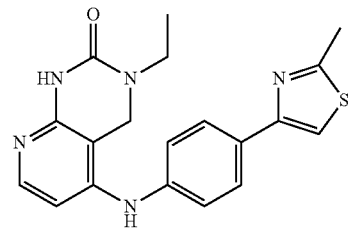 [SMILES: CCN1Cc2c(Nc3ccc(-c4csc(C)n4)cc3)ccnc2NC1=O]

3-Ethyl-5-[4-(2-methyl-thiazol-4-yl)-phenylamino]-3,4-dihydro-1H-pyrido[2,3-d]pyrimidin-2-one (165)

The title compound was synthesized according to the procedure described for the preparation of Example 34 using 4-(2-methyl-thiazol-4-yl)-phenylamine. LC-MS (M+1=366, obsd.=366).

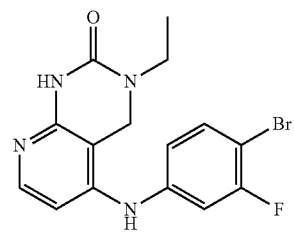 [SMILES: CCN1Cc2c(Nc3ccc(Br)c(F)c3)ccnc2NC1=O]

5-(4-Bromo-3-fluoro-phenylamino)-3-ethyl-3,4-dihydro-1H-pyrido[2,3-d]pyrimidin-2-one (166)

The title compound was synthesized according to the procedure described for the preparation of Example 34 using 4-bromo-3-fluoro-phenylamine. LC-MS (M+1=365, obsd.=365).

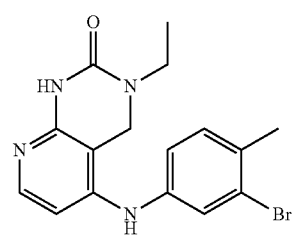 [SMILES: CCN1Cc2c(Nc3ccc(C)c(Br)c3)ccnc2NC1=O]

5-(3-Bromo-4-methyl-phenylamino)-3-ethyl-3,4-dihydro-1H-pyrido[2,3-d]pyrimidin-2-one (167)

The title compound was synthesized according to the procedure described for the preparation of Example 34 using 3-bromo-4-methyl-phenylamine. LC-MS (M+1=361, obsd.=361).

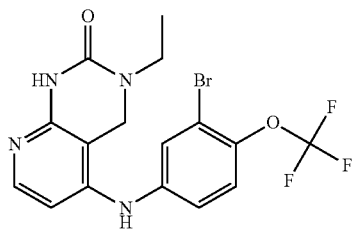 [SMILES: CCN1Cc2c(Nc3ccc(OC(F)(F)F)c(Br)c3)ccnc2NC1=O]

5-(3-Bromo-4-trifluoromethoxy-phenylamino)-3-ethyl-3,4-dihydro-1H-pyrido[2,3-d]pyrimidin-2-one (168)

The title compound was synthesized according to the procedure described for the preparation of Example 34 using 3-bromo-4-trifluoromethoxy-phenylamine. LC-MS (M+1=431, obsd.=431).

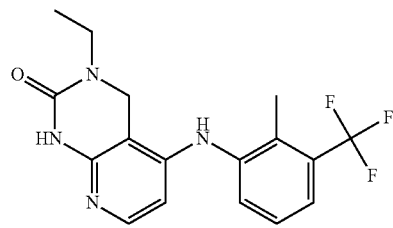

3-Ethyl-5-(2-methyl-3-trifluoromethyl-phenylamino)-3,4-dihydro-1H-pyrido[2,3-d]pyrimidin-2-one (171)

The title compound was synthesized according to the procedure described for the preparation of Example 34 using 2-methyl-3-trifluoromethyl-phenylamine. LC-MS (M+1=351, obsd.=351).

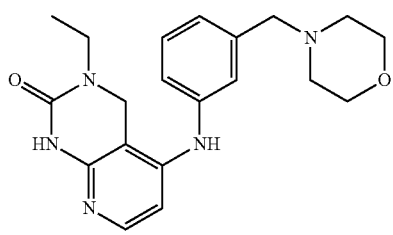 [SMILES: CCN1Cc2c(Nc3cccc(CN4CCOCC4)c3)ccnc2NC1=O]

3-Ethyl-5-(3-morpholin-4-ylmethyl-phenylamino)-3,4-dihydro-1H-pyrido[2,3-d]pyrimidin-2-one (169)

The title compound was synthesized according to the procedure described for the preparation of Example 34 using 3-morpholin-4-ylmethyl-phenylamine. LC-MS (M+1=368, obsd.=368).

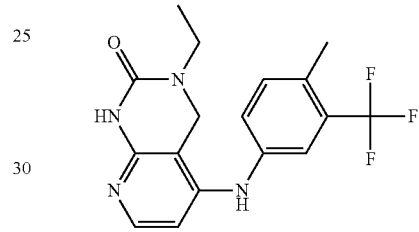

3-Ethyl-5-(4-methyl-3-trifluoromethyl-phenylamino)-3,4-dihydro-1H-pyrido[2,3-d]pyrimidin-2-one (172)

The title compound was synthesized according to the procedure described for the preparation of Example 34 using 4-methyl-3-trifluoromethyl-phenylamine. LC-MS (M+1=351, obsd.=351).

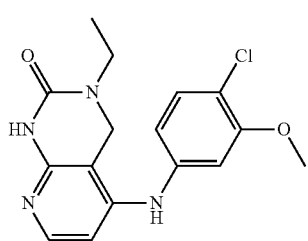 [SMILES: CCN1Cc2c(Nc3ccc(Cl)c(OC)c3)ccnc2NC1=O]

5-(4-Chloro-3-methoxy-phenylamino)-3-ethyl-3,4-dihydro-1H-pyrido[2,3-d]pyrimidin-2-one (170)

The title compound was synthesized according to the procedure described for the preparation of Example 34 using 4-chloro-3-methoxy-phenylamine. LC-MS (M+1=333, obsd.=333).

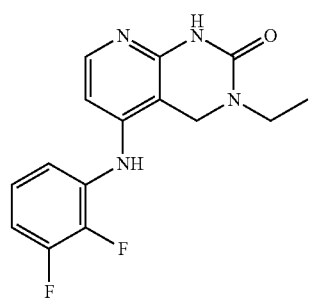 [SMILES: CCN1Cc2c(Nc3cccc(F)c3F)ccnc2NC1=O]

5-(2,3-Difluoro-phenylamino)-3-ethyl-3,4-dihydro-1H-pyrido[2,3-d]pyrimidin-2-one (173)

The title compound was synthesized according to the procedure described for the preparation of Example 34 using 2,3-difluoro-phenylamine. LC-MS (M+1=305, obsd.=305).

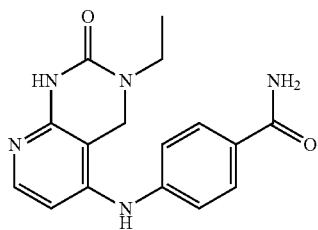 [SMILES: CCN1Cc2c(Nc3ccc(C(N)=O)cc3)ccnc2NC1=O]

4-(3-Ethyl-2-oxo-1,2,3,4-tetrahydro-pyrido[2,3-d]
pyrimidin-5-ylamino)-benzamide (174)

The title compound was synthesized according to the procedure described for the preparation of Example 34 using 4-amino-benzamide. LC-MS (M+1=312, obsd.=312).

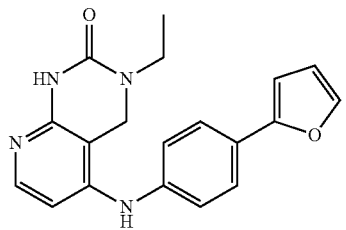

3-Ethyl-5-(4-furan-2-yl-phenylamino)-3,4-dihydro-
1H-pyrido[2,3-d]pyrimidin-2-one (177)

The title compound was synthesized according to the procedure described for the preparation of Example 34 using 4-furan-2-yl-phenylamine. LC-MS (M+1=335, obsd.=335).

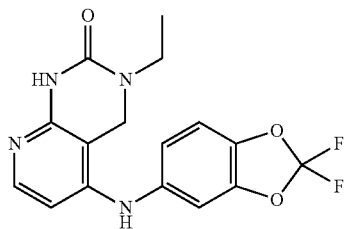 [SMILES: CCN1Cc2c(Nc3ccc4c(c3)OC(F)(F)O4)ccnc2NC1=O]

5-(2,2-Difluoro-benzo[1,3]dioxol-5-ylamino)-3-
ethyl-3,4-dihydro-1H-pyrido[2,3-d]pyrimidin-2-one
(175)

The title compound was synthesized according to the procedure described for the preparation of Example 34 using 2,2-difluoro-benzo[1,3]dioxol-5-ylamine. LC-MS (M+1=349, obsd.=349).

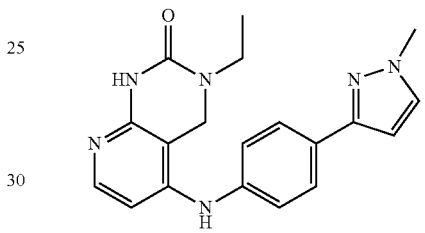

3-Ethyl-5-[4-(1-methyl-1H-pyrazol-3-yl)-phenylamino]-3,4-dihydro-1H-pyrido[2,3-d]pyrimidin-2-
one (178)

The title compound was synthesized according to the procedure described for the preparation of Example 34 using 4-(1-methyl-1H-pyrazol-3-yl)-phenylamine. LC-MS (M+1=349, obsd.=349).

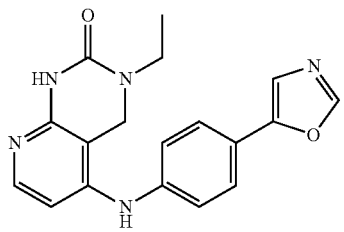 [SMILES: CCN1Cc2c(Nc3ccc(-c4cnco4)cc3)ccnc2NC1=O]

3-Ethyl-5-(4-oxazol-5-yl-phenylamino)-3,4-dihydro-
1H-pyrido[2,3-d]pyrimidin-2-one (176)

The title compound was synthesized according to the procedure described for the preparation of Example 34 using 4-oxazol-5-yl-phenylamine. LC-MS (M+1=336, obsd.=336).

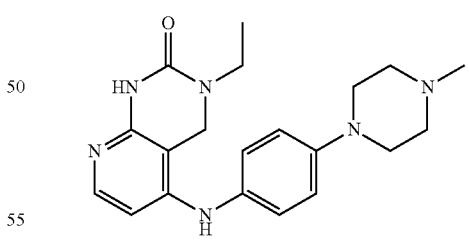

3-Ethyl-5-[4-(4-methyl-piperazin-1-yl)-phenylamino]-3,4-dihydro-1H-pyrido[2,3-d]pyrimidin-2-
one (179)

The title compound was synthesized according to the procedure described for the preparation of Example 34 using 4-(4-methyl-piperazin-1-yl)-phenylamine. LC-MS (M+1=367, obsd.=367).

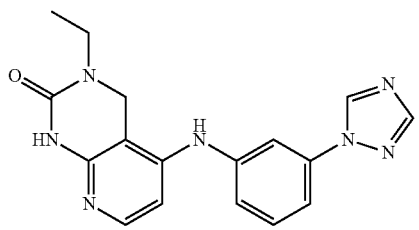 [SMILES: CCN1Cc2c(Nc3cccc(-n4cncn4)c3)ccnc2NC1=O]

3-Ethyl-5-(3-[1,2,4]triazol-1-yl-phenylamino)-3,4-dihydro-1H-pyrido[2,3-d]pyrimidin-2-one (180)

The title compound was synthesized according to the procedure described for the preparation of Example 34 using 3-[1,2,4]triazol-1-yl-phenylamine. LC-MS (M+1=336, obsd.=336).

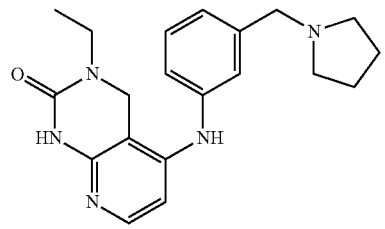

3-Ethyl-5-(3-pyrrolidin-1-ylmethyl-phenylamino)-3,4-dihydro-1H-pyrido[2,3-d]pyrimidin-2-one (183)

The title compound was synthesized according to the procedure described for the preparation of Example 34 using 3-pyrrolidin-1-ylmethyl-phenylamine. LC-MS (M+1=352, obsd.=352).

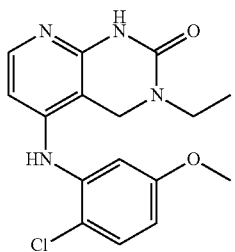 [SMILES: CCN1Cc2c(Nc3cc(OC)ccc3Cl)ccnc2NC1=O]

5-(2-Chloro-5-methoxy-phenylamino)-3-ethyl-3,4-dihydro-1H-pyrido[2,3-d]pyrimidin-2-one (181)

The title compound was synthesized according to the procedure described for the preparation of Example 34 using 2-Chloro-5-methoxy-phenylamine. LC-MS (M+1=333, obsd.=333).

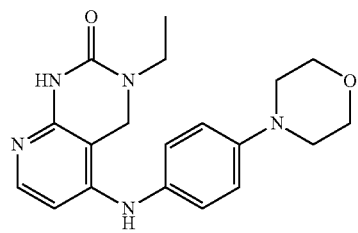

3-Ethyl-5-(4-morpholin-4-yl-phenylamino)-3,4-dihydro-1H-pyrido[2,3-d]pyrimidin-2-one (184)

The title compound was synthesized according to the procedure described for the preparation of Example 34 using 4-morpholin-4-yl-phenylamine. LC-MS (M+1=354, obsd.=354).

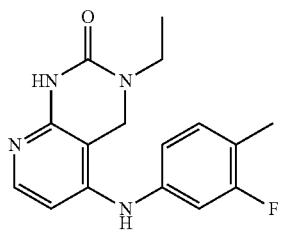 [SMILES: CCN1Cc2c(Nc3ccc(C)c(F)c3)ccnc2NC1=O]

3-Ethyl-5-(3-fluoro-4-methyl-phenylamino)-3,4-dihydro-1H-pyrido[2,3-d]pyrimidin-2-one (182)

The title compound was synthesized according to the procedure described for the preparation of Example 34 using 3-fluoro-4-methyl-phenylamine. LC-MS (M+1=301, obsd.=301).

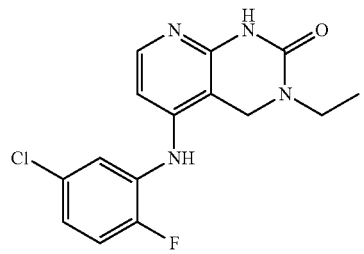 [SMILES: CCN1Cc2c(Nc3cc(Cl)ccc3F)ccnc2NC1=O]

5-(5-Chloro-2-fluoro-phenylamino)-3-ethyl-3,4-dihydro-1H-pyrido[2,3-d]pyrimidin-2-one (185)

The title compound was synthesized according to the procedure described for the preparation of Example 34 using 5-chloro-2-fluoro-phenylamine. LC-MS (M+1=321, obsd.=321).

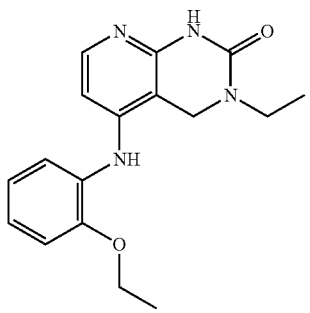 [SMILES: CCOc1ccccc1Nc1ccnc2c1CN(CC)C(=O)N2]

5-(2-Ethoxy-phenylamino)-3-ethyl-3,4-dihydro-1H-pyrido[2,3-d]pyrimidin-2-one (186)

The title compound was synthesized according to the procedure described for the preparation of Example 34 using 2-ethoxy-phenylamine. LC-MS (M+1=313, obsd.=313).

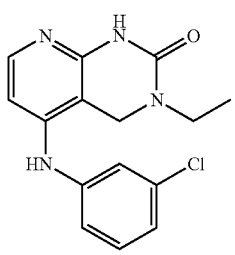 [SMILES: CCN1Cc2c(Nc3cccc(Cl)c3)ccnc2NC1=O]

5-(3-Chloro-phenylamino)-3-ethyl-3,4-dihydro-1H-pyrido[2,3-d]pyrimidin-2-one (187)

The title compound was synthesized according to the procedure described for the preparation of Example 34 using 3-chloro-phenylamine. LC-MS (M+1=303, obsd.=303).

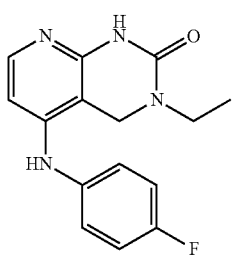 [SMILES: CCN1Cc2c(Nc3ccc(F)cc3)ccnc2NC1=O]

3-Ethyl-5-(4-fluoro-phenylamino)-3,4-dihydro-1H-pyrido[2,3-d]pyrimidin-2-one (188)

The title compound was synthesized according to the procedure described for the preparation of Example 34 using 4-fluoro-phenylamine. LC-MS (M+1=287, obsd.=287).

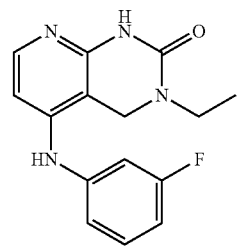 [SMILES: CCN1Cc2c(Nc3cccc(F)c3)ccnc2NC1=O]

3-Ethyl-5-(3-fluoro-phenylamino)-3,4-dihydro-1H-pyrido[2,3-d]pyrimidin-2-one (189)

The title compound was synthesized according to the procedure described for the preparation of Example 34 using 3-fluoro-phenylamine. LC-MS (M+1=287, obsd.=287).

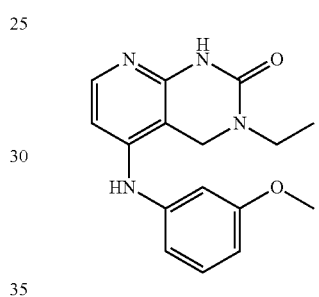

3-Ethyl-5-(3-methoxy-phenylamino)-3,4-dihydro-1H-pyrido[2,3-d]pyrimidin-2-one (190)

The title compound was synthesized according to the procedure described for the preparation of Example 34 using 3-methoxy-phenylamine. LC-MS (M+1=299, obsd.=299).

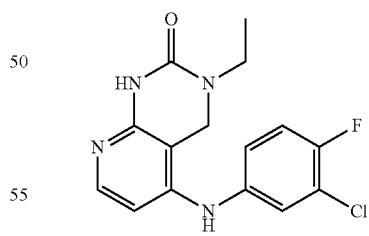

5-(3-Chloro-4-fluoro-phenylamino)-3-ethyl-3,4-dihydro-1H-pyrido[2,3-d]pyrimidin-2-one (191)

The title compound was synthesized according to the procedure described for the preparation of Example 34 using 3-chloro-4-fluoro-phenylamine. LC-MS (M+1=321, obsd.=321).

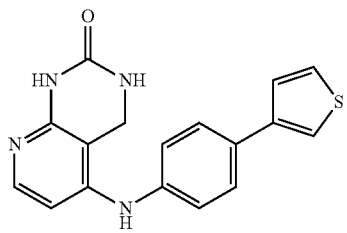 [SMILES: O=C1NCc2c(Nc3ccc(-c4ccsc4)cc3)ccnc2N1]

5-(4-Thiophen-3-yl-phenylamino)-3,4-dihydro-1H-pyrido[2,3-d]pyrimidin-2-one (192)

The title compound was synthesized according to the procedure described for the preparation of Example 100 using 4-thiophen-3-yl-phenylamine, followed by removing 3-(4-methoxybenzyl) group with the procedure described for the preparation of Example 3. LC-MS (M+1=323, obsd.=323).

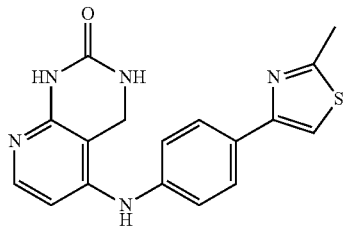 [SMILES: Cc1nc(-c2ccc(Nc3ccnc4c3CNC(=O)N4)cc2)cs1]

5-[4-(2-Methyl-thiazol-4-yl)-phenylamino]-3,4-dihydro-1H-pyrido[2,3-d]pyrimidin-2-one (193)

The title compound was synthesized according to the procedure described for the preparation of Example 100 using 4-(2-methyl-thiazol-4-yl)-phenylamine, followed by removing 3-(4-methoxybenzyl) group with the procedure described for the preparation of Example 3. LC-MS (M+1=338, obsd.=338).

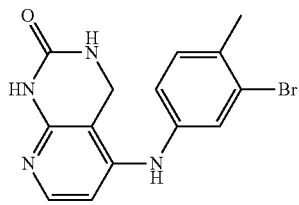 [SMILES: Cc1ccc(Nc2ccnc3c2CNC(=O)N3)cc1Br]

RON $IC_{50}$="+"

5-(3-Bromo-4-methyl-phenylamino)-3,4-dihydro-1H-pyrido[2,3-d]pyrimidin-2-one (194)

The title compound was synthesized according to the procedure described for the preparation of Example 100 using 3-bromo-4-methyl-phenylamine, followed by removing 3-(4-methoxybenzyl) group with the procedure described for the preparation of Example 3. LC-MS (M+1=333, obsd.=333).

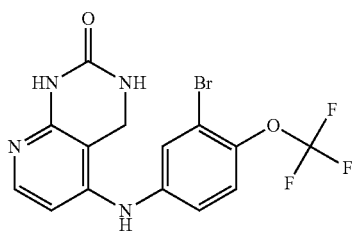 [SMILES: O=C1NCc2c(Nc3ccc(OC(F)(F)F)c(Br)c3)ccnc2N1]

RON $IC_{50}$="+"

5-(3-Bromo-4-trifluoromethoxy-phenylamino)-3,4-dihydro-1H-pyrido[2,3-d]pyrimidin-2-one (195)

The title compound was synthesized according to the procedure described for the preparation of Example 100 using 3-bromo-4-trifluoromethoxy-phenylamine, followed by removing 3-(4-methoxybenzyl) group with the procedure described for the preparation of Example 3. LC-MS (M+1=403, obsd.=403).

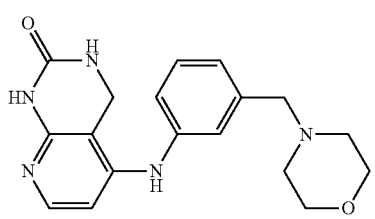 [SMILES: O=C1NCc2c(Nc3cccc(CN4CCOCC4)c3)ccnc2N1]

5-(3-Morpholin-4-ylmethyl-phenylamino)-3,4-dihydro-1H-pyrido[2,3-d]pyrimidin-2-one (196)

The title compound was synthesized according to the procedure described for the preparation of Example 100 using 3-morpholin-4-ylmethyl-phenylamine, followed by removing 3-(4-methoxybenzyl) group with the procedure described for the preparation of Example 3. LC-MS (M+1=340, obsd.=340).

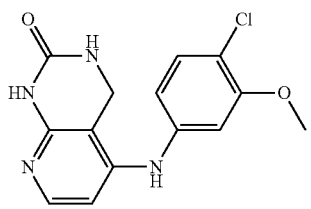 [SMILES: COc1cc(Nc2ccnc3c2CNC(=O)N3)ccc1Cl]

5-(4-Chloro-3-methoxy-phenylamino)-3,4-dihydro-1H-pyrido[2,3-d]pyrimidin-2-one (197)

The title compound was synthesized according to the procedure described for the preparation of Example 100 using 4-chloro-3-methoxy-phenylamine, followed by removing 3-(4-methoxybenzyl) group with the procedure described for the preparation of Example 3. LC-MS (M+1=305, obsd.=305).

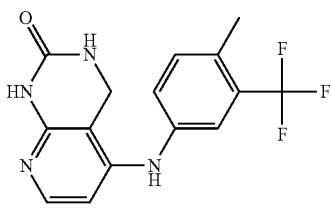 [SMILES: Cc1ccc(Nc2ccnc3c2CNC(=O)N3)cc1C(F)(F)F]

5-(4-Methyl-3-trifluoromethyl-phenylamino)-3,4-dihydro-1H-pyrido[2,3-d]pyrimidin-2-one (198)

The title compound was synthesized according to the procedure described for the preparation of Example 100 using 4-methyl-3-trifluoromethyl-phenylamine, followed by removing 3-(4-methoxybenzyl) group with the procedure described for the preparation of Example 3. LC-MS (M+1=323, obsd.=323).

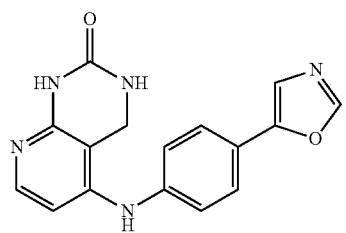 [SMILES: O=C1NCc2c(Nc3ccc(-c4cnco4)cc3)ccnc2N1]

5-(4-Oxazol-5-yl-phenylamino)-3,4-dihydro-1H-pyrido[2,3-d]pyrimidin-2-one (199)

The title compound was synthesized according to the procedure described for the preparation of Example 100 using 4-oxazol-5-yl-phenylamine, followed by removing 3-(4-methoxybenzyl) group with the procedure described for the preparation of Example 3. LC-MS (M+1=308, obsd.=308).

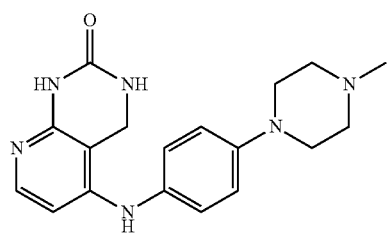 [SMILES: CN1CCN(c2ccc(Nc3ccnc4c3CNC(=O)N4)cc2)CC1]

5-[4-(4-Methyl-piperazin-1-yl)-phenylamino]-3,4-dihydro-1H-pyrido[2,3-d]pyrimidin-2-one (200)

The title compound was synthesized according to the procedure described for the preparation of Example 100 using 4-(4-methyl-piperazin-1-yl)-phenylamine, followed by removing 3-(4-methoxybenzyl) group with the procedure described for the preparation of Example 3. LC-MS (M+1=339, obsd.=339).

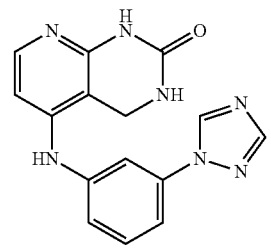 [SMILES: O=C1NCc2c(Nc3cccc(-n4cncn4)c3)ccnc2N1]

5-(3-[1,2,4]Triazol-1-yl-phenylamino)-3,4-dihydro-1H-pyrido[2,3-d]pyrimidin-2-one (201)

The title compound was synthesized according to the procedure described for the preparation of Example 100 using 3-[1,2,4]triazol-1-yl-phenylamine, followed by removing 3-(4-methoxybenzyl) group with the procedure described for the preparation of Example 3. LC-MS (M+1=308, obsd.=308).

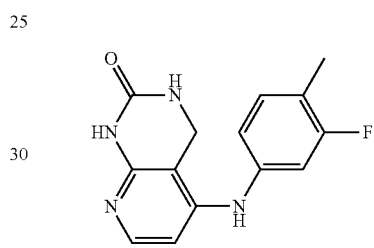

5-(3-Fluoro-4-methyl-phenylamino)-3,4-dihydro-1H-pyrido[2,3-d]pyrimidin-2-one (202)

The title compound was synthesized according to the procedure described for the preparation of Example 100 using 3-fluoro-4-methyl-phenylamine, followed by removing 3-(4-methoxybenzyl) group with the procedure described for the preparation of Example 3. LC-MS (M+1=273, obsd.=273).

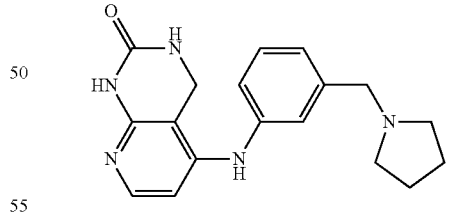

5-(3-Pyrrolidin-1-ylmethyl-phenylamino)-3,4-dihydro-1H-pyrido[2,3-d]pyrimidin-2-one (203)

The title compound was synthesized according to the procedure described for the preparation of Example 100 using 3-pyrrolidin-1-ylmethyl-phenylamine, followed by removing 3-(4-methoxybenzyl) group with the procedure described for the preparation of Example 3. LC-MS (M+1=324, obsd.=324).

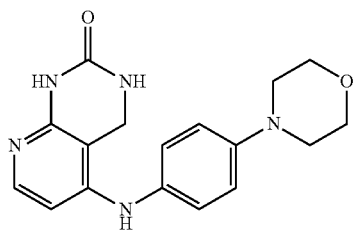 [SMILES: O=C1NCc2c(Nc3ccc(N4CCOCC4)cc3)ccnc2N1]

5-(4-Morpholin-4-yl-phenylamino)-3,4-dihydro-1H-pyrido[2,3-d]pyrimidin-2-one (204)

The title compound was synthesized according to the procedure described for the preparation of Example 100 using 4-morpholin-4-yl-phenylamine, followed by removing 3-(4-methoxybenzyl) group with the procedure described for the preparation of Example 3. LC-MS (M+1=326, obsd.=326).

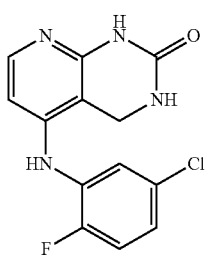 [SMILES: O=C1NCc2c(Nc3cc(Cl)ccc3F)ccnc2N1]

5-(5-Chloro-2-fluoro-phenylamino)-3,4-dihydro-1H-pyrido[2,3-d]pyrimidin-2-one (205)

The title compound was synthesized according to the procedure described for the preparation of Example 100 using 5-chloro-2-fluoro-phenylamine, followed by removing 3-(4-methoxybenzyl) group with the procedure described for the preparation of Example 3. LC-MS (M+1=298, obsd.=298).

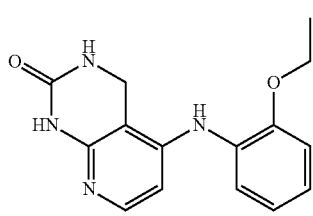 [SMILES: CCOc1ccccc1Nc1ccnc2c1CNC(=O)N2]

5-(2-Ethoxy-phenylamino)-3,4-dihydro-1H-pyrido[2,3-d]pyrimidin-2-one (206)

The title compound was synthesized according to the procedure described for the preparation of Example 100 using 2-ethoxy-phenylamine, followed by removing 3-(4-methoxybenzyl) group with the procedure described for the preparation of Example 3. LC-MS (M+1=285, obsd.=285).

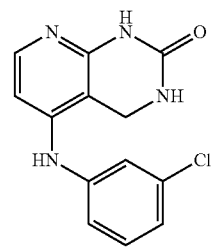 [SMILES: O=C1NCc2c(Nc3cccc(Cl)c3)ccnc2N1]

5-(3-Chloro-phenylamino)-3,4-dihydro-1H-pyrido[2,3-d]pyrimidin-2-one (207)

The title compound was synthesized according to the procedure described for the preparation of Example 100 using 3-chloro-phenylamine, followed by removing 3-(4-methoxybenzyl) group with the procedure described for the preparation of Example 3. LC-MS (M+1=275, obsd.=275).

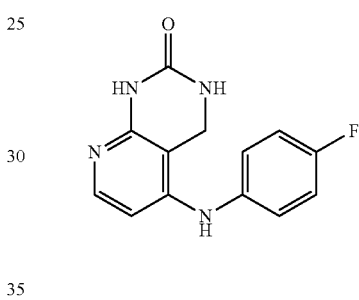

5-(4-Fluoro-phenylamino)-3,4-dihydro-1H-pyrido[2,3-d]pyrimidin-2-one (208)

The title compound was synthesized according to the procedure described for the preparation of Example 100 using 4-fluoro-phenylamine, followed by removing 3-(4-methoxybenzyl) group with the procedure described for the preparation of Example 3. LC-MS (M+1=259, obsd.=259).

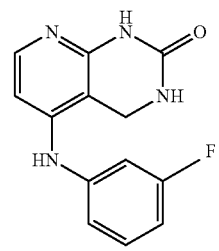

5-(3-Fluoro-phenylamino)-3,4-dihydro-1H-pyrido[2,3-d]pyrimidin-2-one (209)

The title compound was synthesized according to the procedure described for the preparation of Example 100 using 3-fluoro-phenylamine, followed by removing 3-(4-methoxybenzyl) group with the procedure described for the preparation of Example 3. LC-MS (M+1=259, obsd.=259).

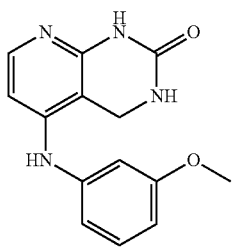 [SMILES: COc1cccc(Nc2ccnc3c2CNC(=O)N3)c1]

5-(3-Methoxy-phenylamino)-3,4-dihydro-1H-pyrido
[2,3-d]pyrimidin-2-one (210)

The title compound was synthesized according to the procedure described for the preparation of Example 100 using 3-methoxy-phenylamine, followed by removing 3-(4-methoxybenzyl) group with the procedure described for the preparation of Example 3. LC-MS (M+1=271, obsd.=271).

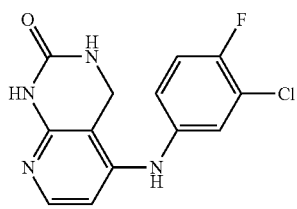 [SMILES: O=C1NCc2c(Nc3ccc(F)c(Cl)c3)ccnc2N1]

5-(3-Chloro-4-fluoro-phenylamino)-3,4-dihydro-1H-pyrido[2,3-d]pyrimidin-2-one (211)

The title compound was synthesized according to the procedure described for the preparation of Example 100 using 3-chloro-4-fluoro-phenylamine, followed by removing 3-(4-methoxybenzyl) group with the procedure described for the preparation of Example 3. LC-MS (M+1=293, obsd.=293).

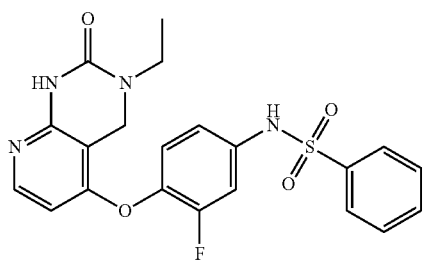 [SMILES: CCN1Cc2c(Oc3ccc(NS(=O)(=O)c4ccccc4)cc3F)ccnc2NC1=O]

N-[4-(3-Ethyl-2-oxo-1,2,3,4-tetrahydro-pyrido[2,3-d]pyrimidin-5-yloxy)-3-fluoro-phenyl]-benzenesulfonamide (212)

The title compound was synthesized according to the procedure described for the preparation of Example 62 using 82 and benzenesulfonyl chloride. LC-MS (M+1=443, obsd.=443).

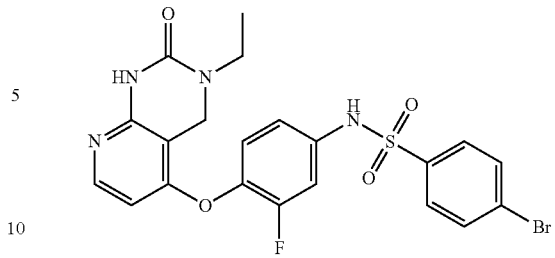

4-Bromo-N-[4-(3-ethyl-2-oxo-1,2,3,4-tetrahydro-pyrido[2,3-d]pyrimidin-5-yloxy)-3-fluoro-phenyl]-benzenesulfonamide (213)

The title compound was synthesized according to the procedure described for the preparation of Example 62 using 82 and 4-bromobenzenesulfonyl chloride. LC-MS (M+1=521, obsd.=521).

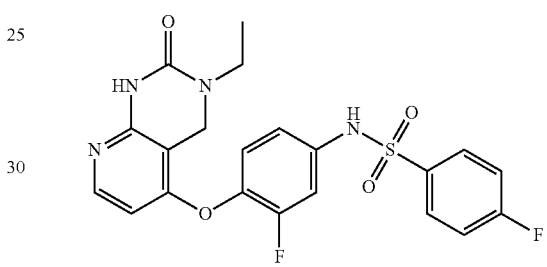

N-[4-(3-Ethyl-2-oxo-1,2,3,4-tetrahydro-pyrido[2,3-d]pyrimidin-5-yloxy)-3-fluoro-phenyl]-4-fluoro-benzenesulfonamide (214)

The title compound was synthesized according to the procedure described for the preparation of Example 62 using 82 and 4-fluorobenzenesulfonyl chloride. LC-MS (M+1=461, obsd.=461).

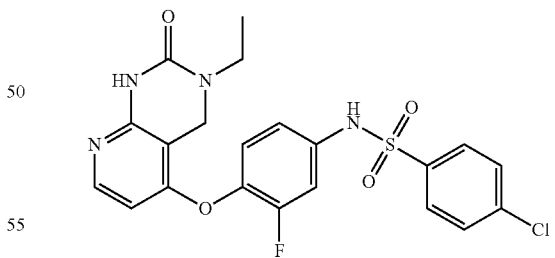

4-Chloro-N-[4-(3-ethyl-2-oxo-1,2,3,4-tetrahydro-pyrido[2,3-d]pyrimidin-5-yloxy)-3-fluoro-phenyl]-benzenesulfonamide (215)

The title compound was synthesized according to the procedure described for the preparation of Example 62 using 82 and 4-chlorobenzenesulfonyl chloride. LC-MS (M+1=477, obsd.=477).

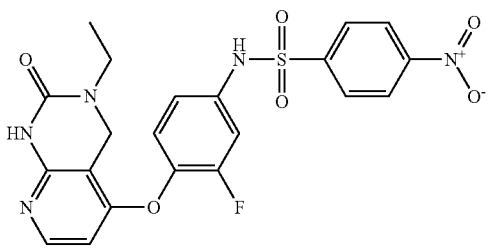 [SMILES: CCN1Cc2c(Oc3ccc(NS(=O)(=O)c4ccc([N+](=O)[O-])cc4)cc3F)ccnc2NC1=O]

N-[4-(3-Ethyl-2-oxo-1,2,3,4-tetrahydro-pyrido[2,3-d]pyrimidin-5-yloxy)-3-fluoro-phenyl]-4-nitro-benzenesulfonamide (216)

The title compound was synthesized according to the procedure described for the preparation of Example 62 using 82 and 4-nitrobenzenesulfonyl chloride. LC-MS (M+1=488, obsd.=488).

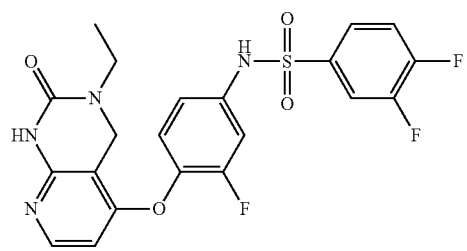

N-[4-(3-Ethyl-2-oxo-1,2,3,4-tetrahydro-pyrido[2,3-d]pyrimidin-5-yloxy)-3-fluoro-phenyl]-3,4-difluoro-benzenesulfonamide (219)

The title compound was synthesized according to the procedure described for the preparation of Example 62 using 82 and 3,4-difluorobenzenesulfonyl chloride. LC-MS (M+1=479, obsd.=479).

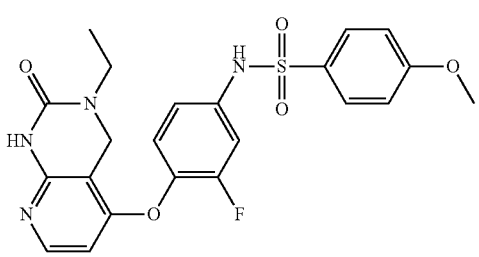 [SMILES: CCN1Cc2c(Oc3ccc(NS(=O)(=O)c4ccc(OC)cc4)cc3F)ccnc2NC1=O]

N-[4-(3-Ethyl-2-oxo-1,2,3,4-tetrahydro-pyrido[2,3-d]pyrimidin-5-yloxy)-3-fluoro-phenyl]-4-methoxy-benzenesulfonamide (217)

The title compound was synthesized according to the procedure described for the preparation of Example 62 using 82 and 4-methoxybenzenesulfonyl chloride. LC-MS (M+1=473, obsd.=473).

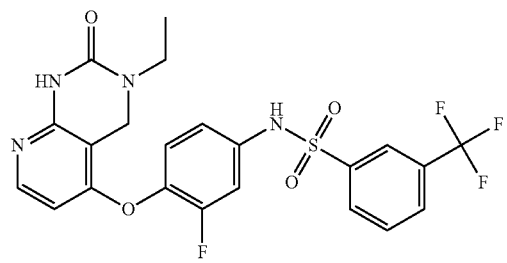

N-[4-(3-Ethyl-2-oxo-1,2,3,4-tetrahydro-pyrido[2,3-d]pyrimidin-5-yloxy)-3-fluoro-phenyl]-3-trifluoromethyl-benzenesulfonamide (220)

The title compound was synthesized according to the procedure described for the preparation of Example 62 using 82 and 3-trifluoromethylbenzenesulfonyl chloride. LC-MS (M+1=511, obsd.=511).

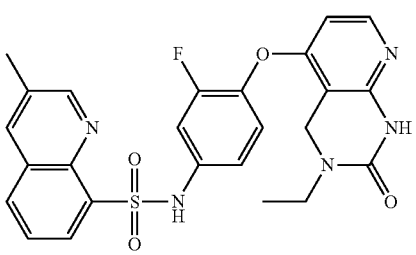 [SMILES: CCN1Cc2c(Oc3ccc(NS(=O)(=O)c4cccc5cc(C)cnc45)cc3F)ccnc2NC1=O]

3-Methyl-quinoline-8-sulfonic acid [4-(3-ethyl-2-oxo-1,2,3,4-tetrahydro-pyrido[2,3-d]pyrimidin-5-yloxy)-3-fluoro-phenyl]-amide (218)

The title compound was synthesized according to the procedure described for the preparation of Example 62 using 82 and 3-methyl-quinoline-8-sulfonyl chloride. LC-MS (M+1=508, obsd.=508).

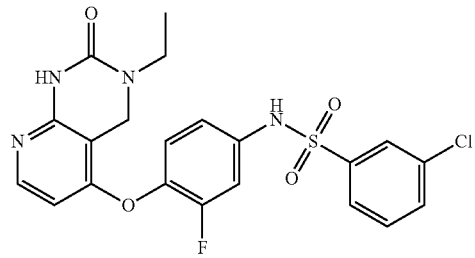 [SMILES: CCN1Cc2c(Oc3ccc(NS(=O)(=O)c4cccc(Cl)c4)cc3F)ccnc2NC1=O]

3-Chloro-N-[4-(3-ethyl-2-oxo-1,2,3,4-tetrahydro-pyrido[2,3-d]pyrimidin-5-yloxy)-3-fluoro-phenyl]-benzenesulfonamide (221)

The title compound was synthesized according to the procedure described for the preparation of Example 62 using 82 and 3-chlorobenzenesulfonyl chloride. LC-MS (M+1=477, obsd.=477).

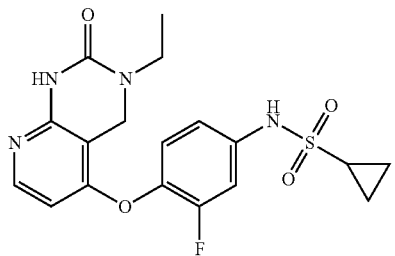 [SMILES: CCN1Cc2c(Oc3ccc(NS(=O)(=O)C4CC4)cc3F)ccnc2NC1=O]

Cyclopropanesulfonic acid [4-(3-ethyl-2-oxo-1,2,3,4-tetrahydro-pyrido[2,3-d]pyrimidin-5-yloxy)-3-fluoro-phenyl]-amide (222)

The title compound was synthesized according to the procedure described for the preparation of Example 62 using 82 and cyclopropanesulfonyl chloride. LC-MS (M+1=407, obsd.=407).

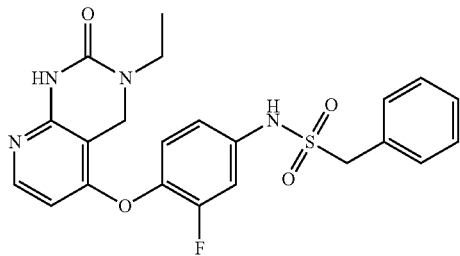 [SMILES: CCN1Cc2c(Oc3ccc(NS(=O)(=O)Cc4ccccc4)cc3F)ccnc2NC1=O]

N-[4-(3-Ethyl-2-oxo-1,2,3,4-tetrahydro-pyrido[2,3-d]pyrimidin-5-yloxy)-3-fluoro-phenyl]-C-phenyl-methanesulfonamide (223)

The title compound was synthesized according to the procedure described for the preparation of Example 62 using 82 and phenyl-methanesulfonyl chloride. LC-MS (M+1=457, obsd.=457).

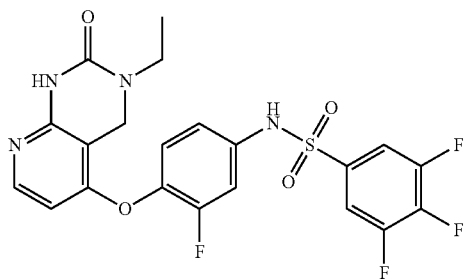 [SMILES: CCN1Cc2c(Oc3ccc(NS(=O)(=O)c4cc(F)c(F)c(F)c4)cc3F)ccnc2NC1=O]

N-[4-(3-Ethyl-2-oxo-1,2,3,4-tetrahydro-pyrido[2,3-d]pyrimidin-5-yloxy)-3-fluoro-phenyl]-3,4,5-trifluoro-benzenesulfonamide (224)

The title compound was synthesized according to the procedure described for the preparation of Example 62 using 82 and 3,4,5-trifluorobenzenesulfonyl chloride. LC-MS (M+1=497, obsd.=497).

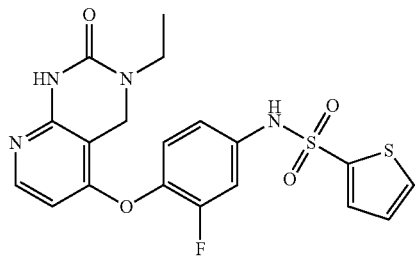 [SMILES: CCN1Cc2c(Oc3ccc(NS(=O)(=O)c4cccs4)cc3F)ccnc2NC1=O]

Thiophene-2-sulfonic acid [4-(3-ethyl-2-oxo-1,2,3,4-tetrahydro-pyrido[2,3-d]pyrimidin-5-yloxy)-3-fluoro-phenyl]-amide (225)

The title compound was synthesized according to the procedure described for the preparation of Example 62 using 82 and thiophene-2-sulfonyl chloride. LC-MS (M+1=449, obsd.=449).

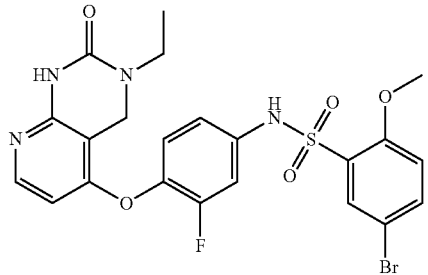 [SMILES: CCN1Cc2c(Oc3ccc(NS(=O)(=O)c4cc(Br)ccc4OC)cc3F)ccnc2NC1=O]

5-Bromo-N-[4-(3-ethyl-2-oxo-1,2,3,4-tetrahydro-pyrido[2,3-d]pyrimidin-5-yloxy)-3-fluoro-phenyl]-2-methoxy-benzenesulfonamide (226)

The title compound was synthesized according to the procedure described for the preparation of Example 62 using 82 and 5-bromo-2-methoxybenzenesulfonyl chloride. LC-MS (M+1=551, obsd.=551).

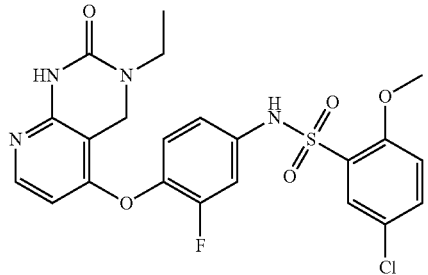 [SMILES: CCN1Cc2c(Oc3ccc(NS(=O)(=O)c4cc(Cl)ccc4OC)cc3F)ccnc2NC1=O]

5-Chloro-N-[4-(3-ethyl-2-oxo-1,2,3,4-tetrahydro-pyrido[2,3-d]pyrimidin-5-yloxy)-3-fluoro-phenyl]-2-methoxy-benzenesulfonamide (227)

The title compound was synthesized according to the procedure described for the preparation of Example 62 using 82 and 5-chloro-2-methoxybenzenesulfonyl chloride. LC-MS (M+1=507, obsd.=507).

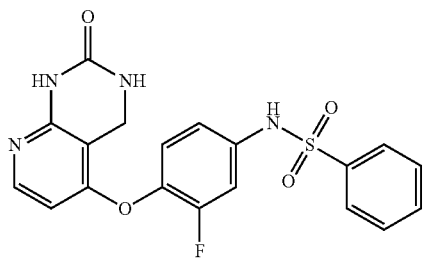 [SMILES: O=C1NCc2c(Oc3ccc(NS(=O)(=O)c4ccccc4)cc3F)ccnc2N1]

N-[3-Fluoro-4-(2-oxo-1,2,3,4-tetrahydro-pyrido[2,3-d]pyrimidin-5-yloxy)-phenyl]-benzenesulfonamide (228)

The title compound was synthesized according to the procedure described for the preparation of Example 62 using benzenesulfonyl chloride, followed by removing 3-(4-methoxybenzyl) group with the procedure described for the preparation of Example 3. LC-MS (M+1=415, obsd.=415).

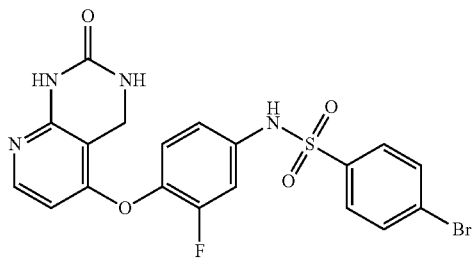 [SMILES: O=C1NCc2c(Oc3ccc(NS(=O)(=O)c4ccc(Br)cc4)cc3F)ccnc2N1]

4-Bromo-N-[3-fluoro-4-(2-oxo-1,2,3,4-tetrahydro-pyrido[2,3-d]pyrimidin-5-yloxy)-phenyl]-benzenesulfonamide (229)

The title compound was synthesized according to the procedure described for the preparation of Example 62 using 4-bromobenzenesulfonyl chloride, followed by removing 3-(4-methoxybenzyl) group with the procedure described for the preparation of Example 3. LC-MS (M+1=493, obsd.=493).

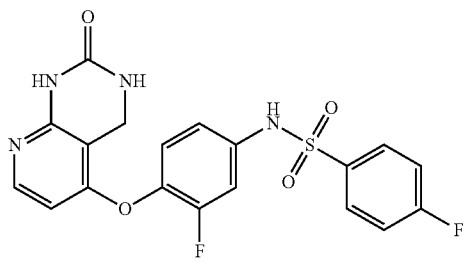 [SMILES: O=C1NCc2c(Oc3ccc(NS(=O)(=O)c4ccc(F)cc4)cc3F)ccnc2N1]

4-Fluoro-N-[3-fluoro-4-(2-oxo-1,2,3,4-tetrahydro-pyrido[2,3-d]pyrimidin-5-yloxy)-phenyl]-benzenesulfonamide (230)

The title compound was synthesized according to the procedure described for the preparation of Example 62 using 4-fluorobenzenesulfonyl chloride, followed by removing 3-(4-methoxybenzyl) group with the procedure described for the preparation of Example 3. LC-MS (M+1=433, obsd.=433).

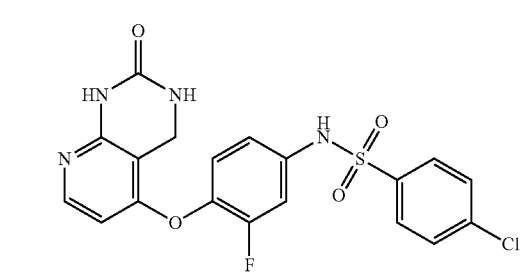 [SMILES: O=C1NCc2c(Oc3ccc(NS(=O)(=O)c4ccc(Cl)cc4)cc3F)ccnc2N1]

4-Chloro-N-[3-fluoro-4-(2-oxo-1,2,3,4-tetrahydro-pyrido[2,3-d]pyrimidin-5-yloxy)-phenyl]-benzenesulfonamide (231)

The title compound was synthesized according to the procedure described for the preparation of Example 62 using 4-chlorobenzenesulfonyl chloride, followed by removing 3-(4-methoxybenzyl) group with the procedure described for the preparation of Example 3. LC-MS (M+1=449, obsd.=449).

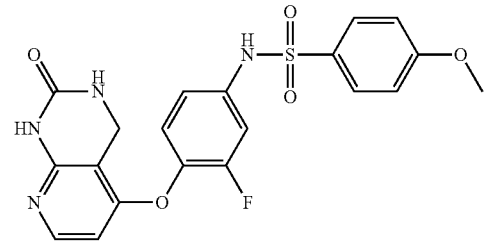 [SMILES: COc1ccc(S(=O)(=O)Nc2ccc(Oc3ccnc4c3CNC(=O)N4)c(F)c2)cc1]

N-[3-Fluoro-4-(2-oxo-1,2,3,4-tetrahydro-pyrido[2,3-d]pyrimidin-5-yloxy)-phenyl]-4-methoxy-benzenesulfonamide (232)

The title compound was synthesized according to the procedure described for the preparation of Example 62 using 4-methoxybenzenesulfonyl chloride, followed by removing 3-(4-methoxybenzyl) group with the procedure described for the preparation of Example 3. LC-MS (M+1=445, obsd.=445).

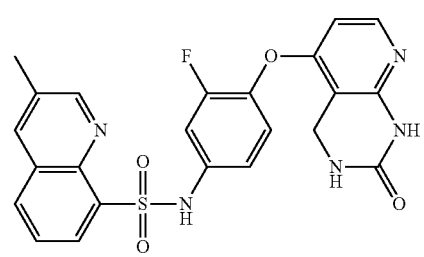 [SMILES: Cc1cnc2c(S(=O)(=O)Nc3ccc(Oc4ccnc5c4CNC(=O)N5)c(F)c3)cccc2c1]

3-Methyl-quinoline-8-sulfonic acid [3-fluoro-4-(2-oxo-1,2,3,4-tetrahydro-pyrido[2,3-d]pyrimidin-5-yloxy)-phenyl]-amide (233)

The title compound was synthesized according to the procedure described for the preparation of Example 62 using 3-methyl-quinoline-8-sulfonyl chloride, followed by removing 3-(4-methoxybenzyl) group with the procedure described for the preparation of Example 3. LC-MS (M+1=480, obsd.=480).

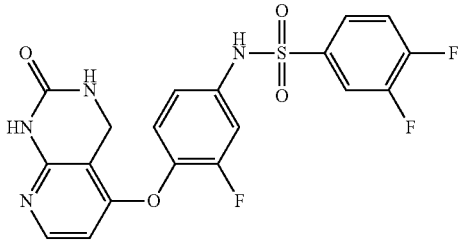 [SMILES: O=C1NCc2c(Oc3ccc(NS(=O)(=O)c4ccc(F)c(F)c4)cc3F)ccnc2N1]

3,4-Difluoro-N-[3-fluoro-4-(2-oxo-1,2,3,4-tetrahydro-pyrido[2,3-d]pyrimidin-5-yloxy)-phenyl]-benzenesulfonamide (234)

The title compound was synthesized according to the procedure described for the preparation of Example 62 using 3,4-difluorobenzenesulfonyl chloride, followed by removing 3-(4-methoxybenzyl) group with the procedure described for the preparation of Example 3. LC-MS (M+1=451, obsd.=451).

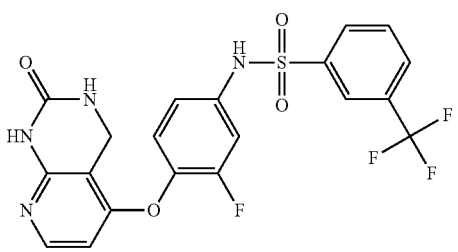 [SMILES: O=C1NCc2c(Oc3ccc(NS(=O)(=O)c4cccc(C(F)(F)F)c4)cc3F)ccnc2N1]

N-[3-Fluoro-4-(2-oxo-1,2,3,4-tetrahydro-pyrido[2,3-d]pyrimidin-5-yloxy)-phenyl]-3-trifluoromethyl-benzenesulfonamide (235)

The title compound was synthesized according to the procedure described for the preparation of Example 62 using 3-trifluoromethyl-benzenesulfonyl chloride, followed by removing 3-(4-methoxybenzyl) group with the procedure described for the preparation of Example 3. LC-MS (M+1=483, obsd.=483).

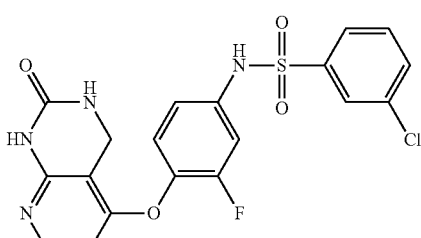

3-Chloro-N-[3-fluoro-4-(2-oxo-1,2,3,4-tetrahydro-pyrido[2,3-d]pyrimidin-5-yloxy)-phenyl]-benzenesulfonamide (236)

The title compound was synthesized according to the procedure described for the preparation of Example 62 using 4-chlorobenzenesulfonyl chloride, followed by removing 3-(4-methoxybenzyl) group with the procedure described for the preparation of Example 3. LC-MS (M+1=449, obsd.=449).

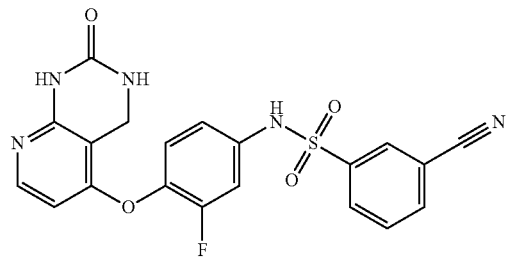 [SMILES: N#Cc1cccc(S(=O)(=O)Nc2ccc(Oc3ccnc4c3CNC(=O)N4)c(F)c2)c1]

3-Cyano-N-[3-fluoro-4-(2-oxo-1,2,3,4-tetrahydro-pyrido[2,3-d]pyrimidin-5-yloxy)-phenyl]-benzenesulfonamide (237)

The title compound was synthesized according to the procedure described for the preparation of Example 62 using 3-cyanobenzenesulfonyl chloride, followed by removing 3-(4-methoxybenzyl) group with the procedure described for the preparation of Example 3. LC-MS (M+1=440, obsd.=440).

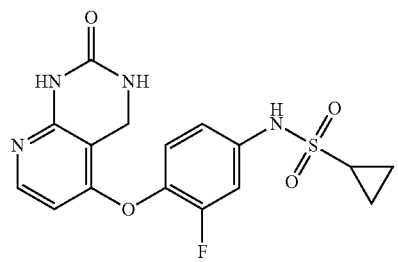 [SMILES: O=C1NCc2c(Oc3ccc(NS(=O)(=O)C4CC4)cc3F)ccnc2N1]

Cyclopropanesulfonic acid [3-fluoro-4-(2-oxo-1,2,3,4-tetrahydro-pyrido[2,3-d]pyrimidin-5-yloxy)-phenyl]-amide (238)

The title compound was synthesized according to the procedure described for the preparation of Example 62 using cyclopropanesulfonyl chloride, followed by removing 3(4-methoxybenzyl) group with the procedure described for the preparation of Example 3. LC-MS (M+1=379, obsd.=379).

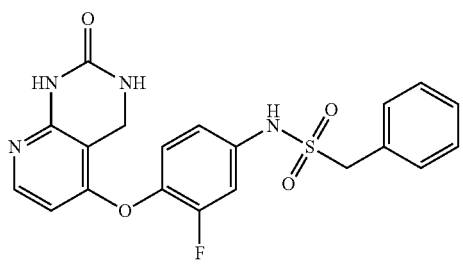 [SMILES: O=C1NCc2c(Oc3ccc(NS(=O)(=O)Cc4ccccc4)cc3F)ccnc2N1]

N-[3-Fluoro-4-(2-oxo-1,2,3,4-tetrahydro-pyrido[2,3-d]pyrimidin-5-yloxy)-phenyl]-C-phenyl-methane-sulfonamide (239)

The title compound was synthesized according to the procedure described for the preparation of Example 62 using phenyl-methanesulfonyl chloride, followed by removing 3-(4-methoxybenzyl) group with the procedure described for the preparation of Example 3. LC-MS (M+1=429, obsd.=429).

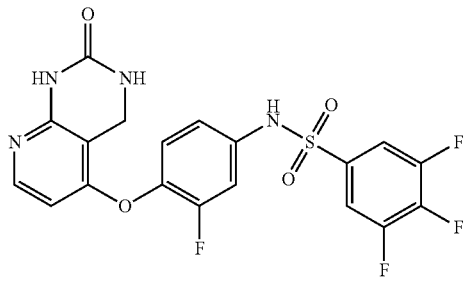 [SMILES: O=C1NCc2c(Oc3ccc(NS(=O)(=O)c4cc(F)c(F)c(F)c4)cc3F)ccnc2N1]

3,4,5-Trifluoro-N-[3-fluoro-4-(2-oxo-1,2,3,4-tetrahydro-pyrido[2,3-d]pyrimidin-5-yloxy)-phenyl]-benzenesulfonamide (240)

The title compound was synthesized according to the procedure described for the preparation of Example 62 using 3,4,5-trifluorobenzenesulfonyl chloride, followed by removing 3-(4-methoxybenzyl) group with the procedure described for the preparation of Example 3. LC-MS (M+1=469, obsd.=469).

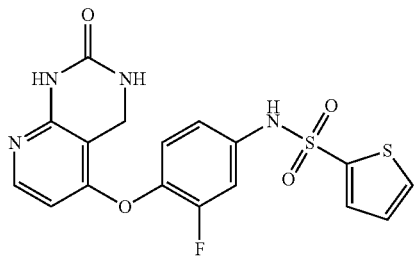 [SMILES: O=C1NCc2c(Oc3ccc(NS(=O)(=O)c4cccs4)cc3F)ccnc2N1]

Thiophene-2-sulfonic acid [3-fluoro-4-(2-oxo-1,2,3,4-tetrahydro-pyrido[2,3-d]pyrimidin-5-yloxy)-phenyl]-amide (241)

The title compound was synthesized according to the procedure described for the preparation of Example 62 using thiophene-2-sulfonyl chloride, followed by removing 3-(4-methoxybenzyl) group with the procedure described for the preparation of Example 3. LC-MS (M+1=421, obsd.=421).

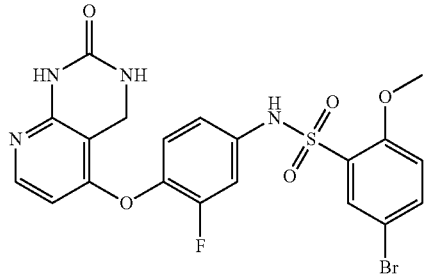 [SMILES: COc1ccc(Br)cc1S(=O)(=O)Nc1ccc(Oc2ccnc3c2CNC(=O)N3)c(F)c1]

5-Bromo-N-[3-fluoro-4-(2-oxo-1,2,3,4-tetrahydro-pyrido[2,3-d]pyrimidin-5-yloxy)-phenyl]-2-methoxy-benzenesulfonamide (242)

The title compound was synthesized according to the procedure described for the preparation of Example 62 using 5-bromo-2-methoxybenzenesulfonyl chloride, followed by removing 3-(4-methoxybenzyl) group with the procedure described for the preparation of Example 3. LC-MS (M+1=523, obsd.=523).

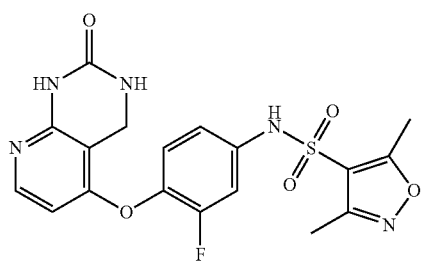 [SMILES: Cc1noc(C)c1S(=O)(=O)Nc1ccc(Oc2ccnc3c2CNC(=O)N3)c(F)c1]

3,5-Dimethyl-isoxazole-4-sulfonic acid [3-fluoro-4-(2-oxo-1,2,3,4-tetrahydro-pyrido[2,3-d]pyrimidin-5-yloxy)-phenyl]-amide (243)

The title compound was synthesized according to the procedure described for the preparation of Example 62 using 3,5-dimethyl-isoxazole-4-sulfonyl chloride, followed by removing 3-(4-methoxybenzyl) group with the procedure described for the preparation of Example 3. LC-MS (M+1=434, obsd.=434).

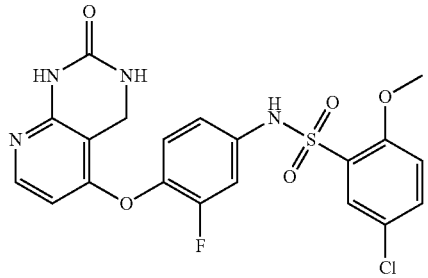 [SMILES: COc1ccc(Cl)cc1S(=O)(=O)Nc1ccc(Oc2ccnc3c2CNC(=O)N3)c(F)c1]

5-Chloro-N-[3-fluoro-4-(2-oxo-1,2,3,4-tetrahydro-pyrido[2,3-d]pyrimidin-5-yloxy)-phenyl]-2-methoxy-benzenesulfonamide (244)

The title compound was synthesized according to the procedure described for the preparation of Example 62 using 5-chloro-2-methoxybenzenesulfonyl chloride, followed by removing 3-(4-methoxybenzyl) group with the procedure described for the preparation of Example 3. LC-MS (M+1=479, obsd.=479).

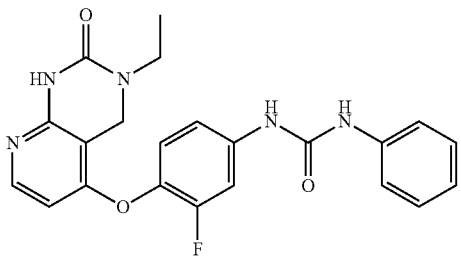 [SMILES: CCN1Cc2c(Oc3ccc(NC(=O)Nc4ccccc4)cc3F)ccnc2NC1=O]

1-[4-(3-Ethyl-2-oxo-1,2,3,4-tetrahydro-pyrido[2,3-d]pyrimidin-5-yloxy)-3-fluoro-phenyl]-3-phenyl-urea (245)

The title compound was synthesized according to the procedure described for the preparation of Example 63 using 82 and phenyl isocyanate. LC-MS (M+1=422, obsd.=422).

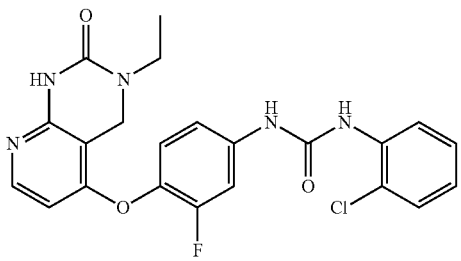 [SMILES: CCN1Cc2c(Oc3ccc(NC(=O)Nc4ccccc4Cl)cc3F)ccnc2NC1=O]

1-(2-Chloro-phenyl)-3-[4-(3-ethyl-2-oxo-1,2,3,4-tetrahydro-pyrido[2,3-d]pyrimidin-5-yloxy)-3-fluoro-phenyl]-urea (246)

The title compound was synthesized according to the procedure described for the preparation of Example 63 using 82 and 2-chlorophenyl isocyanate. LC-MS (M+1=456, obsd.=456).

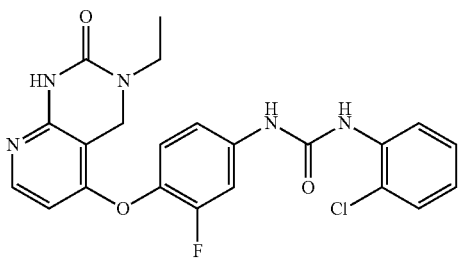 [SMILES: CCN1Cc2c(Oc3ccc(NC(=O)Nc4ccccc4Cl)cc3F)ccnc2NC1=O]

1-(2-Chloro-phenyl)-3-[4-(3-ethyl-2-oxo-1,2,3,4-tetrahydro-pyrido[2,3-d]pyrimidin-5-yloxy)-3-fluoro-phenyl]-urea (247)

The title compound was synthesized according to the procedure described for the preparation of Example 63 using 82 and 2-chlorophenyl isocyanate. LC-MS (M+1=456, obsd.=456).

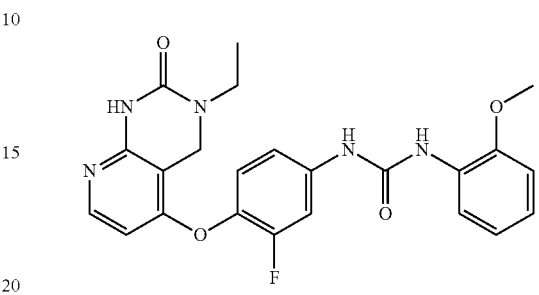

1-[4-(3-Ethyl-2-oxo-1,2,3,4-tetrahydro-pyrido[2,3-d]pyrimidin-5-yloxy)-3-fluoro-phenyl]-3-(2-methoxy-phenyl)-urea (248)

The title compound was synthesized according to the procedure described for the preparation of Example 63 using 82 and 2-methoxyphenyl isocyanate. LC-MS (M+1=452, obsd.=452).

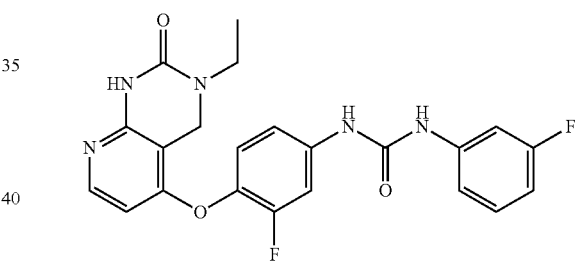

1-[4-(3-Ethyl-2-oxo-1,2,3,4-tetrahydro-pyrido[2,3-d]pyrimidin-5-yloxy)-3-fluoro-phenyl]-3-(3-fluoro-phenyl)-urea (249)

The title compound was synthesized according to the procedure described for the preparation of Example 63 using 82 and 3-fluorophenyl isocyanate. LC-MS (M+1=440, obsd.=440).

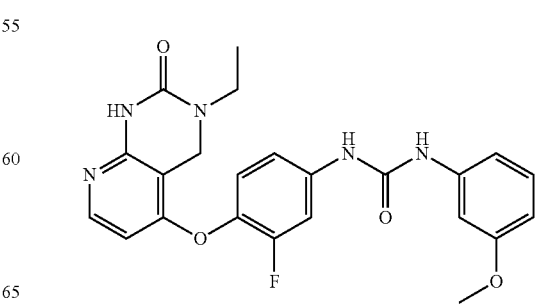

1-[4-(3-Ethyl-2-oxo-1,2,3,4-tetrahydro-pyrido[2,3-d]pyrimidin-5-yloxy)-3-fluoro-phenyl]-3-(3-methoxy-phenyl)-urea (250)

The title compound was synthesized according to the procedure described for the preparation of Example 63 using 82 and 3-methoxyphenyl isocyanate. LC-MS (M+1=452, obsd.=452).

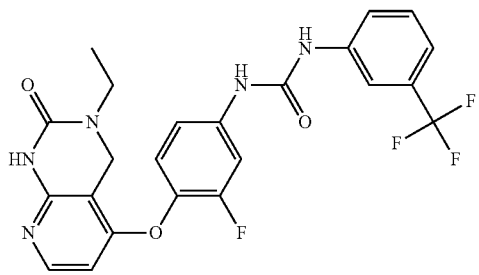 [SMILES: CCN1Cc2c(Oc3ccc(NC(=O)Nc4cccc(C(F)(F)F)c4)cc3F)ccnc2NC1=O]

1-[4-(3-Ethyl-2-oxo-1,2,3,4-tetrahydro-pyrido[2,3-d]pyrimidin-5-yloxy)-3-fluoro-phenyl]-3-(3-trifluoromethyl-phenyl)-urea (251)

The title compound was synthesized according to the procedure described for the preparation of Example 63 using 82 and 3-trifluoromethylphenyl isocyanate. LC-MS (M+1=490, obsd.=490).

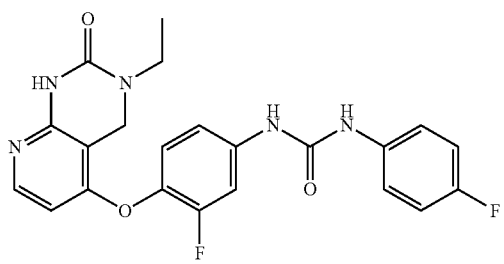 [SMILES: CCN1Cc2c(Oc3ccc(NC(=O)Nc4ccc(F)cc4)cc3F)ccnc2NC1=O]

1-[4-(3-Ethyl-2-oxo-1,2,3,4-tetrahydro-pyrido[2,3-d]pyrimidin-5-yloxy)-3-fluoro-phenyl]-3-(4-fluoro-phenyl)-urea (252)

The title compound was synthesized according to the procedure described for the preparation of Example 63 using 82 and 4-fluorophenyl isocyanate. LC-MS (M+1=440, obsd.=440).

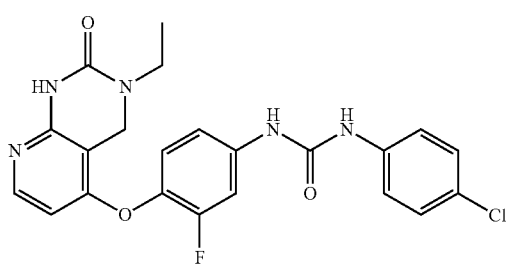 [SMILES: CCN1Cc2c(Oc3ccc(NC(=O)Nc4ccc(Cl)cc4)cc3F)ccnc2NC1=O]

1-(4-Chloro-phenyl)-3-[4-(3-ethyl-2-oxo-1,2,3,4-tetrahydro-pyrido[2,3-d]pyrimidin-5-yloxy)-3-fluoro-phenyl]-urea (253)

The title compound was synthesized according to the procedure described for the preparation of Example 63 using 82 and 4-chlorophenyl isocyanate. LC-MS (M+1=456, obsd.=456).

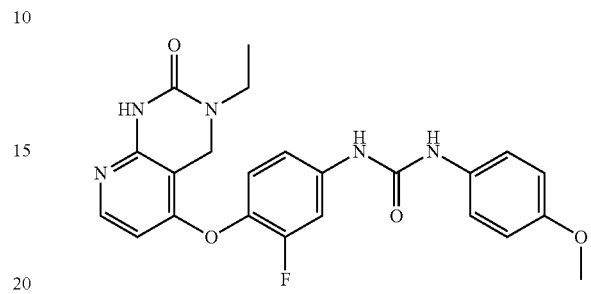

1-[4-(3-Ethyl-2-oxo-1,2,3,4-tetrahydro-pyrido[2,3-d]pyrimidin-5-yloxy)-3-fluoro-phenyl]-3-(4-methoxy-phenyl)-urea (254)

The title compound was synthesized according to the procedure described for the preparation of Example 63 using 82 and 4-methoxyphenyl isocyanate. LC-MS (M+1=452, obsd.=452).

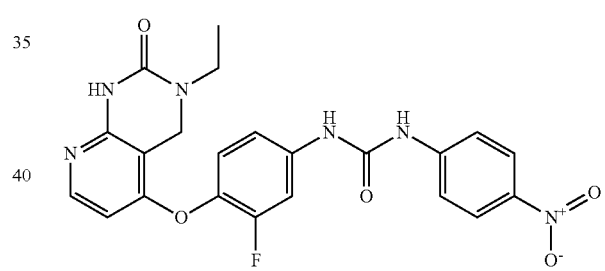

1-[4-(3-Ethyl-2-oxo-1,2,3,4-tetrahydro-pyrido[2,3-d]pyrimidin-5-yloxy)-3-fluoro-phenyl]-3-(4-nitro-phenyl)-urea (255)

The title compound was synthesized according to the procedure described for the preparation of Example 63 using 82 and 4-nitrophenyl isocyanate. LC-MS (M+1=467, obsd.=467).

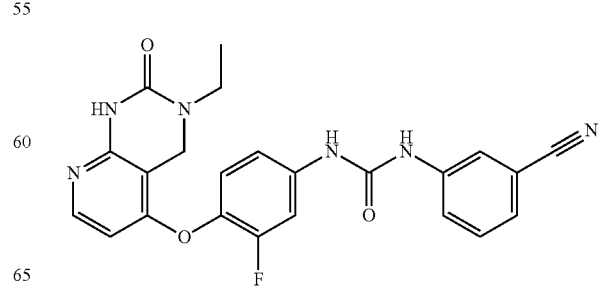

1-(3-Cyano-phenyl)-3-[4-(3-ethyl-2-oxo-1,2,3,4-tetrahydro-pyrido[2,3-d]pyrimidin-5-yloxy)-3-fluoro-phenyl]-urea (256)

The title compound was synthesized according to the procedure described for the preparation of Example 63 using 82 and 3-cyanophenyl isocyanate. LC-MS (M+1=447, obsd.=447).

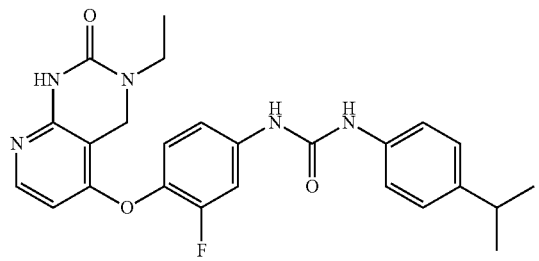 [SMILES: CCN1Cc2c(Oc3ccc(NC(=O)Nc4ccc(C(C)C)cc4)cc3F)ccnc2NC1=O]

1-[4-(3-Ethyl-2-oxo-1,2,3,4-tetrahydro-pyrido[2,3-d]pyrimidin-5-yloxy)-3-fluoro-phenyl]-3-(4-isopropyl-phenyl)-urea (257)

The title compound was synthesized according to the procedure described for the preparation of Example 63 using 82 and 4-isopropylphenyl isocyanate. LC-MS (M+1=464, obsd.=464).

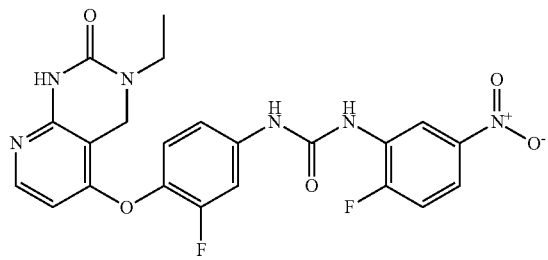 [SMILES: CCN1Cc2c(Oc3ccc(NC(=O)Nc4cc([N+](=O)[O-])ccc4F)cc3F)ccnc2NC1=O]

RON IC$_{50}$="+"

1-[4-(3-Ethyl-2-oxo-1,2,3,4-tetrahydro-pyrido[2,3-d]pyrimidin-5-yloxy)-3-fluoro-phenyl]-3-(2-fluoro-5-nitro-phenyl)-urea (258)

The title compound was synthesized according to the procedure described for the preparation of Example 63 using 82 and 2-fluoro-5-nitrophenyl isocyanate. LC-MS (M+1=485, obsd.=485).

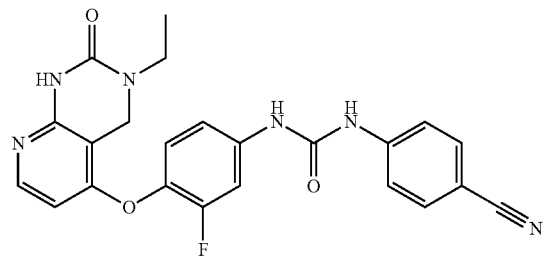 [SMILES: CCN1Cc2c(Oc3ccc(NC(=O)Nc4ccc(C#N)cc4)cc3F)ccnc2NC1=O]

1-(4-Cyano-phenyl)-3-[4-(3-ethyl-2-oxo-1,2,3,4-tetrahydro-pyrido[2,3-d]pyrimidin-5-yloxy)-3-fluoro-phenyl]-urea (259)

The title compound was synthesized according to the procedure described for the preparation of Example 63 using 82 and 4-cyanophenyl isocyanate. LC-MS (M+1=447, obsd.=447).

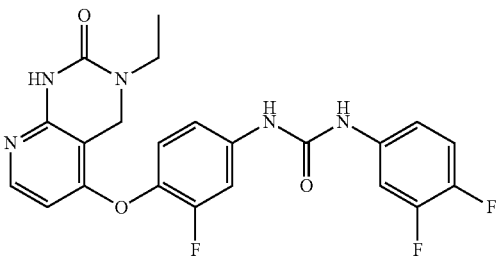 [SMILES: CCN1Cc2c(Oc3ccc(NC(=O)Nc4ccc(F)c(F)c4)cc3F)ccnc2NC1=O]

1-(3,4-Difluoro-phenyl)-3-[4-(3-ethyl-2-oxo-1,2,3,4-tetrahydro-pyrido[2,3-d]pyrimidin-5-yloxy)-3-fluoro-phenyl]-urea (260)

The title compound was synthesized according to the procedure described for the preparation of Example 63 using 82 and 3,4-difluorophenyl isocyanate. LC-MS (M+1=458, obsd.=458).

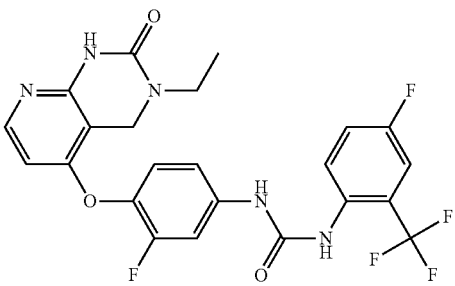 [SMILES: CCN1Cc2c(Oc3ccc(NC(=O)Nc4ccc(F)cc4C(F)(F)F)cc3F)ccnc2NC1=O]

1-[4-(3-Ethyl-2-oxo-1,2,3,4-tetrahydro-pyrido[2,3-d]pyrimidin-5-yloxy)-3-fluoro-phenyl]-3-(4-fluoro-2-trifluoromethyl-phenyl)-urea (261)

The title compound was synthesized according to the procedure described for the preparation of Example 63 using 82 and 4-chloro-2-trifluoromethylphenyl isocyanate. LC-MS (M+1=508, obsd.=508).

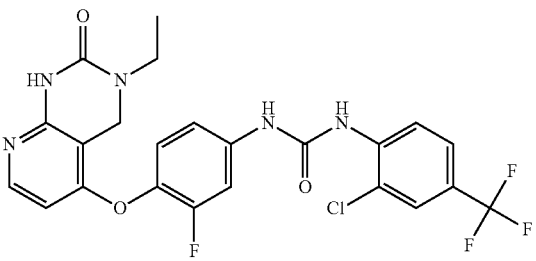 [SMILES: CCN1Cc2c(Oc3ccc(NC(=O)Nc4ccc(C(F)(F)F)cc4Cl)cc3F)ccnc2NC1=O]

1-(2-Chloro-4-trifluoromethyl-phenyl)-3-[4-(3-ethyl-2-oxo-1,2,3,4-tetrahydro-pyrido[2,3-d]pyrimidin-5-yloxy)-3-fluoro-phenyl]-urea (262)

The title compound was synthesized according to the procedure described for the preparation of Example 63 using 82 and 2-chloro-4-trifluoromethylphenyl isocyanate. LC-MS (M+1=524, obsd.=524).

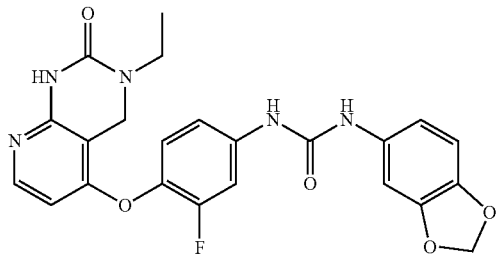 [SMILES: CCN1Cc2c(Oc3ccc(NC(=O)Nc4ccc5c(c4)OCO5)cc3F)ccnc2NC1=O]

RON IC$_{50}$="++"

1-Benzo[1,3]dioxol-5-yl-3-[4-(3-ethyl-2-oxo-1,2,3,4-tetrahydro-pyrido[2,3-d]pyrimidin-5-yloxy)-3-fluoro-phenyl]-urea (263)

The title compound was synthesized according to the procedure described for the preparation of Example 63 using 82 and 3,4-(methylenedioxy)phenyl isocyanate. LC-MS (M+1=466, obsd.=466).

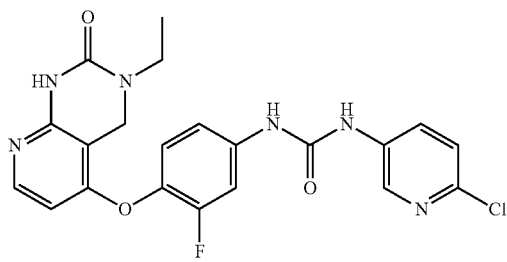 [SMILES: CCN1Cc2c(Oc3ccc(NC(=O)Nc4ccc(Cl)nc4)cc3F)ccnc2NC1=O]

RON IC$_{50}$="+"

1-(6-Chloro-pyridin-3-yl)-3-[4-(3-ethyl-2-oxo-1,2,3,4-tetrahydro-pyrido[2,3-d]pyrimidin-5-yloxy)-3-fluoro-phenyl]-urea (264)

The title compound was synthesized according to the procedure described for the preparation of Example 63 using 82 and 2-chloro-5-isocyanatopyridine. LC-MS (M+1=457, obsd.=457).

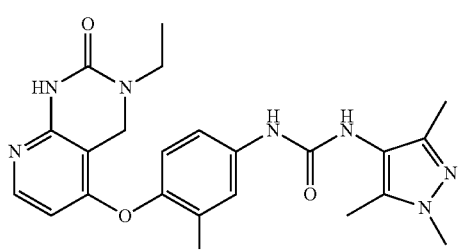

1-[4-(3-Ethyl-2-oxo-1,2,3,4-tetrahydro-pyrido[2,3-d]pyrimidin-5-yloxy)-3-fluoro-phenyl]-3-(1,3,5-trimethyl-1H-pyrazol-4-yl)-urea (265)

The title compound was synthesized according to the procedure described for the preparation of Example 63 using 82 and 4-isocyanato-1,3,5-trimethyl-1H-pyrazole. LC-MS (M+1=454, obsd.=454).

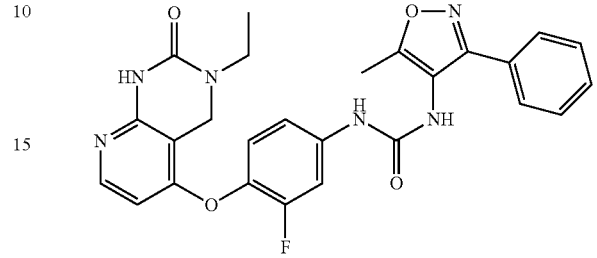

RON IC$_{50}$="+"

1-[4-(3-Ethyl-2-oxo-1,2,3,4-tetrahydro-pyrido[2,3-d]pyrimidin-5-yloxy)-3-fluoro-phenyl]-3-(5-methyl-3-phenyl-isoxazol-4-yl)-urea (266)

The title compound was synthesized according to the procedure described for the preparation of Example 63 using 82 and 5-methyl-3-phenyl-4-isoxazolyl isocyanate. LC-MS (M+1=503, obsd.=503).

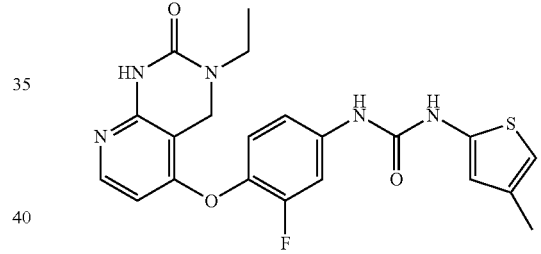

RON IC$_{50}$="++"

1-[4-(3-Ethyl-2-oxo-1,2,3,4-tetrahydro-pyrido[2,3-d]pyrimidin-5-yloxy)-3-fluoro-phenyl]-3-(4-methyl-thiophen-2-yl)-urea (267)

The title compound was synthesized according to the procedure described for the preparation of Example 63 using 82 and 4-methyl-thiophen-2-yl isocyanate. LC-MS (M+1=442, obsd.=442).

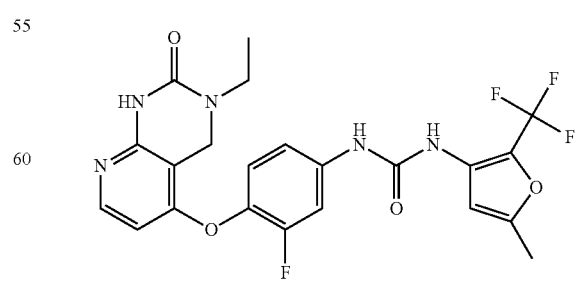

RON IC$_{50}$="++"

1-[4-(3-Ethyl-2-oxo-1,2,3,4-tetrahydro-pyrido[2,3-d]pyrimidin-5-yloxy)-3-fluoro-phenyl]-3-(5-methyl-2-trifluoromethyl-furan-3-yl)-urea (268)

The title compound was synthesized according to the procedure described for the preparation of Example 63 using 82 and 5-methyl-2-trifluoromethyl-3-furyl isocyanate. LC-MS (M+1=494, obsd.=494).

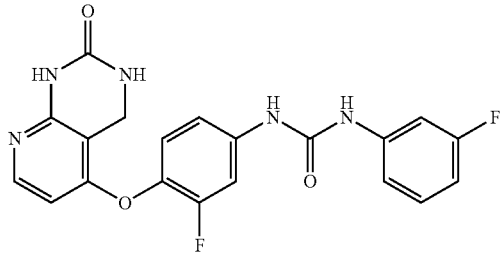 [SMILES: O=C(Nc1cccc(F)c1)Nc1ccc(Oc2ccnc3c2CNC(=O)N3)c(F)c1]

RON IC$_{50}$="++"

1-[3-Fluoro-4-(2-oxo-1,2,3,4-tetrahydro-pyrido[2,3-d]pyrimidin-5-yloxy)-phenyl]-3-(3-fluoro-phenyl)-urea (269)

The title compound was synthesized according to the procedure described for the preparation of Example 63 using 3-fluorophenyl isocyanate, followed by removing 3-(4-methoxybenzyl) group with the procedure described for the preparation of Example 3. LC-MS (M+1=412, obsd.=412).

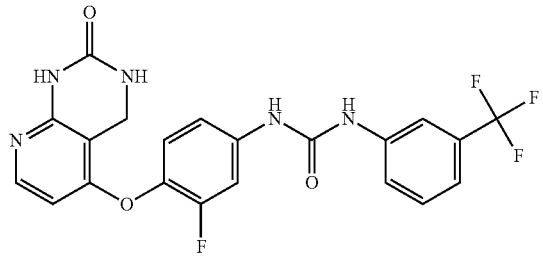 [SMILES: O=C(Nc1cccc(C(F)(F)F)c1)Nc1ccc(Oc2ccnc3c2CNC(=O)N3)c(F)c1]

RON IC$_{50}$="++"

1-[3-Fluoro-4-(2-oxo-1,2,3,4-tetrahydro-pyrido[2,3-d]pyrimidin-5-yloxy)-phenyl]-3-(3-trifluoromethyl-phenyl)-urea (270)

The title compound was synthesized according to the procedure described for the preparation of Example 63 using 3-trifluoromethylphenyl isocyanate, followed by removing 3-(4-methoxybenzyl) group with the procedure described for the preparation of Example 3. LC-MS (M+1=462, obsd.=462).

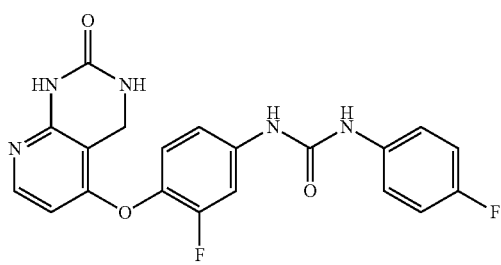 [SMILES: O=C(Nc1ccc(F)cc1)Nc1ccc(Oc2ccnc3c2CNC(=O)N3)c(F)c1]

1-[3-Fluoro-4-(2-oxo-1,2,3,4-tetrahydro-pyrido[2,3-d]pyrimidin-5-yloxy)-phenyl]-3-(4-fluoro-phenyl)-urea (271)

The title compound was synthesized according to the procedure described for the preparation of Example 63 using 4-fluorophenyl isocyanate, followed by removing 3-(4-methoxybenzyl) group with the procedure described for the preparation of Example 3. LC-MS (M+1=412, obsd.=412).

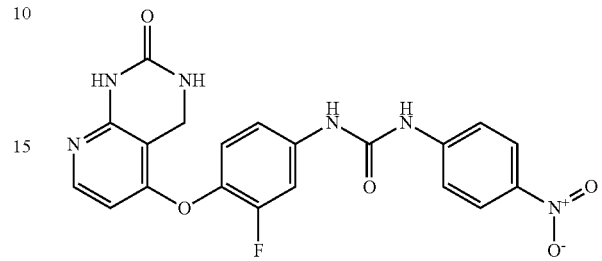

RON IC$_{50}$="++"

1-[3-Fluoro-4-(2-oxo-1,2,3,4-tetrahydro-pyrido[2,3-d]pyrimidin-5-yloxy)-phenyl]-3-(4-nitro-phenyl)-urea (272)

The title compound was synthesized according to the procedure described for the preparation of Example 63 using 4-nitrophenyl isocyanate, followed by removing 3-(4-methoxybenzyl) group with the procedure described for the preparation of Example 3. LC-MS (M+1=439, obsd.=439).

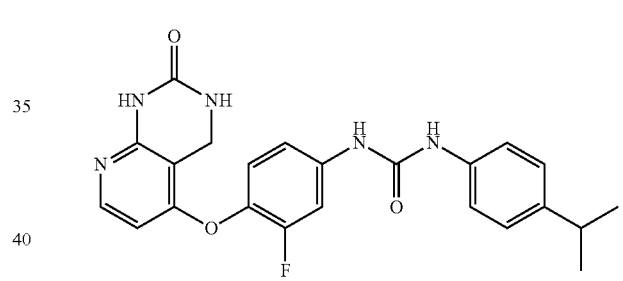

RON IC$_{50}$="+++"

1-[3-Fluoro-4-(2-oxo-1,2,3,4-tetrahydro-pyrido[2,3-d]pyrimidin-5-yloxy)-phenyl]-3-(4-isopropyl-phenyl)-urea (273)

The title compound was synthesized according to the procedure described for the preparation of Example 63 using 4-isopropylphenyl isocyanate, followed by removing 3-(4-methoxybenzyl) group with the procedure described for the preparation of Example 3. LC-MS (M+1=436, obsd.=436).

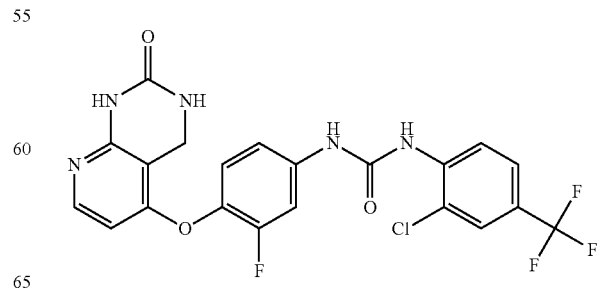

RON IC$_{50}$="+"

1-(2-Chloro-4-trifluoromethyl-phenyl)-3-[3-fluoro-4-(2-oxo-1,2,3,4-tetrahydro-pyrido[2,3-d]pyrimidin-5-yloxy)-phenyl]-urea (274)

The title compound was synthesized according to the procedure described for the preparation of Example 63 using 4-trifluoromethylphenyl isocyanate, followed by removing 3-(4-methoxybenzyl) group with the procedure described for the preparation of Example 3. LC-MS (M+1=496, obsd.=496).

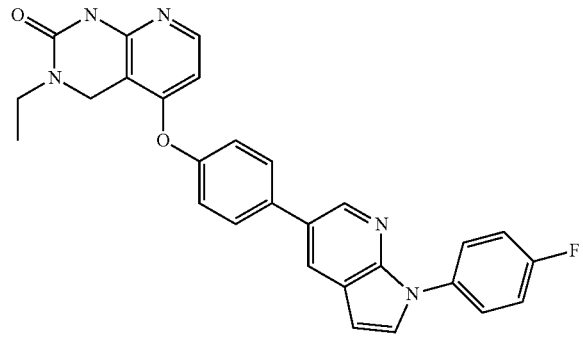 [SMILES: CCN1Cc2c(Oc3ccc(-c4cnc5c(ccn5-c5ccc(F)cc5)c4)cc3)ccnc2NC1=O]

3-ethyl-5-{4-[1-(4-fluorophenyl)-1H-pyrrolo[2,3-b]pyridin-5-yl]phenoxy}-3,4-dihydropyrido[2,3-d]pyrimidin-2(1H)-one (275)

Into a 10-mL microwave vial equipped with a stir-bar was added 5-chloro-3-ethyl-3,4-dihydropyrido[2,3-d]pyrimidin-2(1H)-one (30.00 mg; 0.14 mmol), 4-[1-(4-fluorophenyl)-1H-pyrrolo[2,3-b]pyridin-5-yl]phenol (64.70 mg; 0.21 mmol) and cesium carbonate (138.55 mg; 0.43 mmol). The mixture was suspended in DMF (2.00 ml). The vial was then loaded onto the microwave reactor and run at 160° C. for 2 h. The reaction mixture was filtered through a bed of silica under reduced pressure. The crude material was purified via Biotage eluting with a gradient of 50 to 100% EtOAc in Hexanes to provide 275 as an off-white solid. LC-MS (M+H=480, obsd.=480). $^1$H-NMR: (DMSO-D6) δ 9.66 (s, 1H); 8.64 (d, 1H); 8.37 (d, 1H); 7.97 (m, 4H); 7.84 (d, 2H); 7.41 (t, 2H); 7.30 (d, 2H), 6.78 (d, 1H); 6.27 (d, 1H); 4.54 (s, 2H); 3.40 (q, 2H); 1.11 (t, 3H).

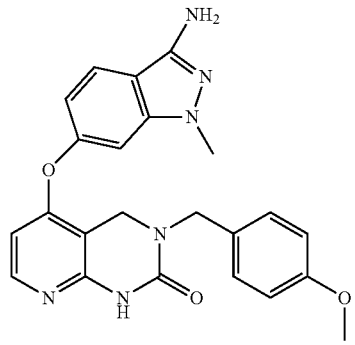 [SMILES: COc1ccc(CN2Cc3c(Oc4ccc5c(N)nn(C)c5c4)ccnc3NC2=O)cc1]

5-(3-Amino-1-methyl-1H-indazol-6-yloxy)-3-(4-methoxy-benzyl)-3,4-dihydro-1H-pyrido[2,3-d]pyrimidin-2-one (276)

Suspended 5-chloro-3-(4-methoxy-benzyl)-3,4-dihydro-1h-pyrido[2,3-d]pyrimidin-2-one (400.00 mg; 1.32 mmol; 1.00 eq.), 3-amino-1-methyl-1h-indazol-6-ol (268.61 mg; 1.65 mmol; 1.25 eq.) and cesium carbonate (858.15 mg; 2.63 mmol; 2.00 eq.) in DMF (4.00 ml). Heated in a microwave at 130° C. for 90 min. The reaction was concentrated, redissolved in DMSO (20 mL) and filtered through celite. Purified filtrate via prep HPLC to afford 400 mg (56%) of compound 276 as a tan solid. LC-MS (M+H=431, obsd.=431)

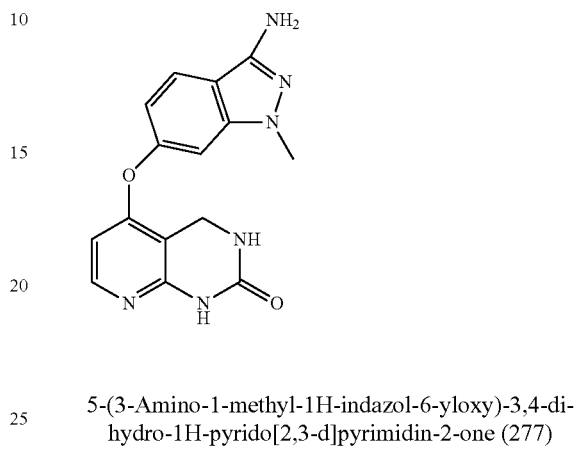

5-(3-Amino-1-methyl-1H-indazol-6-yloxy)-3,4-dihydro-1H-pyrido[2,3-d]pyrimidin-2-one (277)

Compound 276 (25.00 mg; 0.06 mmol; 1.00 eq.) was dissolved in trifluoroacetic acid (2.00 ml). The vessel was sealed and heated at 75 degrees C. for two days. The reaction was concentrated, redissolved in DMSO, treated with Et3N to get pH ~8, and then purified via prep HPLC to afford 17mg (69%) of 277 as a white solid. LC-MS (M+H=311, obsd.=311).

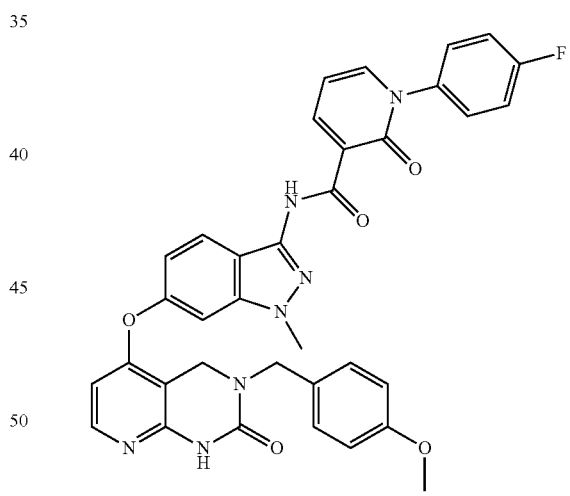

1-(4-Fluoro-phenyl)-2-oxo-1,2-dihydro-pyridine-3-carboxylicacid{6-[3-(4-methoxy-benzyl)-2-oxo-1,2,3,4-tetrahydro-pyrido[2,3-d]pyrimidin-5-yloxy]-1-methyl-1H-indazol-3-yl}-amide (278)

A solution of compound 276 (100.00 mg; 0.23 mmol; 1.00 eq.), 1-(4-fluoro-phenyl)-2-oxo-1,2-dihydro-pyridine-3-carboxylic acid (59.59 mg; 0.26 mmol; 1.10 eq.), pybop (157.16 mg; 0.30 mmol; 1.30 eq.), DMF (4.00 ml), and N,N-diisopropylethylamine (115.48 μl; 0.70 mmol; 3.00 eq.) was stirred at room temperature for 22 hours. The reaction was concentrated, redissolved in DMSO and purified via prep HPLC to afford 28 mg (16%) of 278 as an off-white solid. LC-MS (M+H=646, obsd.=646).

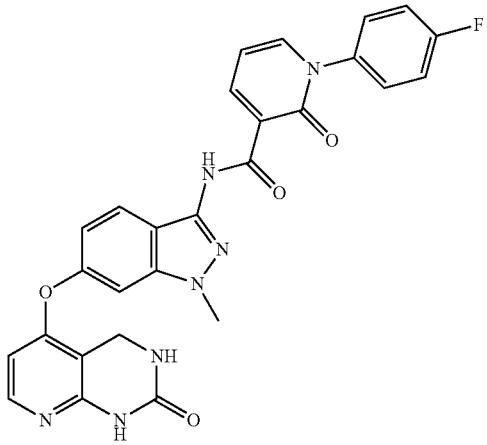 [SMILES: Cn1nc(NC(=O)c2cccn(-c3ccc(F)cc3)c2=O)c2ccc(Oc3ccnc4c3CNC(=O)N4)cc21]

1-(4-Fluoro-phenyl)-2-oxo-1,2-dihydro-pyridine-3-carboxylic acid[1-methyl-6-(2-oxo-1,2,3,4-tetrahydro-pyrido[2,3-d]pyrimidin-5-yloxy)-1H-indazol-3-yl]-amide (279)

A solution of compound 278 (22.00 mg; 0.03 mmol; 1.00 eq.) and trifluoroacetic acid (2.00 ml) was stirred at 80 degrees C. overnight. The reaction was stirred at 80 degrees C. for 22 hr. The reaction was concentrated, redissolved in DMSO, and treated with Et3N to pH 8. The solution was then purified directly via prep HPLC to afford 13 mg (60%) of 279 as a yellow solid. LC-MS (M+H=526, obsd.=526).

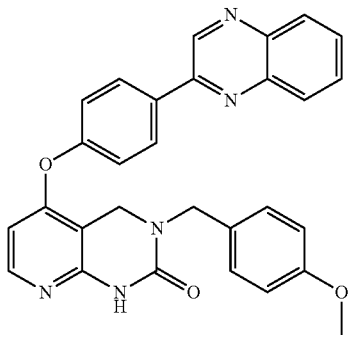 [SMILES: COc1ccc(CN2Cc3c(Oc4ccc(-c5cnc6ccccc6n5)cc4)ccnc3NC2=O)cc1]

3-(4-Methoxy-benzyl)-5-(4-quinoxalin-2-yl-phenoxy)-3,4-dihydro-1H-pyrido[2,3-d]pyrimidin-2-one (280)

A suspension of 5-chloro-3-(4-methoxy-benzyl)-3,4-dihydro-1h-pyrido[2,3-d]pyrimidin-2-one (100.00 mg; 0.33 mmol; 1.00 eq.), 4-quinoxalin-2-ylphenol (91.46 mg; 0.41 mmol; 1.25 eq.), and cesium carbonate (214.54 mg; 0.66 mmol; 2.00 eq.) in DMF (2.00 ml) was heated in a microwave at 130° C. for 4 hours. The reaction was concentrated, redissolved in DMSO, syringe filtered, and purified via prep HPLC to afford 69 mg of 280 as an off-white solid. LC-MS (M+H=490, obsd.=490).

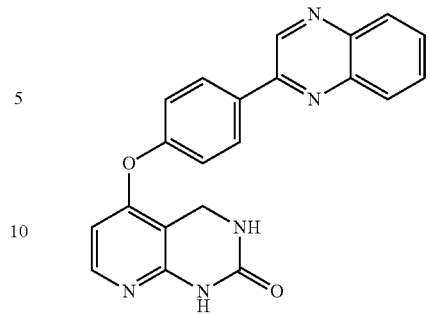

5-(4-Quinoxalin-2-yl-phenoxy)-3,4-dihydro-1H-pyrido[2,3-d]pyrimidin-2-one (281)

The title compound was synthesized according to the procedure described for the preparation of example 279 using 280 as starting material. Yielded 4 mg (7%) of 281 as a white solid. LC-MS (M+H=370, obsd.=370).

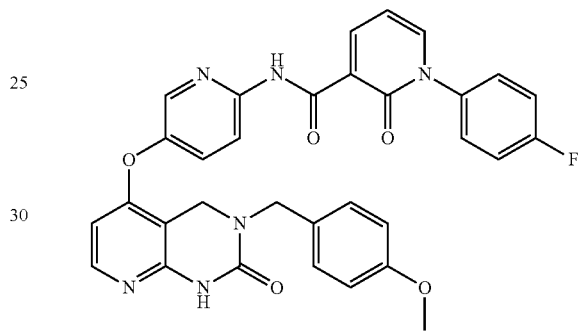

1-(4-Fluoro-phenyl)-2-oxo-1,2-dihydro-pyridine-3-carboxylic acid {5-[3-(4-methoxy-benzyl)-2-oxo-1,2,3,4-tetrahydro-pyrido[2,3-d]pyrimidin-5-yloxy]-pyridin-2-yl}-amide (282)

A solution of 5-[(6-aminopyridin-3-yl)oxy]-3-(4-methoxybenzyl)-3,4-dihydropyrido[2,3-d]pyrimidin-2(1H)-one (100.00 mg; 0.26 mmol; 1.00 eq.), 1-(4-fluoro-phenyl)-2-oxo-1,2-dihydro-pyridine-3-carboxylic acid (67.97 mg; 0.29 mmol; 1.10 eq.), pybop (179.26 mg; 0.34 mmol; 1.30 eq.), DMF (4.00 ml), and N,N-diisopropylethylamine (0.13 µl; 0.79 mmol; 3.00 eq.) was stirred at room temperature under N2 for 14 hours. The reaction was concentrated, redissolved in DMSO, and purified via prep HPLC to afford 49 mg (26%) of 282 as a peach-colored solid. LC-MS (M+H=593, obsd.=593).

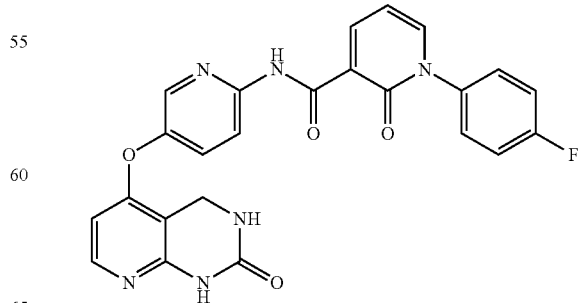

RON IC$_{50}$="+"

1-(4-Fluoro-phenyl)-2-oxo-1,2-dihydro-pyridine-3-carboxylic acid [5-(2-oxo-1,2,3,4-tetrahydro-pyrido[2,3-d]pyrimidin-5-yloxy)-pyridin-2-yl]-amide (283)

The title compound was synthesized according to the procedure described for the preparation of example 279 using 282 as starting material. Yielded 19 mg (48%) of 283 as an off-white solid. LC-MS (M+H=473, obsd.=473).

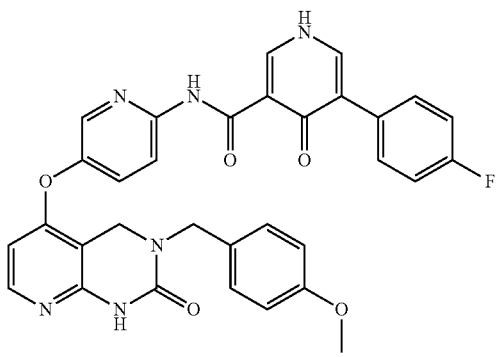 [SMILES: COc1ccc(CN2Cc3c(Oc4ccc(NC(=O)c5c[nH]cc(-c6ccc(F)cc6)c5=O)nc4)ccnc3NC2=O)cc1]

5-(4-Fluoro-phenyl)-4-oxo-1,4-dihydro-pyridine-3-carboxylic acid {5-[3-(4-methoxy-benzyl)-2-oxo-1,2,3,4-tetrahydro-pyrido[2,3-d]pyrimidin-5-yloxy]-pyridin-2-yl}-amide (284)

A solution of 5-[(6-aminopyridin-3-yl)oxy]-3-(4-methoxybenzyl)-3,4-dihydropyrido[2,3-d]pyrimidin-2(1H)-one (100.00 mg; 0.26 mmol; 1.00 eq.), 5-(4-fluoro-phenyl)-4-oxo-1,4-dihydro-pyridine-3-carboxylic acid (67.97 mg; 0.29 mmol; 1.10 eq.), pybop (179.26 mg; 0.34 mmol; 1.30 eq.), DMF (4.00 ml), and N,N-diisopropylethylamine (131.72 µl; 0.79 mmol; 3.00 eq.) was stirred at room temperature for 4 days. The reaction was concentrated, redissolved in DMSO, and purified via prep HPLC to afford 49 mg (26%) of 284 as a tan solid. LC-MS (M+H=593, obsd.=593).

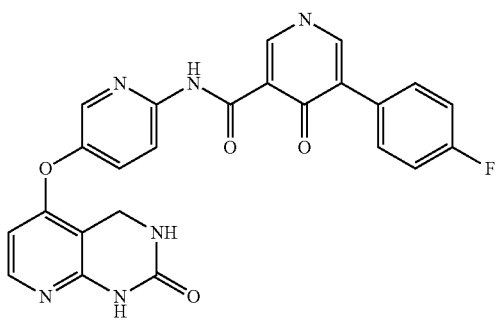 [SMILES: O=C1NCc2c(Oc3ccc(NC(=O)c4c[nH]cc(-c5ccc(F)cc5)c4=O)nc3)ccnc2N1]

5-(4-Fluoro-phenyl)-4-oxo-1,4-dihydro-pyridine-3-carboxylic acid [5-(2-oxo-1,2,3,4-tetrahydro-pyrido[2,3-d]pyrimidin-5-yloxy)-pyridin-2-yl]-amide (285)

The title compound was synthesized according to the procedure described for the preparation of example 279 using 284 as starting material. Yielded 7 mg (37%) of 285 as a brown solid. LC-MS (M+H=473, obsd.=473).

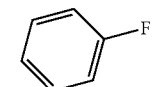

5-(4-Fluoro-phenyl)-4-oxo-1,4-dihydro-pyridine-3-carboxylic acid {5-[3-(4-methoxy-benzyl)-2-oxo-1,2,3,4-tetrahydro-pyrido[2,3-d]pyrimidin-5-yloxy]-pyridin-2-yl}-amide (286)

A solution of 5-[(3-amino-1-methyl-1H-indazol-6-yl)oxy]-3-(4-methoxybenzyl)-3,4-dihydropyrido[2,3-d]pyrimidin-2(1H)-one (100.00 mg; 0.23 mmol; 1.00 eq.),3-fluorobenzoic acid (35.80 mg; 0.26 mmol; 1.10 eq.), pybop (157.16 mg; 0.30 mmol; 1.30 eq.), DMF (4.00 ml), and N,N-diisopropylethylamine (115.48 µl; 0.70 mmol; 3.00 eq.) was stirred at room temperature for 22 hr. Additional pybop was added and the reaction was heated to 100 degrees C. but the reaction did not go to completion. The reaction was concentrated, redissolved in DMSO, and purified via prep HPLC to afford 17 mg (26%) of 3-fluoro-N-(6-{[3-(4-methoxybenzyl)-2-oxo-1,2,3,4-tetrahydropyrido[2,3-d]pyrimidin-5-yl]oxy}-1-methyl-1H-indazol-3-yl)benzamide as a yellow solid. LC-MS (M+H=553, obsd.=553).

The title compound was synthesized according to the procedure described for the preparation of example 279 using the above intermediate as starting material. Yielded 9 mg (54%) of 286 as a white solid. LC-MS (M+H=433, obsd.=433).

Biological Testing

Biochemical Assays for Aurora Activity:

The Aurora assays described here are performed on two Caliper Life Sciences systems: the LC3000 and the Desktop Profiler. The RON kinase assays are performed on the Desktop Profiler only. These provide data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of the charged phosphate group on the product (as opposed to the substrate) causes a different peptide mobility between the two peptides. This is visualized by excitation of the fluorescent label on the substrate and product peptides and represented as peaks within the analysis software.

LC3000 Method

In order to measure inhibitor activity of Aurora A inhibitors in the Caliper Life Sciences LC3000, a TTP Mosquito liquid handling instrument is used to place 0.25 ul of the appropriate concentration of inhibitor in 100% DMSO (for a dose response curve calculation) into each well of a 384-well plate. To this reaction components are added to a final volume of 25 ul:

0.067 ng/ul GST-Aurora A (Carna Biosciences 05-101. N-terminal GST fusion with full length Aurora A (1-403 amino acids), accession number NP_940835.1).
15 uM ATP (Fluka, 02055)
1 mM DTT (Sigma, D0632)
1 mM MgCl$_2$ (Sigma, M1028)
1 uM substrate peptide (sequence FITC-LRRASLG-(CONH$_2$), synthesized by Tufts Peptide Synthesis service.
100 mM HEPES pH 7.5 (Calbiochem, 391338)
0.015% Brij-35 (Sigma, B4184)

The reaction is incubated for 90 min at 25 C, and then stopped by the addition of 70 ul of Stop buffer (100 mM HEPES pH 7.5, 0.015% Brij-35, 10 mM EDTA (Sigma, E7889)).

The plate is read on a Caliper LC3000 in an Off-Chip mobility shift assay format, using the following parameters for a 12-sipper chip: screening pressure −1.8 psi, upstream voltage −2700, downstream voltage −1000. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoidal dose response curve, from which an IC$_{50}$ can be calculated using XLFit for Microsoft Excel.

Desktop Profiler Method

The Desktop Profiler utilizes the same priniciple as the LC3000 for calculating percentage conversion of a substrate to product. Caliper Life Sciences provides proprietary flash frozen pre-made 384 well plates containing selected kinases. Each column in the 384 well plate contains a particular selected kinase. A second plate, the 'substrate plate' contains a mix of fluorescently labeled peptide substrate and ATP. These are arranged in columns so that transfer for substrate plate to enzyme plate provides the correct enzyme with the correct substrate/ATP concentration. Compounds are added to a thawed enzyme plate in the desired format, in single concentrations. Reactions are initiated by transfer of the substrate/ATP mix from the substrate plate. The enzyme plate is incubated for 90 minutes at 25 C. The reaction is stopped by addition of 70 ul of Stop Buffer (100 mM HEPES pH 7.5, 0.015% Brij-35, 10 mM EDTA (Sigma, E7889)).

Reading of the plate in the Profiler is identical to the LC3000, and the ratio between substrate and product peaks provides the activity of the enzyme in that well. This is best represented by a plate heat map which colors each well by percent inhibition as compared to positive and negative controls (no inhibitors and no ATP respectively).

The invention claimed is:
1. A compound of Formula (I):

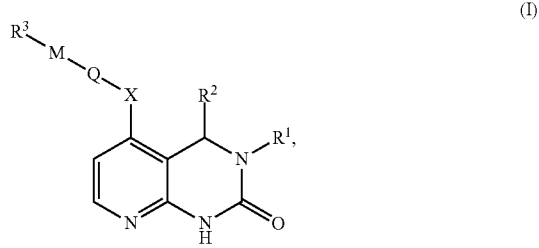

(I)

or a pharmaceutically acceptable salt thereof, wherein:

X is a bond, NH, O, S, or CH$_2$NH or CH$_2$O, wherein NH or O moieties are connected to the 2-oxo-1,2,3,4-tetrahydropyrido[2,3-d]pyrimidine moiety, Q is a 5- or 6-membered monocyclic, or 9- or 10-membered bycyclic, aromatic, homo- or heterocycle having 1 or 2 N, O and/or S atoms, which may be unsubstituted or, independently of one another, mono- or disubstituted by Hal, LA, C(Hal)$_3$, OC(Hal)$_3$, OH, SH, O(LA), NH$_2$, NH(LA), N(LA)$_2$, NO$_2$, CN, OCN, 4-fluorophenyl, oxo or SCN, M is a bond, CH$_2$, CO, SO$_2$, CONH, NHCO, NHCONH, SO$_2$NH, NHSO$_2$, NHSO$_2$NH or CH$_2$NHCO, wherein the CO moiety is connected to Q, R$^1$ is H, A, Ar or Ar-A, R$^2$ is H, or R$^1$ and R$^2$ together with the N and C atoms to which they are attached, may form a 5- or 6-membered aliphatic heterocycle having 1 or 2 N, O and/or S atoms, which may be unsubstituted or substituted by Hal, A, OH, NH$_2$ or CN, R$^3$ is A or Q, or R$^3$-M may be absent, Ar is a mono- or bicyclic aromatic homo- or heterocycle having 1 to 4 N, O and/or S atoms and 5to 10 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONH(LAr), CONA$_2$, NHCOA, NHCO(LAr), NHCONHA, NHCONH$_2$, NHSO$_2$A, CHO, COA, SO$_2$NH$_2$, SO$_2$A and/or SO$_2$Hal, A is unbranched or branched, linear or cyclic alkyl having 1, 2, 3, 4, 5, 6, 7 or 8 C atoms, in which one or two CH$_2$ groups may be replaced by an O or S atom and/or by an NH, CO, N(LA), SO$_2$, CONH, NHCO or —CH=CH— group, and in which 1-3 H atoms may be replaced by Hal, and in which one or two CH$_3$ groups may be replaced by OH, SH, NH$_2$, NH(LA), N(LA)$_2$, NHCOOH, NHCONH$_2$, N$_3$, NO$_2$ or CN, LA is unbranched or branched, linear alkyl having 1, 2, 3 or 4 C atoms, Hal is F, Cl, Br or I.

2. The compound according to claim 1 which conforms to Formula (II)

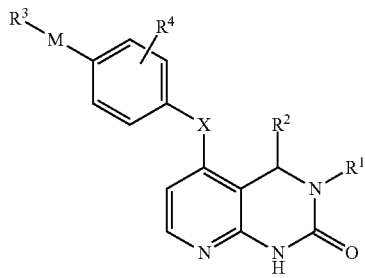

or a pharmaceutically acceptable salt thereof, wherein:

R$^3$ is phenyl, pyridyl or 2-oxo-1,2-dihydropyridinyl, each of which is unsubstituted, or substituted by R$^4$, R$^4$ is H, Hal or A.

3. The compound according to claim 1 which conforms to Formula (III)

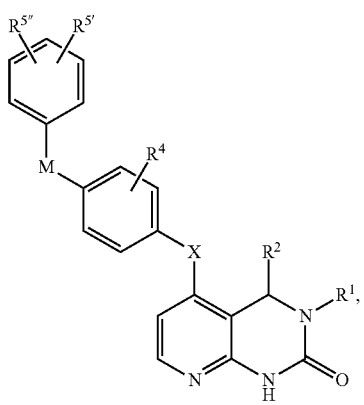

(III)

or a pharmaceutically acceptable salt thereof, wherein: $R^4$, $R^{5'}$, $R^{5''}$ each, independently of one another, are H, Hal or A.

4. The compound according to claim 1 which conforms to Formula (IV),

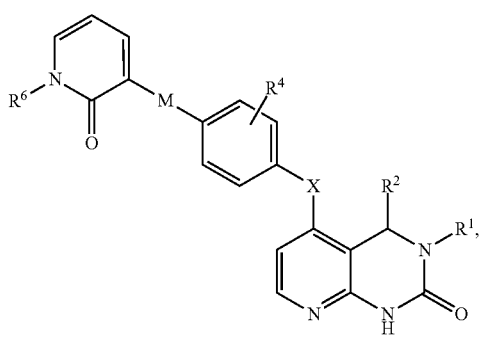

(IV)

or a pharmaceutically acceptable salt thereof, wherein:
$R^4$ is H, Hal or A, and
$R^6$ is H, A or Ar.

5. The compuound according to claim 1 which conforms to Formula (V),

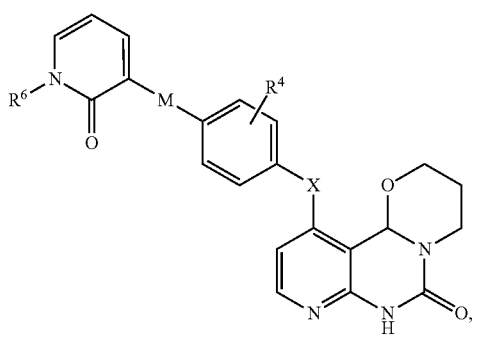

(V)

or a pharmaceutically acceptable salt thereof, wherein:
$R^4$ is H, Hal or A, and
$R^6$ is H, A or Ar.

6. The compound according to claim 1 which conforms to Formula (VI),

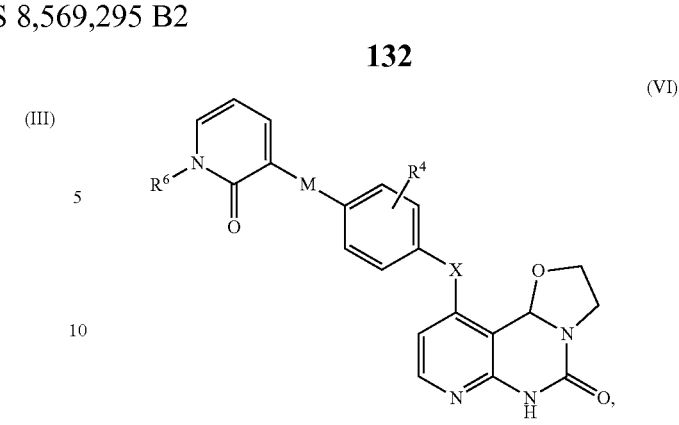

(VI)

and pharmaceutically acceptable salts, solvates or prodrugs thereof, wherein:
$R^4$ is H, Hal or A, and
$R^6$ is H, A or Ar, and the remaining substituents have the meaning indicated for Formula (I) according to claim 1.

7. The compound according to claim 1 which conforms to Formula (VII),

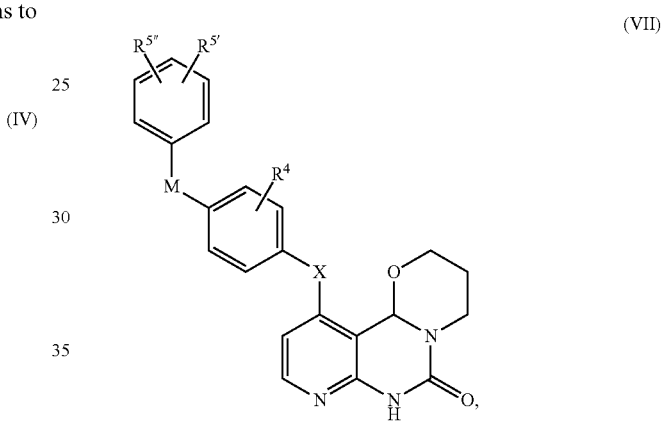

(VII)

or a pharmaceutically acceptable salt thereof, wherein:
$R^4$, $R^{5'}$, $R^{5''}$ each, independently of one another, are H, Hal or A.

8. The compound according to claim 1 which conforns, to Formula (VIII),

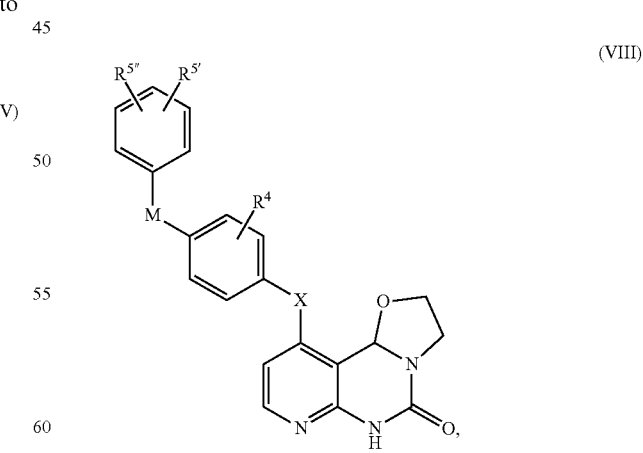

(VIII)

or a pharmaceutically acceptable salt thereof, wherein:
$R^4$, $R^{5'}$, $R^{5''}$ each, independently of one another, are H, Hal or A.

9. The compound according to claim 1, wherein the compound is selected from the group consisting of:

N-(4-(2-oxo-1,2,3,4-tetrahydropyrido[2,3-d]pyrimidin-5-ylamino) phenyl) benzamide,
4-fluoro-N-(4-(2-oxo-1,2,3,4-tetrahydropyrido[2,3-d]pyrimidin-5-ylamino)phenyl)-2-(trifluoromethyl) benzamide,
N-(4-(3-cyclopropyl-2-oxo-1,2,3,4-tetrahydropyrido[2,3-d]pyrimidin-5-ylamino) phenyl)-4-fluoro-2-(trifluoromethyl) benzamide,
4-fluoro-N-(4-(3-(1-methyl-1H-pyrazol-3-yl)-2-oxo-1,2,3,4-tetrahydropyrido[2,3-d]pyrimidin-5-ylamino)phenyl)-2-(trifluoromethyl)benzamide,
N-(4-(3-(1-methyl-1H-pyrazol-3-yl)-2-oxo-1,2,3,4-tetrahydropyrido[2,3-d]pyrimidin-5-ylamino)phenyl)benzamide,
3-fluoro-N-(3-fluoro-4-(3-methyl-2-oxo-1,2,3,4-tetrahydropyrido[2,3-d]pyrimidin-5-ylamino)phenyl)benzamide,
4-fluoro-N-(4-(3-methyl-2-oxo-1,2,3,4-tetrahydropyrido[2,3-d]pyrimidin-5-ylamino) phenyl)-2-(trifluoromethyl) benzamide,
N-(4-(3-methyl-2-oxo-1,2,3,4-tetrahydropyrido[2,3-d]pyrimidin-5-ylamino) phenyl) benzamide,
3-fluoro-N-(3-fluoro-4-(2-oxo-3-phenyl-1,2,3,4-tetrahydropyrido[2,3-d]pyrimidin-5-ylamino)phenyl)benzamide,
4-fluoro-N-(4-(2-oxo-3-phenyl-1,2,3,4-tetrahydropyrido[2,3-d]pyrimidin-5-ylamino) phenyl)-2-(trifluoromethyl)benzamide,
4-fluoro-N-(3-fluoro-4-(3-methyl-2-oxo-1,2,3,4-tetrahydropyrido[2,3-d]pyrimidin-5-ylamino) phenyl)-2-(trifluoromethyl)benzamide,
4-fluoro-N-(4-(3-(2-hydroxyethyl)-2-oxo-1,2,3,4-tetrahydropyrido[2,3-d]pyrimidin-5-ylamino)phenyl)-2-(trifluoromethyl) benzamide,
4-fluoro-N-(4-(2-oxo-3-(3-(2-oxopyrrolidin-1-yl) propyl)-1,2,3,4-tetrahydropyrido[2,3-d]pyrimidin-5-ylamino) phenyl)-2-(trifluoromethyl)benzamide,
4-fluoro-N-(4-(3-(3-hydroxypropyl)-2-oxo-1,2,3,4-tetrahydropyrido[2,3-d]pyrimidin-5-ylamino)phenyl)-2-(trifluoromethyl)benzamide,
N-(4-(3-ethyl-2-oxo-1,2,3,4-tetrahydropyrido[2,3-d]pyrimidin-5-ylamino)phenyl)-4-fluoro-2-(trifluoromethyl) benzamide,
N-(4-(3-ethyl-2-oxo-1,2,3,4-tetrahydropyrido[2,3-d]pyrimidin-5-ylamino)phenyl) benzamide,
N-(4-(3-ethyl-2-oxo-1,2,3,4-tetrahydropyrido[2,3-d]pyrimidin-5-ylamino)-3-fluorophenyl)-4-fluoro-2-(trifluoromethyl)benzamide,
N-(4-(2-oxo-3-(2,2,2-trifluoroethyl)-1,2,3,4-tetrahydropyrido[2,3-d]pyrimidin-5-ylamino)phenyl)benzamide,
4-fluoro-N-(4-(2-oxo-3-(2,2,2-trifluoroethyl)-1,2,3,4-tetrahydropyrido[2,3-d]pyrimidin-5-ylamino)phenyl)-2-(trifluoromethyl)benzamide,
2,3-difluoro-N-(2-fluoro-4-(3-methyl-2-oxo-1,2,3,4-tetrahydropyrido[2,3-d]pyrimidin-5-ylamino)phenyl)benzamide,
4-fluoro-N-(3-fluoro-4-(2-oxo-3-(2,2,2-trifluoroethyl)-1,2,3,4-tetrahydropyrido[2,3-d]pyrimidin-5-ylamino) phenyl)-2-(trifluoromethyl)benzamide,
2-fluoro-N-(3-fluoro-4-(3-methyl-2-oxo-1,2,3,4-tetrahydropyrido[2,3-d]pyrimidin-5-ylamino)phenyl)benzamide,
N-{3-fluoro-4-[(2-oxo-1,2,3,4-tetrahydropyrido[2,3-d]pyrimidin-5-yl)oxy]phenyl}-1-(4-fluorophenyl)-2-oxo-1,2-dihydropyridine-3-carboxamide,
2,5-dichloro-N-{3-fluoro-4-[(2-oxo-1,2,3,4-tetrahydropyrido[2,3-d]pyrimidin-5-yl)oxy]phenyl}-nicotinamide,
3-bromo-N-{3-fluoro-4-[(2-oxo-1,2,3,4-tetrahydropyrido[2,3-d]pyrimidin-5-yl)oxy]phenyl}-benzamide,
N-(3-chlorophenyl)-N'-{3-fluoro-4-[(2-oxo-1,2,3,4-tetrahydropyrido[2,3-d]pyrimidin-5-yl)oxy]phenyl}urea,
N-{3-fluoro-4-[(6-oxo-3,4,7,11b-tetrahydro-2H,6H-pyrido[2',3':4,5]pyrimido[6,1-b][1,3]oxazin-11-yl)oxy]phenyl}-1-(4-fluorophenyl)-2-oxo-1,2-dihydropyridine-3-carboxamide,
N-{4-[(3-ethyl-2-oxo-1,2,3,4-tetrahydropyrido[2,3-d]pyrimidin-5-yl)oxy]-3-fluorophenyl}-1-(4-fluorophenyl)-2-oxo-1,2-dihydropyridine-3-carboxamide,
N-(3-fluoro-4-{[2-oxo-3-(2,2,2-trifluoroethyl)-1,2,3,4-tetrahydropyrido[2,3-d]pyrimidin-5-yl]oxy}phenyl)-1-(4-fluorophenyl)-2-oxo-1,2-dihydropyridine-3-carboxamide,
2-fluoro-N-{3-fluoro-4-[(2-oxo-1,2,3,4-tetrahydropyrido[2,3-d]pyrimidin-5-yl)oxy]phenyl}-3-(trifluoromethyl) benzamide,
3-cyano-N-{3-fluoro-4-[(2-oxo-1,2,3,4-tetrahydropyrido[2,3-d]pyrimidin-5-yl)oxy]phenyl}benzamide,
N-{3-fluoro-4-[(2-oxo-1,2,3,4-tetrahydropyrido[2,3-d]pyrimidin-5-yl)oxy]phenyl}-3-methoxybenzamide,
N-{3-fluoro-4-[(2-oxo-1,2,3,4-tetrahydropyrido[2,3-d]pyrimidin-5-yl)oxy]phenyl}-3-methylbenzamide,
3-fluoro-N-{3-fluoro-4-[(2-oxo-1,2,3,4-tetrahydropyrido[2,3-d]pyrimidin-5-yl)oxy]phenyl}benzamide,
4-bromo-N-{3-fluoro-4-[(2-oxo-1,2,3,4-tetrahydropyrido[2,3-d]pyrimidin-5-yl)oxy]phenyl}benzamide,
2-cyclopropyl-N-{4-[(2-oxo-1,2,3,4-tetrahydropyrido[2,3-d]pyrimidin-5-yl)amino]phenyl}acetamide,
4-fluoro-N-(3-fluoro-4-{[3-(4-methoxybenzyl)-2-oxo-1,2,3,4-tetrahydropyrido[2,3-d]pyrimidin-5-yl]amino}phenyl)-2-(trifluoromethyl)benzamide,
4-fluoro-N-{3-fluoro-4-[(2-oxo-1,2,3,4-tetrahydropyrido[2,3-d]pyrimidin-5-yl)amino]phenyl}-2-(trifluoromethyl)benzamide,
3-fluoro-N-{3-fluoro-4-[(2-oxo-1,2,3,4-tetrahydropyrido[2,3-d]pyrimidin-5-yl)amino]phenyl}benzamide,
2-fluoro-N-{3-fluoro-4-[(2-oxo-1,2,3,4-tetrahydropyrido[2,3-d]pyrimidin-5-yl)amino]phenyl}benzamide,
N-[4-fluoro-2-(trifluoromethyl)phenyl]-N'-{4-[(2-oxo-1,2,3,4-tetrahydropyrido[2,3-d]pyrimidin-5-yl)amino]phenyl}urea,
1-[3-Fluoro-4-(2-oxo-1,2,3,4-tetrahydro-pyrido[2,3-d]pyrimidin-5-yloxy)-phenyl]-3-(4-isopropyl-phenyl)-urea,
or a pharmaceutically acceptable salt thereof.

10. A pharmaceutical kit consisting of separate packs of:
a) a pharmaceutical composition comprising a compound according to claim 1, or a pharmaceutically acceptable salt thereof, and a pharmaceutically acceptable carrier and
b) an effective amount of a further medicament active ingredient.

11. A pharmaceutical kit consisting of separate packs of:
c) a pharmaceutical composition comprising a compound according to claim 9, or a pharmaceutically acceptable salt thereof, and a pharmaceutically acceptable carrier, and
d) an effective amount of a further medicament active ingredient.

12. The compound according to claim 3, wherein X is NH or O, or a pharmaceutically acceptable salt thereof.

13. The compound according to claim 3, wherein X is NH and M is CONH, or a pharmaceutically acceptable salt thereof.

14. The compound according to claim 3, wherein X is O and M is CONH, or a pharmaceutically acceptable salt thereof.

15. The compound according to claim 3, wherein $R^4$ is H or F, and $R^{5'}$ and $R^{5'''}$ each, independently of one another, are H, F, Br, CN, $CH_3$, $OCH_3$ or $CF_3$, or a pharmaceutically acceptable salt thereof.

16. The compound according to claim 3, wherein M is NHCONH or CONH, or a pharmaceutically acceptable salt thereof.

17. The compound according to claim 3, wherein $R^1$ is H, or a pharmaceutically acceptable salt thereof.

18. The compound according to claim 3, wherein $R^1$ is H and M is CONH, or a pharmaceutically acceptable salt thereof.

19. The compound according to claim 3, wherein $R^1$ is A, Ar or Ar-A, or a pharmaceutically acceptable salt thereof.

20. The compound according to claim 3, wherein $R^1$ is A, Ar or Ar-A, and M is CONH, or a pharmaceutically acceptable salt thereof.

21. The compound according to claim 3, wherein $R^4$ is H or F, and $R^{5'}$ and $R^{5'''}$ each, independently of one another, are H, F or $CF_3$, or a pharmaceutically acceptable salt thereof.

22. The compound according to claim 3, wherein $R^4$ is H or F, $R^{5'}$ is 4-fluoro, and $R^{5'''}$ is 2-(trifluoromethyl), or a pharmaceutically acceptable salt thereof.

23. The compound according to claim 3, wherein $R^1$ is ethyl, or a pharmaceutically acceptable salt thereof.

24. The compound according to claim 4, wherein X is NH or O, or a pharmaceutically acceptable salt thereof.

25. The compound according to claim 4, wherein X is NH and M is CONH, or a pharmaceutically acceptable salt thereof.

26. The compound according to claim 4, wherein X is O and M is CONH, or a pharmaceutically acceptable salt thereof.

27. The compound according to claim 4, wherein $R^4$ is H or F, or a pharmaceutically acceptable salt thereof.

28. The compound according to claim 4, wherein M is NHCONH or CONH, or a pharmaceutically acceptable salt thereof.

29. The compound according to claim 4, wherein $R^1$ is H, or a pharmaceutically acceptable salt thereof.

30. The compound according to claim 4, wherein $R^1$ is H and M is CONH, or a pharmaceutically acceptable salt thereof.

31. The compound according to claim 4, wherein $R^1$ is A, Ar or Ar-A, or a pharmaceutically acceptable salt thereof.

32. The compound according to claim 4, wherein $R^1$ is A, Ar or Ar-A, and M is CONH, or a pharmaceutically acceptable salt thereof.

33. The compound according to claim 4, wherein $R^4$ is H or F, and $R^{5'}$ and $R^{5'''}$ each, independently of one another, are H, F or $CF_3$, or a pharmaceutically acceptable salt thereof.

34. The compound according to claim 4, wherein $R^1$ is ethyl, or a pharmaceutically acceptable salt thereof.

35. The compound according to claim 5, wherein X is NH or O, or a pharmaceutically acceptable salt thereof.

36. The compound according to claim 5, wherein X is NH and M is CONH, or a pharmaceutically acceptable salt thereof.

37. The compound according to claim 5, wherein X is O and M is CONH, or a pharmaceutically acceptable salt thereof.

38. The compound according to claim 5, wherein $R^4$ is H or F, or a pharmaceutically acceptable salt thereof.

39. The compound according to claim 5, wherein M is NHCONH or CONH, or a pharmaceutically acceptable salt thereof.

40. The compound according to claim 6, wherein X is NH or O, or a pharmaceutically acceptable salt thereof.

41. The compound according to claim 6, wherein X is NH and M is CONH, or a pharmaceutically acceptable salt thereof.

42. The compound according to claim 6, wherein X is O and M is CONH, or a pharmaceutically acceptable salt thereof.

43. The compound according to claim 6, wherein $R^4$ is H or F, or a pharmaceutically acceptable salt thereof.

44. The compound according to claim 7, wherein X is NH or O, or a pharmaceutically acceptable salt thereof.

45. The compound according to claim 7, wherein X is NH and M is CONH, or a pharmaceutically acceptable salt thereof.

46. The compound according to claim 7, wherein X is O and M is CONH, or a pharmaceutically acceptable salt thereof.

47. The compound according to claim 7, wherein $R^4$ is H or F, and $R^{5'}$ and $R^{5'''}$ each independently of one another, are H, F, Br, CN, $CH_3$, $OCH_3$ or $CF_3$, or a pharmaceutically acceptable salt thereof.

48. The compound according to claim 7, wherein M is NHCONH or CONH, or a pharmaceutically acceptable salt thereof.

49. The compound according to claim 7, wherein $R^4$ is H or F, and $R^{5'}$ and $R^{5'''}$ each independently of one another, are H, F or $CF_3$, or a pharmaceutically acceptable salt thereof.

50. The compound according to claim 7, wherein $R^4$ is H or F, $R^{5'}$ is 4-fluoro, and $R^{5'''}$ is 2-(trifluoromethyl), or a pharmaceutically acceptable salt thereof.

51. The compound according to claim 8, wherein X is NH or O, or a pharmaceutically acceptable salt thereof.

52. The compound according to claim 8, wherein X is NH and M is CONH, or a pharmaceutically acceptable salt thereof.

53. The compound according to claim 8, wherein X is O and M is CONH, or a pharmaceutically acceptable salt thereof.

54. The compound according to claim 8, wherein $R^4$ is H or F, and $R^{5'}$ and $R^{5'''}$ each, independently of one another, are H, F, Br, CN, $CH_3$, $OCH_3$ or $CF_3$, or a pharmaceutically acceptable salt thereof.

55. The compound according to claim 8, wherein M is NHCONH or CONH, or a pharmaceutically acceptable salt thereof.

56. The compound according to claim 8, wherein $R^4$ is H or F, and $R^{5'}$ and $R^{5'''}$ each, independently of one another, are H, F or $CF_3$, or a pharmaceutically acceptable salt thereof.

57. The compound according to claim 8, wherein $R^4$ is H or F, $R^{5'''}$ is 4-fluoro, and $R^{5'''}$ is 2-(trifluoromethyl), or a pharmaceutically acceptable salt thereof.

58. The compound according to claim 1 wherein X is a bond.

59. The compound according to claim 1 wherein X is a bond, and Q is thienyl.

60. The compound according to claim 1 wherein X is a bond, Q is thienylm and M is CH2NHCO, and wherein the CO moiety is connected to Q.

* * * * *